United States Patent
Roman et al.

(10) Patent No.: US 11,576,705 B2
(45) Date of Patent: *Feb. 14, 2023

(54) INTRAMEDULLARY FIXATION DEVICES

(71) Applicant: ARROWHEAD MEDICAL DEVICE TECHNOLOGIES, LLC, Collierville, TN (US)

(72) Inventors: Scott R. Roman, Hampton, GA (US); Thomas J. Twardzik, Germantown, TN (US)

(73) Assignee: ARROWHEAD MEDICAL DEVICE TECHNOLOGIES, LLC, Collierville, TN (US)

( * ) Notice: Subject to any disclaimer, the term of this patent is extended or adjusted under 35 U.S.C. 154(b) by 213 days.

This patent is subject to a terminal disclaimer.

(21) Appl. No.: 17/157,069

(22) Filed: Jan. 25, 2021

(65) Prior Publication Data

US 2021/0137572 A1 May 13, 2021

Related U.S. Application Data

(60) Continuation of application No. 16/453,411, filed on Jun. 26, 2019, now Pat. No. 10,898,243, which is a
(Continued)

(51) Int. Cl.
*A61B 17/72* (2006.01)
*A61F 2/42* (2006.01)
(Continued)

(52) U.S. Cl.
CPC ...... *A61B 17/7291* (2013.01); *A61B 17/7233* (2013.01); *A61B 17/7283* (2013.01);
(Continued)

(58) Field of Classification Search
CPC ............ A61B 17/7291; A61B 17/7233; A61B 17/7283; A61B 17/0642; A61B 17/164;
(Continued)

(56) References Cited

U.S. PATENT DOCUMENTS 3,593,342 A 7/1971 Niebauer et al.
3,646,615 A 3/1972 Ness
(Continued)

FOREIGN PATENT DOCUMENTS

DE 19813914 9/1999
DE 20212359 11/2002
(Continued)

OTHER PUBLICATIONS

U.S. Appl. No. 14/776,013, filed Sep. 14, 2015, titled "Hammertoe Implant With Asymmetrical Head.".
(Continued)

*Primary Examiner* — Nicholas J Plionis
(74) *Attorney, Agent, or Firm* — Heslin Rothenberg Farley & Mesiti PC; Kristian E. Ziegler, Esq.

(57) ABSTRACT

An internal intramedullary fixation device for the stabilization of bone in arthrodesis and fractures of the foot and hand is disclosed. During implantation in medullary canals of bones, the device grasps the edges of the canals, stabilizing the bones, internally, during a healing process. The intramedullary fixation device comprises arrow-shaped proximal and distal heads comprising tips and a pairs of wings, the heads being sized to fit within an intramedullary canal of a bone. The intramedullary fixation device also comprises a rigid body defining a longitudinal axis connecting the proximal and distal heads. The rigid body comprises an intermediate portion, a distal neck portion connecting the rigid body to the distal head, and a proximal neck portion connecting the rigid body to the proximal head, the neck portions having a cross-sectional area smaller than a cross-section area of the intermediate portion.

20 Claims, 31 Drawing Sheets

Related U.S. Application Data continuation of application No. 15/900,325, filed on Feb. 20, 2018, now Pat. No. 10,349,987, which is a continuation-in-part of application No. 15/619,831, filed on Jun. 12, 2017, now Pat. No. 9,924,985, which is a continuation of application No. 14/776,066, filed as application No. PCT/US2014/024485 on Mar. 12, 2014, now Pat. No. 9,675,391, said application No. 15/900,325 is a continuation-in-part of application No. 14/776,013, filed as application No. PCT/US2014/024599 on Mar. 12, 2014, now Pat. No. 9,974,580, said application No. 15/900,325 is a continuation-in-part of application No. 15/493,329, filed on Apr. 21, 2017, now Pat. No. 9,895,179, which is a continuation of application No. 14/514,711, filed on Oct. 15, 2014, now Pat. No. 9,629,671, which is a continuation of application No. 14/162,226, filed on Jan. 23, 2014, now Pat. No. 8,888,778, which is a division of application No. 13/084,048, filed on Apr. 11, 2011, now Pat. No. 8,685,024.

(60) Provisional application No. 61/780,360, filed on Mar. 13, 2013, provisional application No. 61/780,316, filed on Mar. 13, 2013, provisional application No. 61/324,080, filed on Apr. 14, 2010.

(51) Int. Cl.
*A61F 2/28* (2006.01)
*A61B 17/00* (2006.01)
*A61B 17/064* (2006.01)
*A61B 17/16* (2006.01)
*A61B 17/88* (2006.01)
*A61B 90/00* (2016.01)

(52) U.S. Cl.
CPC .............. *A61F 2/28* (2013.01); *A61F 2/4225* (2013.01); *A61B 17/0642* (2013.01); *A61B 17/164* (2013.01); *A61B 17/8872* (2013.01); *A61B 2017/00831* (2013.01); *A61B 2017/00982* (2013.01); *A61B 2017/0647* (2013.01); *A61B 2090/062* (2016.02); *A61F 2002/4233* (2013.01)

(58) Field of Classification Search
CPC ........ A61B 17/8872; A61B 2017/0647; A61B 2090/062; A61F 2/28
See application file for complete search history.

(56) References Cited

U.S. PATENT DOCUMENTS

| | | | |
|---|---|---|---|
| 3,681,786 A | 8/1972 | Lynch | |
| 3,875,594 A | 4/1975 | Swanson | |
| 4,262,665 A | 4/1981 | Roalstad et al. | |
| 4,304,011 A | 12/1981 | Whelan, III | |
| 4,516,569 A | 5/1985 | Evans et al. | |
| 4,549,319 A | 10/1985 | Meyer | |
| 4,667,663 A | 5/1987 | Miyata | |
| 4,704,686 A | 11/1987 | Aldinger | |
| 4,873,976 A | 10/1989 | Schreiber | |
| 4,884,572 A | 12/1989 | Bays et al. | |
| 4,898,186 A | 2/1990 | Ikada et al. | |
| 4,976,715 A | 12/1990 | Bays et al. | |
| 5,047,059 A | 9/1991 | Saffar | |
| 5,053,035 A | 10/1991 | McLaren | |
| 5,171,284 A | 12/1992 | Branemark | |
| 5,201,735 A | 4/1993 | Chapman et al. | |
| 5,203,864 A | 4/1993 | Phillips | |
| 5,236,431 A | 8/1993 | Gogolewski et al. | |
| 5,391,181 A | 2/1995 | Johnson et al. | |
| 5,425,777 A | 6/1995 | Sarkisian et al. | |
| 5,474,557 A | 12/1995 | Mai | |
| 5,480,447 A | 1/1996 | Skiba | |
| 5,667,510 A | 9/1997 | Combs | |
| 5,669,912 A | 9/1997 | Spetzier | |
| 5,824,095 A | 10/1998 | Di Maio, Jr. et al. | |
| 5,893,850 A | 4/1999 | Cachia | |
| 5,919,193 A | 7/1999 | Slavitt | |
| 5,938,700 A | 8/1999 | Lippincott | |
| 5,984,971 A | 11/1999 | Faccioli et al. | |
| 5,993,475 A | 11/1999 | Lin et al. | |
| 6,319,284 B1 | 11/2001 | Rushdy et al. | |
| 6,352,560 B1 | 3/2002 | Poeschmann et al. | |
| 6,689,169 B2 | 2/2004 | Harris | |
| 6,692,499 B2 | 2/2004 | Tormala et al. | |
| 6,736,818 B2 | 5/2004 | Perren et al. | |
| 6,811,568 B2 | 11/2004 | Minamikawa | |
| 7,025,789 B2 | 4/2006 | Chow et al. | |
| 7,041,106 B1 | 5/2006 | Carver et al. | |
| 7,381,213 B2 | 6/2008 | Lizardi | |
| 7,918,879 B2 | 4/2011 | Yeung et al. | |
| 8,100,983 B2 | 1/2012 | Schulte | |
| 8,202,306 B2 | 6/2012 | Dreyfuss | |
| 8,328,806 B2 | 12/2012 | Tyber et al. | |
| 8,337,537 B2 | 12/2012 | Pelo et al. | |
| 8,357,162 B2 | 1/2013 | Frake | |
| 8,414,583 B2 | 4/2013 | Prandi et al. | |
| 8,475,456 B2 | 7/2013 | Augoyard et al. | |
| 8,672,986 B2 | 3/2014 | Klaue et al. | |
| 8,685,024 B2 | 4/2014 | Roman | |
| 8,696,716 B2 | 4/2014 | Kartalian et al. | |
| 8,715,325 B2 | 5/2014 | Weiner et al. | |
| 8,888,778 B2 | 11/2014 | Roman | |
| 9,629,671 B2 | 4/2017 | Roman | |
| 9,675,391 B2 | 6/2017 | Roman et al. | |
| 9,895,179 B2 | 2/2018 | Roman et al. | |
| 9,924,985 B2 | 3/2018 | Roman et al. | |
| 9,974,580 B2 | 5/2018 | Roman et al. | |
| 10,349,987 B2* | 7/2019 | Roman .............. | A61B 17/7291 |
| 10,898,243 B2* | 1/2021 | Roman .................... | A61F 2/28 |
| 2002/0082705 A1 | 6/2002 | Bouman et al. | |
| 2004/0220574 A1* | 11/2004 | Pelo .................. | A61B 17/0642 606/313 |
| 2006/0129153 A1 | 6/2006 | Klaue et al. | |
| 2007/0060923 A1 | 3/2007 | Dreyfuss | |
| 2007/0083202 A1 | 4/2007 | Running et al. | |
| 2007/0243225 A1 | 10/2007 | McKay | |
| 2008/0132894 A1 | 6/2008 | Coilard-Lavirotte et al. | |
| 2008/0177262 A1 | 7/2008 | Augoyard et al. | |
| 2008/0195219 A1 | 8/2008 | Wiley et al. | |
| 2008/0221697 A1 | 9/2008 | Graser | |
| 2009/0005782 A1 | 1/2009 | Chirico et al. | |
| 2009/0036893 A1 | 2/2009 | Kartalian et al. | |
| 2010/0131072 A1 | 5/2010 | Schulte | |
| 2010/0324556 A1 | 12/2010 | Tyber et al. | |
| 2011/0004255 A1 | 1/2011 | Weiner et al. | |
| 2011/0118739 A1 | 5/2011 | Tyber et al. | |
| 2011/0144644 A1 | 6/2011 | Prandi et al. | |
| 2011/0172668 A1 | 7/2011 | Frake | |
| 2011/0257652 A1* | 10/2011 | Roman .................. | A61B 17/16 606/62 |
| 2011/0257755 A1 | 10/2011 | Bellemere et al. | |
| 2011/0276099 A1 | 11/2011 | Champagne et al. | |
| 2011/0301652 A1 | 12/2011 | Reed et al. | |
| 2012/0089197 A1 | 4/2012 | Anderson | |
| 2013/0123862 A1 | 5/2013 | Anderson et al. | |
| 2013/0172889 A1 | 7/2013 | Tyber et al. | |
| 2016/0030096 A1 | 2/2016 | Roman et al. | |
| 2018/0168703 A1 | 6/2018 | Roman et al. | |

FOREIGN PATENT DOCUMENTS

| | | |
|---|---|---|
| DE | 10134511 | 2/2003 |
| DE | 20218993 | 2/2003 |
| EP | 1870050 | 12/2007 |
| FR | 2846545 | 5/2004 |
| GB | 2430625 | 4/2007 |
| JP | 56144512 | 10/1981 |

(56) References Cited

FOREIGN PATENT DOCUMENTS

| WO | 2005063149 | 7/2005 |
|---|---|---|
| WO | 2006099886 | 9/2006 |
| WO | 2011130229 | 10/2011 |

OTHER PUBLICATIONS

Integra™ "IPP-ON™ Interphalangeal Implant" 2008, 6 pages.
Plionis, First Office Action for U.S. Appl. No. 14/776,066 dated Jun. 6, 2016, 24 pages.
Extended European Search Report issued in European Patent Application No. 14780322.5 dated Nov. 16, 2016, 9 pages.
International Searching Authority/United States Patent Office, "International Search Report" for PCT/US2011/032057, dated Jul. 5, 2011, 2 pages.
Smart Toe Intramedullary Shape memory implant, product information, Memometal, Inc., 2009, 2 pages.
Pro-Toe Vo hammertoe Fixation System, Surgical Technique, FA196-410R311, Wright Medical Technology, Inc., 2011, 12 pages.
Crenshaw, A.H., ad., "Campbell's Operative Orthopaedics, vol. 2," 7th edition, The C.V. Mosby Company, Washington DC, 1987, p. 937-945, cover and copyright pages, 11 pages.
International Search Report and Written Opinion issue for PCT/US2014/022058, dated Jun. 25, 2014, 15 pages.
Supplementary European Search Report issued for EP 11769413 dated May 6, 2014, 6 pages.
International Search Report and Written Opinion issue for PCT/US2014/024599, dated Aug. 6, 2014, 11 pages.
International Search Report and Written Opinion issue for PCT/US2014/024485, dated Jul. 10, 2014, 17 pages.

\* cited by examiner

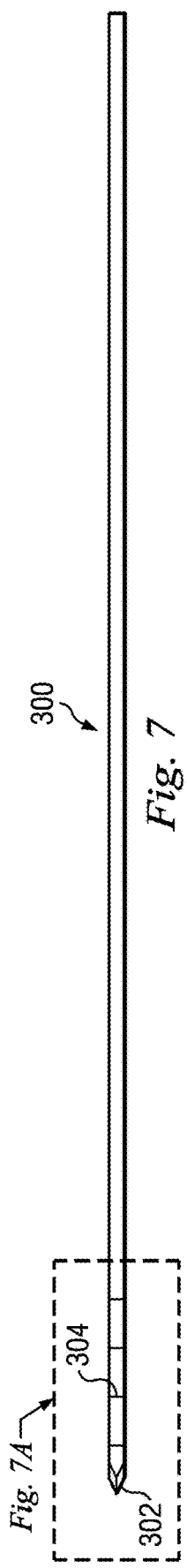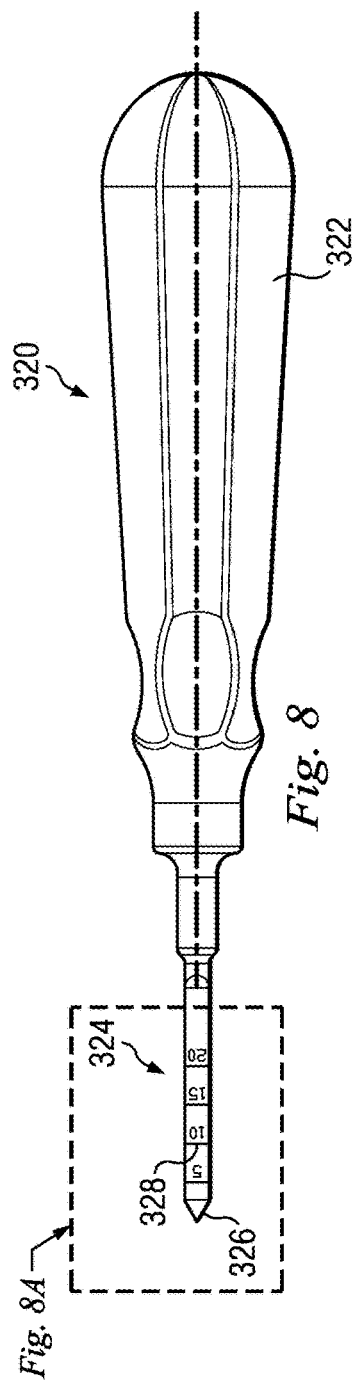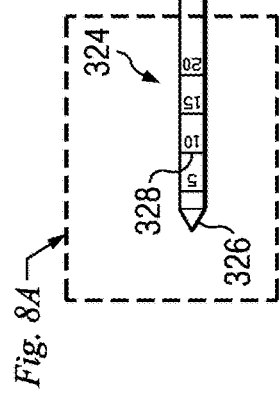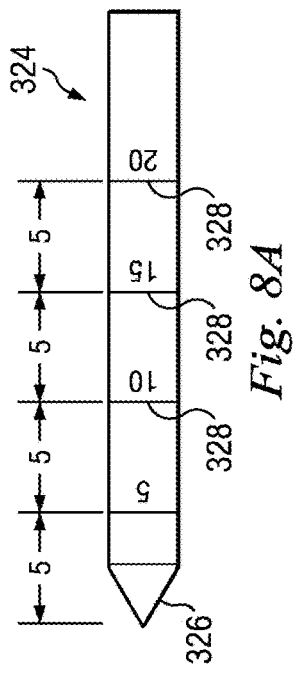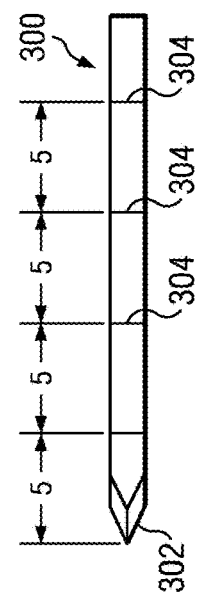

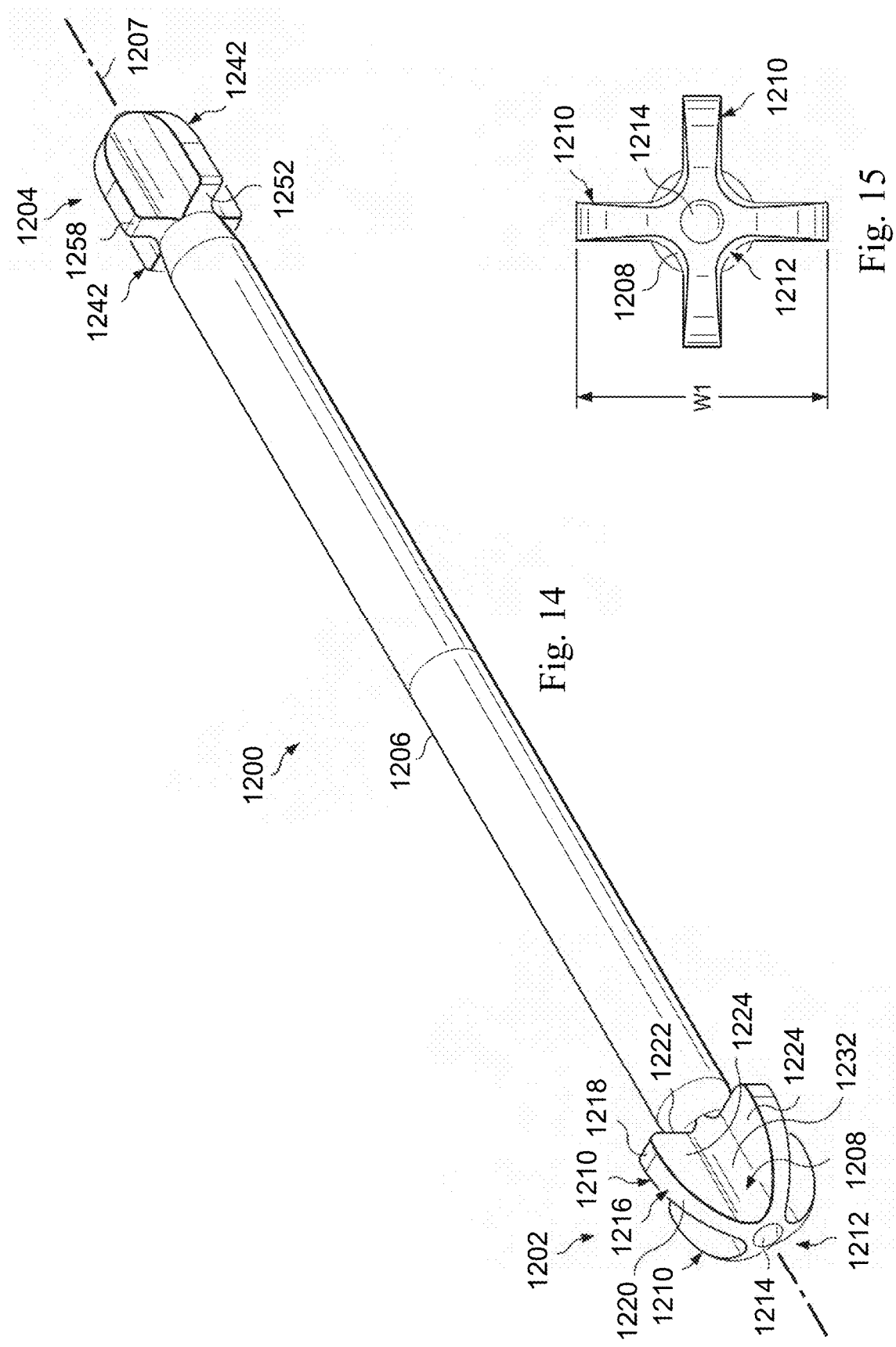

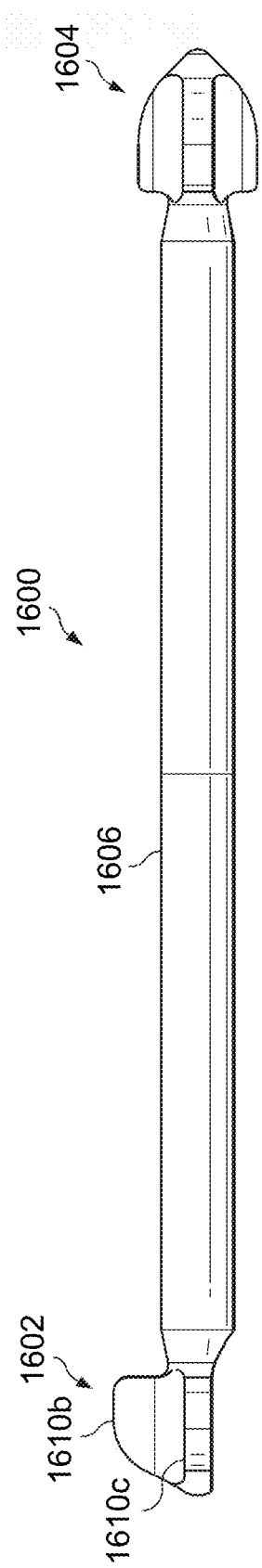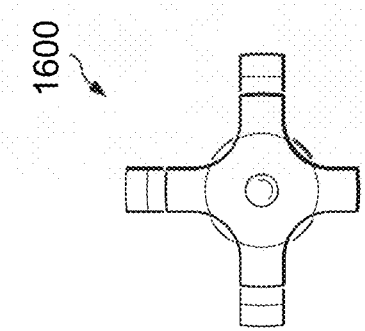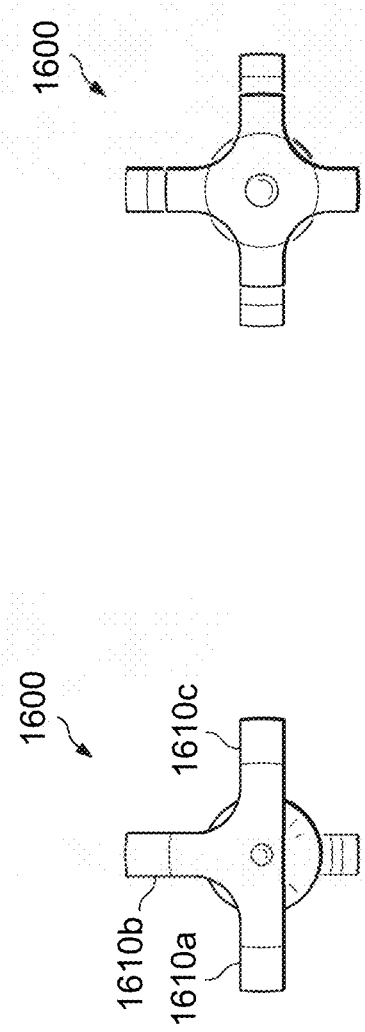

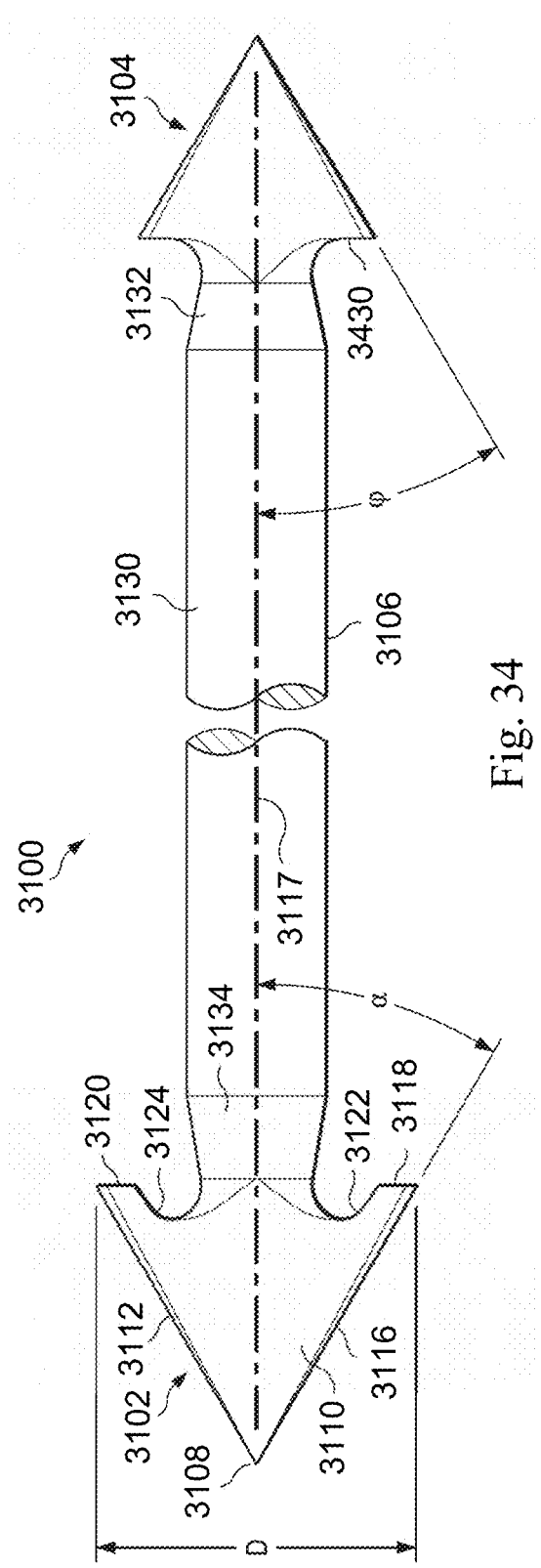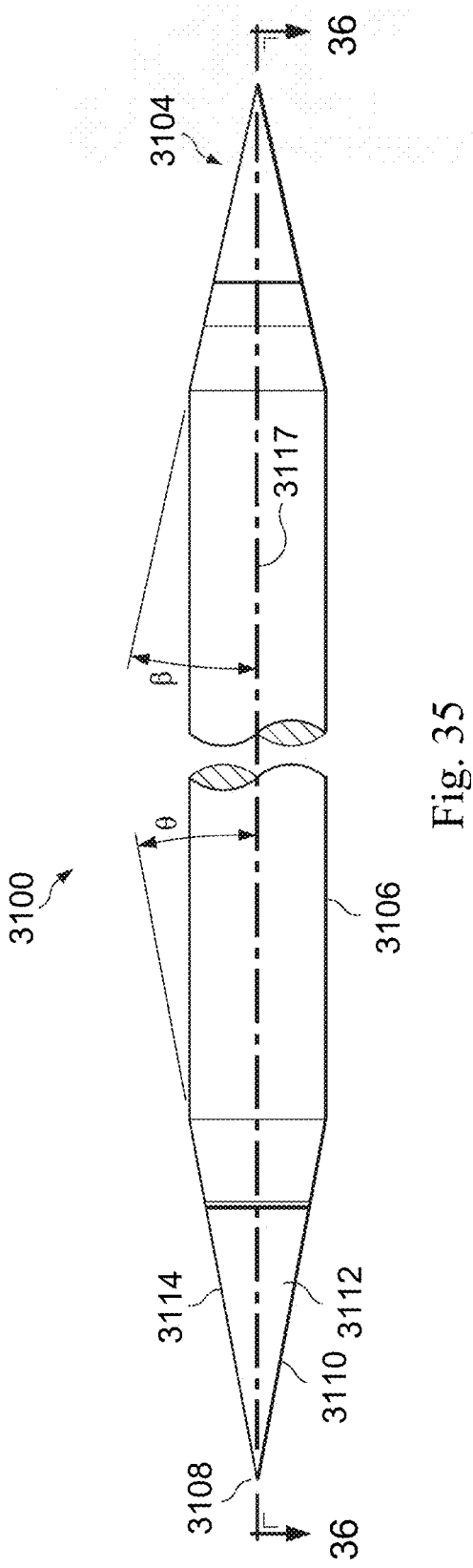

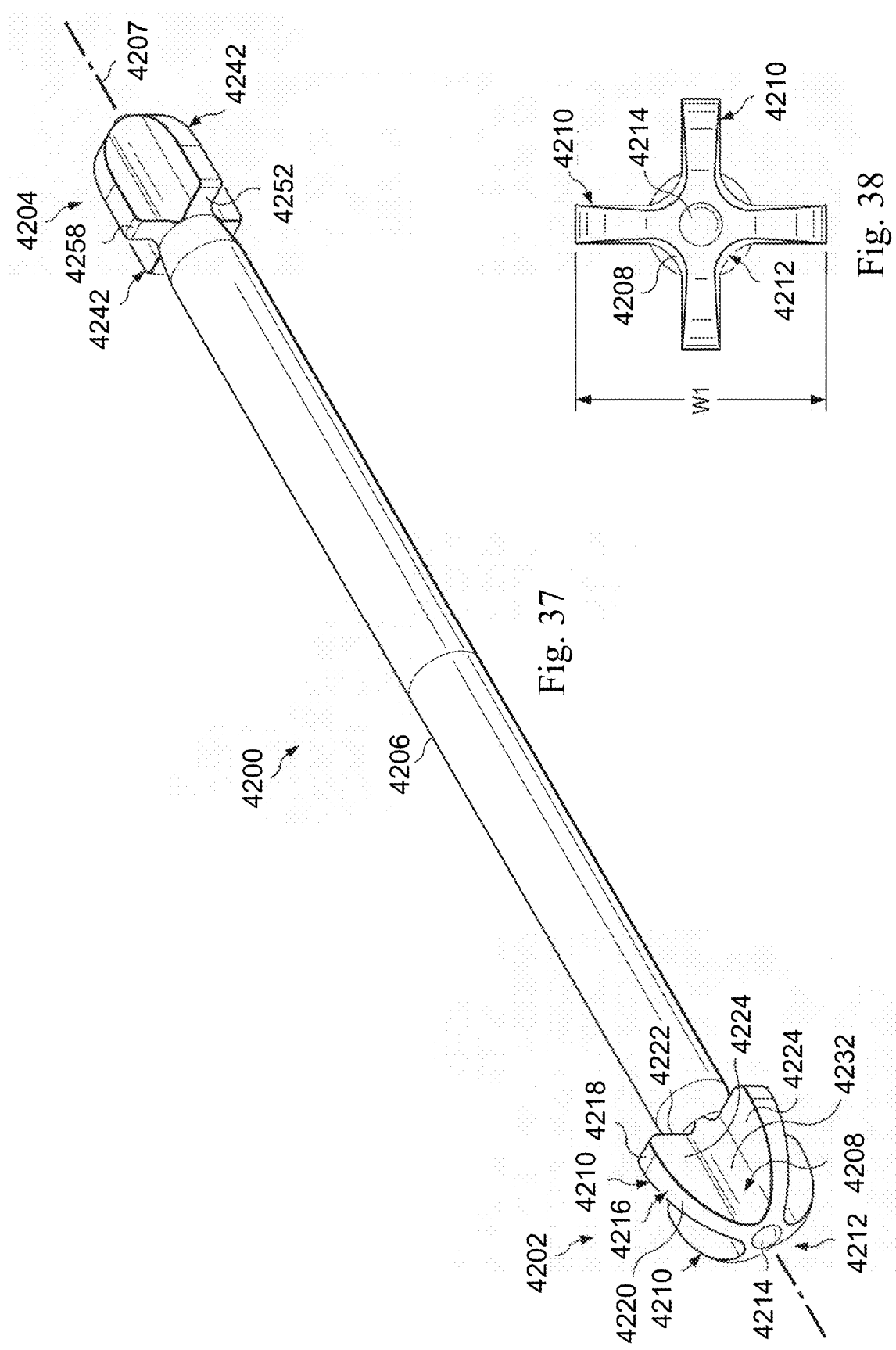

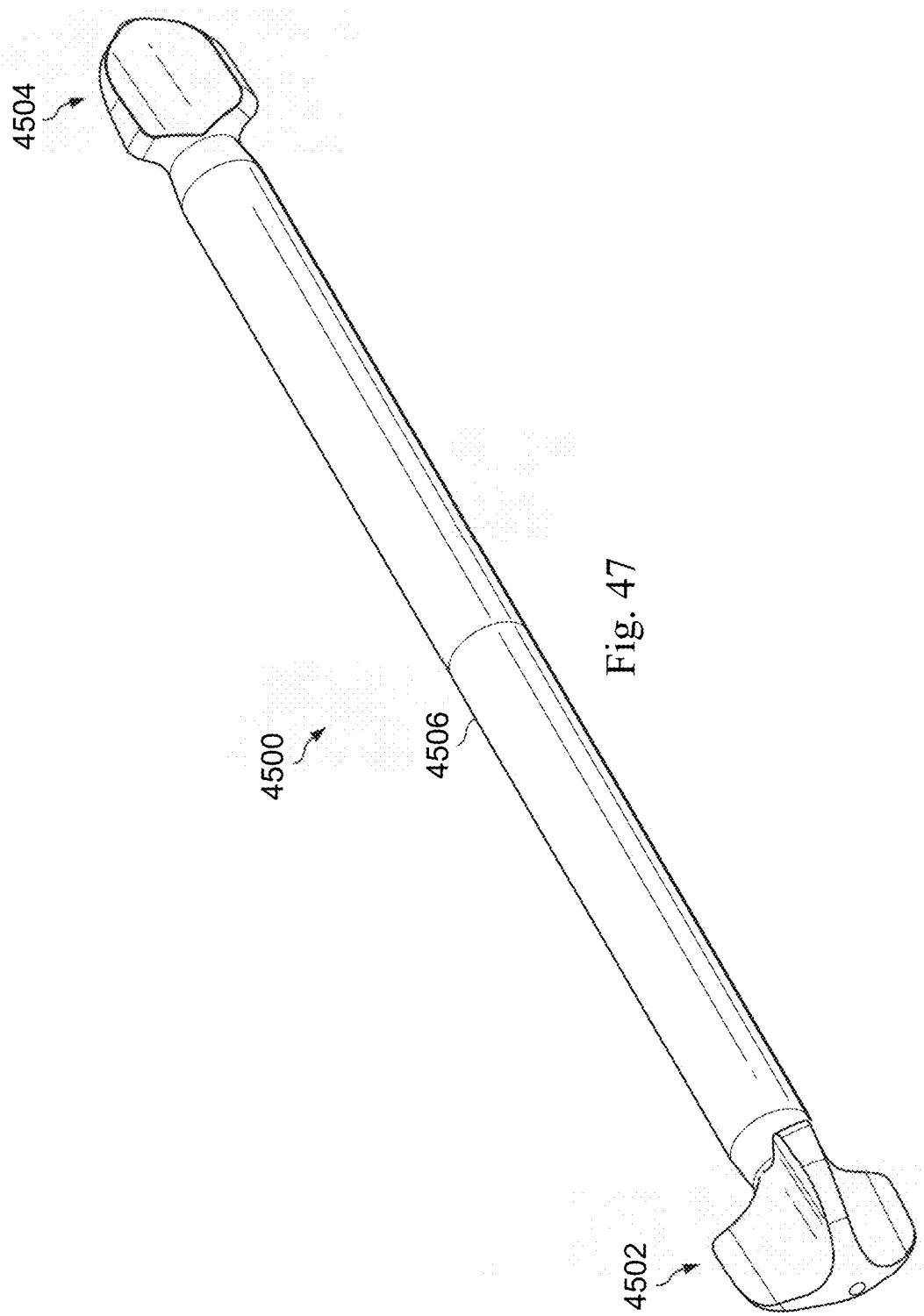

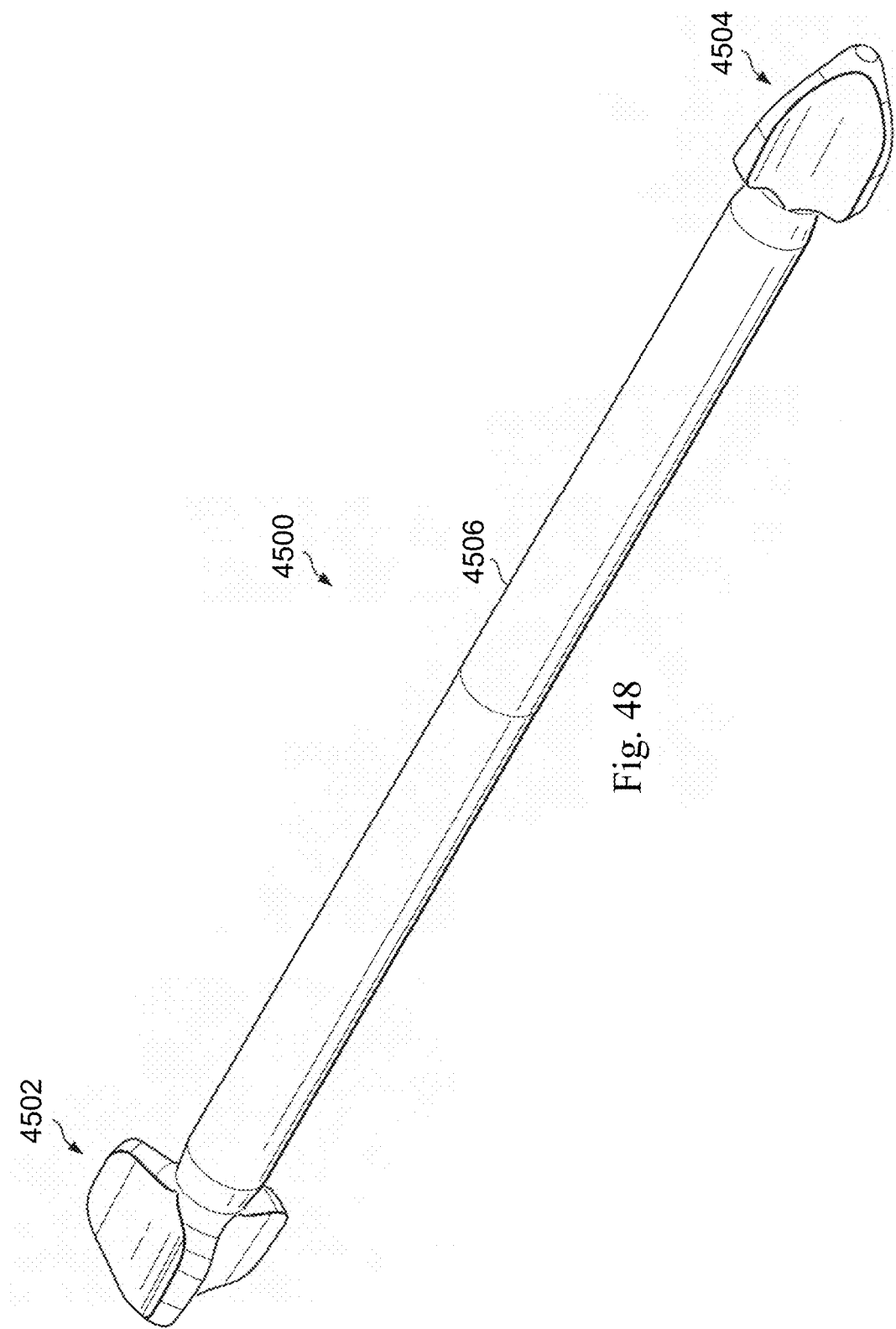

INTRAMEDULLARY FIXATION DEVICES

CROSS-REFERENCE TO RELATED APPLICATIONS

The present application is a continuation of U.S. patent application Ser. No. 16/453,411, filed on Jun. 26, 2019, which is a continuation of U.S. patent application Ser. No. 15/900,325, filed on Feb. 20, 2018, which are hereby incorporated herein by reference in their entireties. U.S. patent application Ser. No. 15/900,325 is a continuation-in-part of application of U.S. patent application Ser. No. 15/493,329, filed on Apr. 21, 2017, which is a continuation application of U.S. patent application Ser. No. 14/514,711, filed on Oct. 15, 2014, which is a continuation application of U.S. patent application Ser. No. 14/162,226, filed on Jan. 23, 2014, which is a divisional application of U.S. patent application Ser. No. 13/084,048, filed on Apr. 11, 2011, which claims the benefit of U.S. Provisional Application No. 61/324,080, filed Apr. 14, 2010, each of which is hereby incorporated herein by reference in its entirety. U.S. patent application Ser. No. 15/900,325 is also a continuation-in-part of application of U.S. patent application Ser. No. 15/619,831, filed on Jun. 12, 2017, which is a continuation application of U.S. patent application Ser. No. 14/776,066, filed on Sep. 14, 2015, which is a national stage entry of PCT/US2014/024485, filed Mar. 12, 2014, which claims the benefit of U.S. Provisional Application No. 61/780,360, filed Mar. 13, 2013, each of which is hereby incorporated herein by reference in its entirety. U.S. patent application Ser. No. 15/900,325 is also a continuation-in-part of application of U.S. patent application Ser. No. 14/776,013, filed on Sep. 14, 2015, which is a national stage entry of PCT/US2014/024599, filed Mar. 12, 2014, which claims the benefit of U.S. Provisional Application No. 61/780,316, filed Mar. 13, 2013, each of which is hereby incorporated herein by reference in its entirety.

BACKGROUND

Hammertoe deformities occur when the metatarsophalangeal joint between phalanges in a toe are cocked upward and the proximal interphalangeal joint bends downward. This deformity can become quite painful and can limit the ability of a person with hammertoe to walk and perform other daily activities. Hammertoe may be caused by any number of factors, including the long-term use of poorly fitting shoes, having a long second toe, hallux valgus pressing against the second toe, connective tissue disorders and trauma.

While some minor cases may be treated with non-surgical remedies, surgeries are often necessary to provide real correction and pain relief. Some surgical methods include stabilizing the toes using a smooth K-wire placed in an antegrade manner through the middle and distal phalanges while joint extension and distraction are maintained. The K-wire may then be placed in retrograde fashion into the proximal phalanx while joint extension and distraction are maintained. Fixation lasts for 4-6 weeks after surgery. During that time, the pins are capped so that the sharp ends do not catch on objects, such as bed sheets. Even with this form of fixation, non-unions, K-wire migration, and loss of fixation can be quite common. Further, the external K-wires may lead to pin tract infections or movement of bone along the smooth wire, including rotation of the distal aspect of the toe. These types of challenges make alternative fixation methods desirable.

The devices and methods disclosed herein overcome one or more of the problems in the prior art.

SUMMARY

In one exemplary aspect, the present disclosure is directed to an intramedullary fixation device used in bone fixation and stabilization. The device may include an arrowhead-shaped distal head comprising a distal end having a sharp point and comprising first, second, third, and fourth outwardly facing side surfaces forming a pyramidal shape. The first and third side surfaces may be opposed from each other and may form a first angle, and the second and fourth side surfaces may be opposed from each other and may form a second angle. The second angle may be different than the first angle. Each of the first and third side surfaces may have a proximally projecting edge forming a tip of a barb. The barbs may be configured to engage tissue and inhibit rotational movement and inhibit axial movement of the distal head in a proximal direction. The device may also include an arrowhead-shaped proximal head comprising a proximal end having a sharp point and comprising fifth, sixth, seventh, and eighth outwardly facing side surfaces. The fifth and seventh side surfaces may be opposed from each other and may form a third angle. The sixth and eighth side surfaces may be opposed from each other and may form a fourth angle, with the third angle being different than the fourth angle. Each of the fifth and seventh side surfaces may have a distally projecting edge forming a tip of a barb. The barbs may be configured to engage tissue and inhibit rotational movement and inhibit axial movement of the proximal head in a distal direction. A rigid body extends between and connects the distal head and the proximal head. The body may have a rigidity sufficient to withstand bending loading applied by the phalanges.

In another exemplary aspect, the present disclosure is directed to an intramedullary fixation device used in bone fixation and stabilization. The device may include an arrowhead-shaped distal head having first, second, third, and fourth outwardly facing side surfaces forming a pyramidal shape. The first and third side surfaces may be opposed from each other and may form a first angle, and the second and fourth side surfaces may be opposed from each other and may form a second angle. Each of the first and third side surfaces may have a proximally projecting edge forming a tip of a barb. The barbs being configured to engage tissue and inhibit movement of the distal head in a proximal direction. The second and fourth side surfaces lack proximal edges forming barbs. The device may also include an arrowhead-shaped proximal head having fifth, sixth, seventh, and eighth outwardly facing side surfaces. The fifth and seventh side surfaces may be opposed from each other and may form a third angle, and the sixth and eighth side surfaces may be opposed from each other and may form a fourth angle. Each of the fifth and seventh side surfaces may have a distally projecting edge forming a tip of a barb. The barbs may be configured to engage tissue and inhibit movement of the proximal head in a distal direction. The sixth and eighth side surfaces may lack proximal edges forming barbs. The device also may include a cylindrical body extending between and connecting the distal head and the proximal head. The cylindrical body may have a rigidity sufficient to withstand bending loading applied by the phalanges.

In another exemplary aspect, the present disclosure is directed to an intramedullary fixation device used in bone fixation and stabilization. The device may include an arrowhead-shaped distal head comprising a distal end having a sharp point and comprising first, second, third, and fourth outwardly facing side surfaces forming a pyramidal shape. The first and third side surfaces may be opposed from each other and may form a first angle, and the second and fourth side surfaces may be opposed from each other and may form a second angle, with the second angle being different than the first angle. Each of the first and third side surfaces may have a proximally projecting edge forming a tip of a barb. The distal head also may include a first undercut and a second undercut, where each of the first and second undercuts have a depth such that the barb tips are disposed proximal of the respective undercut. The barbs may be configured to engage tissue and inhibit movement of the distal head in a proximal direction. The derive may also include an arrowhead-shaped proximal head comprising a proximal end having a sharp point and comprising fifth, sixth, seventh, and eighth outwardly facing side surfaces. The fifth and seventh side surfaces may be opposed from each other and may form a third angle, and the sixth and eighth side surfaces may be opposed from each other and may form a fourth angle, with the third angle being different than the fourth angle. Each of the fifth and seventh side surfaces may have a distally projecting edge forming a tip of a barb. The proximal head also may comprise a third undercut and a fourth undercut. Each of the third and fourth undercuts may have a depth such that the barb tips are disposed distal of the respective undercut. The barbs may be configured to engage tissue and inhibit movement of the proximal head in a distal direction. A rigid body extends between and connects the distal head and the proximal head. The body may have a rigidity sufficient to withstand bending loading applied by the phalanges. It may comprise a main portion, a distal neck portion, and a proximal neck portion. The distal and proximal neck portions may have a cross-sectional area smaller than a cross-section area of the main portion. The distal neck portion may support the distal head and the proximal neck portion may support the proximal head. The distal neck may intersect with the first and second undercuts in the distal head and the proximal neck may intersect with the third and fourth undercuts in the proximal head.

In yet another exemplary aspect, the present disclosure is directed to a kit for bone fixation and stabilization. The kit may comprise an intramedullary fixation device and insertion forceps. The intramedullary fixation device may comprise an arrowhead-shaped distal head having first, second, third, and fourth outwardly facing side surfaces forming a pyramidal shape. The first and third side surfaces may be opposed from each other and may form a first angle, and the second and fourth side surfaces may be opposed from each other and may form a second angle. Each of the first and third side surfaces may have a proximally projecting edge forming a tip of a barb. The barbs may be configured to engage tissue and inhibit movement of the distal head in a proximal direction, and wherein the second and fourth side surfaces lack barbs. The device may also comprise an arrowhead-shaped proximal head having fifth, sixth, seventh, and eighth outwardly facing side surfaces. The fifth and seventh side surfaces may be opposed from each other and may form a third angle, and the sixth and eighth side surfaces may be opposed from each other and may form a fourth angle. Each of the fifth and seventh side surfaces may have a distally projecting edge forming a tip of a barb. The barbs may be configured to engage tissue and inhibit movement of the proximal head in a distal direction. The sixth and eighth side surfaces may lack barbs. A cylindrical body extends between and connects the distal head and the proximal head. The cylindrical body may have a rigidity sufficient to withstand bending loading applied by the phalanges. The insertion forceps may be configured to securably grasp the intramedullary fixation device, and may include a first nose piece having a first recess formed therein. The first recess may be sized to receive a portion of the cylindrical body of the intramedullary fixation device. The insertion forceps may also include a second nose piece having a second recess formed therein. The second recess may be sized to receive a portion of the cylindrical body of the intramedullary fixation device. The first and second nose pieces may be cooperatively arranged to securely grip the cylindrical body of the intramedullary fixation device sufficiently to prevent rotation and axial displacement under normal insertion conditions.

In yet another exemplary aspect, the present disclosure is directed to a method comprising a step of grasping an intramedullary fixation device, introducing a proximal end of the device into an intramedullary canal of a first bone element, introducing a distal end of the device into an intramedullary canal of a second bone element, releasing the intramedullary fixation device, and pressing the first and second bone elements together.

In yet another exemplary aspect the present disclosure is directed to an intramedullary fixation device used in bone fixation and stabilization. The device comprises an arrowhead-shaped distal head comprising a distal end having a sharp distal point and also comprising distal first, second, and third outwardly facing side surfaces converging toward and intersecting at the distal point. The distal first outwardly facing surface may have a maximum width greater than a maximum width of the distal second outwardly facing surface. At least one of the distal first, second, and third outwardly facing surfaces may have a proximally projecting edge forming a tip of a barb configured to engage tissue and inhibit rotational movement and inhibit axial movement of the distal head in a proximal direction. The device also comprises an arrowhead-shaped proximal head comprising a proximal end having a sharp proximal point and also comprising proximal first, second, and third outwardly facing side surfaces converging toward and intersecting at the proximal point. The proximal first outwardly facing surface may have a maximum width greater than a maximum width of the proximal second outwardly facing surface. At least one of the proximal first, second, and third outwardly facing surfaces may have a distally projecting edge forming a tip of a barb configured to engage tissue and inhibit rotational movement and inhibit axial movement of the proximal head in a distal direction. A rigid body extends between and connects the distal head and the proximal head. The body may have a rigidity sufficient to withstand bending loading applied by the phalanges. In yet additional embodiments, the present disclosure is directed to a kit including the intramedullary fixation device. In yet additional embodiments, the present disclosure is directed to methods for implanting the intramedullary fixation device.

In another exemplary aspect, the present disclosure is directed to an intramedullary fixation device used in bone fixation and stabilization on a patient. The device includes a longitudinally extending rigid body and a distal head disposed at a distal end of the body. The distal head includes a central core portion and a plurality of extending distal wings radially projecting from the central core portion, wherein the radially projecting distal wings are spaced asymmetrically about the central core portion. A proximal head is disposed at a proximal end of the body and is sized for insertion into an intramedullary canal of a phalanx of the patient. The proximal head includes a central core portion and a plurality of proximal wings extending radially outwardly from the central core portion.

In an exemplary aspect, the present disclosure is directed to an intramedullary fixation device used in bone fixation and stabilization on a patient. The device includes a longitudinally extending rigid body having a rigidity sufficient to withstand bending loading applied by the phalanges. The rigid body has a longitudinal axis extending through at a least a portion of the body. The device also includes a distal head disposed at a distal end of the body and sized for insertion into an intramedullary canal of a phalanx of the patient. The distal head has a central core portion and a plurality of extending distal wings radially projecting from the central core portion. The radially projecting distal wings are spaced asymmetrically or symmetrically about the central core portion. The device also includes a proximal head at a proximal end of the body that is sized for insertion into an intramedullary canal of a phalanx of the patient, the proximal head having central core portion and a plurality of proximal wings extending radially outwardly from the central core portion.

In an aspect, the distal head has a first maximum width and the proximal head has a second maximum width, the first maximum width being greater than the second maximum width. In an aspect, the distal head has a first longitudinal wing length and the proximal head has a second longitudinal wing length, the first longitudinal wing length being less than the second longitudinal wing length. In an aspect, the asymmetrically spaced, radially projecting distal wings form a T-shape. In an aspect, the device comprises a planar surface extending entirely across the transverse width of the distal head portion. In an aspect, at least one the proximal wings or the distal wings has a profile that is wedge-shaped. In an aspect, each proximal wing comprises an outer surface portion forming an outer perimeter surface, the outer surface portion comprising an outer perimeter surface portion and a curved leading surface portion, the curved leading surface portion curving from the outer perimeter surface portion and smoothly intersecting at the central core portion of the proximal head, each proximal wing also comprising a distally facing trailing surface portion substantially perpendicular to the longitudinal axis of the rigid body. In an aspect, each distal wing comprising an outer surface portion having an outer perimeter surface portion and a curved leading surface portion, the curved leading surface portion curving from the outer perimeter surface portion and smoothly intersecting at the central core portion of the distal head, each wing of the distal head also comprising a proximally facing trailing surface portion substantially perpendicular to the longitudinal axis of the rigid body.

In another exemplary aspect, the present disclosure is directed to an intramedullary fixation device used in bone fixation and stabilization on a patient. The device includes a longitudinally extending rigid body having a rigidity sufficient to withstand bending loading applied by the phalanges, the rigid body having a longitudinal axis extending through at a least a portion of the body. The device also includes a distal head disposed at a distal end of the body and sized for insertion into an intramedullary canal of a phalanx of the patient. The distal head has a central core portion and at least three radially extending distal wings radially projecting from the central core portion. Two of the wings form a planar surface extending entirely across the width of the distal head. The device also includes a proximal head at a proximal end of the body and sized for insertion into an intramedullary canal of a phalanx of the patient. The proximal head has a central core portion and a plurality of proximal wings extending radially outwardly from the central core portion.

In an aspect, the radially projecting distal wings are spaced asymmetrically about the central core portion. In an aspect, the distal head has a first maximum width and the proximal head has a second maximum width, the first maximum width being greater than the second maximum width. In an aspect, the distal head has a first longitudinal wing length and the proximal head has a second longitudinal wing length, the first longitudinal wing length being less than the second longitudinal wing length. In an aspect, the asymmetrically spaced, radially projecting distal wings form a T-shape. In an aspect, the device comprises a planar surface extending entirely across the transverse width of the distal head portion. In an aspect, at least one the proximal wings or the distal wings is wedge-shaped. In an aspect, each proximal wing comprises an outer surface portion forming an outer perimeter surface, the outer surface portion comprising an outer perimeter surface portion and a curved leading surface portion, the curved leading surface portion curving from the outer perimeter surface portion and smoothly intersecting at the central core portion of the proximal head, each proximal wing also comprising a distally facing trailing surface portion substantially perpendicular to the longitudinal axis of the rigid body. In an aspect, each distal wing comprising an outer surface portion having an outer perimeter surface portion and a curved leading surface portion, the curved leading surface portion curving from the outer perimeter surface portion and smoothly intersecting at the central core portion of the distal head, each wing of the distal head also comprising a proximally facing trailing surface portion substantially perpendicular to the longitudinal axis of the rigid body.

In one exemplary aspect, the present disclosure is directed to an intramedullary fixation device used in bone fixation and stabilization on a patient. The device includes a longitudinally extending rigid body and a distal head disposed at a distal end of the body. The distal head is sized for insertion into an intramedullary canal of a phalanx of the patient. The distal head has a central core portion and a plurality of extending distal wings radially projecting from the central core portion. A proximal head at a proximal end of the body is sized for insertion into an intramedullary canal of a phalanx of the patient. It has a central core portion and a plurality of proximal wings extending radially outwardly from the central core portion.

In an exemplary aspect, the present disclosure is directed to an intramedullary fixation device used in bone fixation and stabilization. The device includes an arrowhead-shaped distal head comprising a distal end having a distal tip, with the distal head having first, second, third, and fourth outwardly facing side surfaces forming a pyramidal shape. The first and third side surfaces may be opposed from each other and form a first angle, and the second and fourth side surfaces may be opposed from each other and form a second angle. The second angle is different than the first angle. Each of the first and third side surfaces have a proximally projecting edge forming a tip of a barb, where the barbs are configured to engage tissue and inhibit rotational movement and inhibit axial movement of the distal head in a proximal direction. The distal head has a first dimensional width measured between proximally projecting edges of the first and third side surfaces. The device also includes an arrowhead-shaped proximal head comprising a proximal end having a proximal tip. The proximal head has fifth, sixth, seventh, and eighth outwardly facing side surfaces. The fifth and seventh side surfaces may be opposed from each other and form a third angle, and the sixth and eighth side surfaces may be opposed from each other and form a fourth angle. The third angle is different than the fourth angle. Each of the fifth and seventh side surfaces has a distally projecting edge. The proximal head includes a trailing edge surface intersecting the distally projecting edge of the fifth and seventh side surfaces, with the trailing edge surface extending in a direction substantially perpendicular to a longitudinal direction of the proximal head and intersecting with a neck region. The proximal head has a second dimensional width measured between distally projecting edges of the fifth and seventh side surfaces, with the second dimensional width being within the range of about 1.3-1.5 times the first dimensional width. A rigid body extends between and connects the distal head and the proximal head. The rigid body has a neck region joined to the trailing edge surface of the proximal head in a manner that the trailing edge surface is perpendicular to a longitudinal axis of the body. The body has a rigidity sufficient to withstand bending loading applied by the phalanges.

In an aspect, the first angle is smaller than the third angle. In an aspect, the first angle is smaller than the second angle and the third angle is smaller than the fourth angle. In an aspect, the second and fourth side surfaces include proximal ends that relatively smoothly transition to the body. In an aspect, the distal head comprises a first undercut and a second undercut, the first and second undercuts respectively cooperating with the first and third side surfaces to form the barbs, each of the first and second undercuts having a depth such that the barb tips are disposed proximal of the respective undercut. In an aspect, the body comprises a main portion, a distal neck portion, and a proximal neck portion, the distal and proximal neck portions having a cross-sectional area smaller than a cross-section area of the main portion.

In an exemplary aspect, the present disclosure is directed to an intramedullary fixation device used in bone fixation and stabilization on a patient that includes a longitudinally extending rigid body having a rigidity sufficient to withstand bending loading applied by the phalanges, with the rigid body having a longitudinal axis extending through at a least a portion of the body. A distal head is disposed at a distal end of the body and sized for insertion into an intramedullary canal of a phalanx of the patient. The distal head has a central core portion and a plurality of extending distal wings radially projecting from the central core portion. Each distal wing comprises an outer surface portion having an outer perimeter surface portion and a curved leading surface portion. The curved leading surface portion curves from the outer perimeter surface portion and smoothly intersects at the central core portion of the distal head. Each wing of the distal head also comprises a proximally facing trailing surface portion substantially perpendicular to the longitudinal axis of the rigid body. The distal head has a first maximum diameter defined by the outer perimeter surface portion of the distal wings and a first wing length. The device also includes a proximal head at a proximal end of the body sized for insertion into an intramedullary canal of a phalanx of the patient. The proximal head has a central core portion and a plurality of proximal wings extending radially outwardly from the central core portion. Each proximal wing comprises an outer surface portion having an outer perimeter surface portion and a curved leading surface portion. The curved leading surface portion curves from the outer perimeter surface portion and smoothly intersects at the central core portion of the proximal head. Each proximal wing also comprises a distally facing trailing surface portion substantially perpendicular to the longitudinal axis of the rigid body. The proximal head has a second maximum diameter defined by the outer perimeter surface portion of the distal wings and a second wing length, wherein the first maximum diameter of the distal wings is less than the second maximum diameter of the proximal wings, and wherein first wing length of the distal wings is greater than the second wing length of the proximal wings.

In an aspect, at least one of the proximal wings is wedge-shaped, such that the trailing surface portion has a thickness greater than at the curved leading surface portion. In an aspect, the body includes a central region and end regions, with the central region having a cross-section width greater than the cross-sectional width of the end regions. In an aspect, the central region extends between about 40 and 70% of the length of the body. In an aspect, the body comprises a narrow region adjacent one of the proximal and distal heads, the narrow region extending from said one of the proximal and distal heads more than 20% of the length of the body. In an aspect, the narrow region is adjacent the proximal head. In an aspect, the distal head comprises a leading nub disposed on the distal end of the distal head. In an aspect, the device comprises a fixation-promoting coating disposed on the body. In an aspect, the body includes a plantar grade bend in a range of about 5 to 15 degrees. In an aspect, the central core has a cross-sectional size smaller than a cross-sectional size of the body. In an aspect, the body is formed of two rigid elements joined together. In an aspect, the device has an overall length, and the proximal and distal heads form not more than about 30% of the overall length. In an aspect, the central core portion on the distal head smoothly connects adjacent wings without edges or corners. In an aspect, the wings form a cruciate or plus shape when viewed from an end. In an aspect, the device comprises more than four distal wings and more than four proximal wings. In an aspect, the plurality of distal wings is symmetrically disposed about the distal head and wherein the plurality of proximal wings is symmetrically disposed about the proximal head.

In yet another exemplary aspect, the present disclosure is directed to an intramedullary fixation device used in bone fixation and stabilization on a patient that includes a longitudinally extending rigid body having a rigidity sufficient to withstand bending loading applied by the phalanges, with the rigid body having a longitudinal axis extending through at a least a portion of the body. The device also includes a distal head disposed at a distal end of the body and sized for insertion into an intramedullary canal of a phalanx of the patient. The distal head has a central core portion and a plurality of extending distal wings radially projecting from the central core portion. The central core portion has an outer surface smoothly intersecting with the adjacent distal wings and including a leading nub. Each distal wing comprises an outer surface portion having an outer perimeter surface portion and a curved leading surface portion, where the curved leading surface portion curves from the outer perimeter surface portion and smoothly intersects at the central core portion of the distal head. Each wing of the distal head also comprises a proximally facing trailing surface portion substantially perpendicular to the longitudinal axis of the rigid body. The distal head has a first maximum diameter defined by the outer perimeter surface portion of the distal wings and a first wing length. The device also includes a proximal head at a proximal end of the body sized for insertion into an intramedullary canal of a phalanx of the patient. The proximal head has central core portion and a plurality of proximal wings extending radially outwardly from the central core portion. The central core portion has an outer surface smoothly intersecting with the adjacent distal wings and including a leading nub. Each proximal wing comprises an outer surface portion having an outer perimeter surface portion and a curved leading surface portion, where the curved leading surface portion curves from the outer perimeter surface portion and smoothly intersects at the central core portion of the proximal head. Each proximal wing also comprises a distally facing trailing surface portion substantially perpendicular to the longitudinal axis of the rigid body. The proximal head has a second maximum diameter defined by the outer perimeter surface portion of the distal wings and a second wing length, wherein the first maximum diameter of the distal wings is less than the second maximum diameter of the proximal wings, and wherein first wing length of the distal wings is greater than the second wing length of the proximal wings, wherein the device has an overall length, and the proximal and distal heads form not more than about 25% of the overall length.

In an aspect, at least one of the proximal wings and is wedge-shaped, such that the trailing surface portion has a thickness greater than at the curved leading surface portion. In an aspect, the body includes a central region and end regions, with the central region having a cross-section width greater than the cross-sectional width of the end regions. In an aspect, the central region extends between about 40% and 70% of the length of the body. In an aspect, the body comprises a narrow region adjacent one of the proximal and distal heads, the narrow region extending from said one of the proximal and distal heads more than 20% of the length of the body. In an aspect, the narrow region is adjacent the proximal head.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

FIGS. 7 and 7A are illustrations of an exemplary reamer surgical instrument usable for implantation of an intramedullary fixation device in accordance with one aspect of the present disclosure.

FIGS. 8 and 8A are illustrations of an exemplary broach surgical instrument usable for implantation of an intramedullary fixation device in accordance with one aspect of the present disclosure.

FIGS. 14-18 are illustrations of another exemplary intramedullary fixation device in accordance with one aspect of the present disclosure.

FIGS. 26-30 are illustrations of another exemplary intramedullary fixation device in accordance with one aspect of the present disclosure.

FIG. 34 is an illustration of the exemplary intramedullary fixation device of FIG. 1 in accordance with one aspect of the present disclosure.

FIG. 35 is an illustration of a side view of the exemplary intramedullary fixation device of FIG. 2 in accordance with one aspect of the present disclosure.

FIGS. 37-41 are illustrations of another exemplary intramedullary fixation device in accordance with one aspect of the present disclosure.

FIGS. 44-48 are illustrations of another exemplary intramedullary fixation device in accordance with one aspect of the present disclosure.

DETAILED DESCRIPTION

Figure 1:
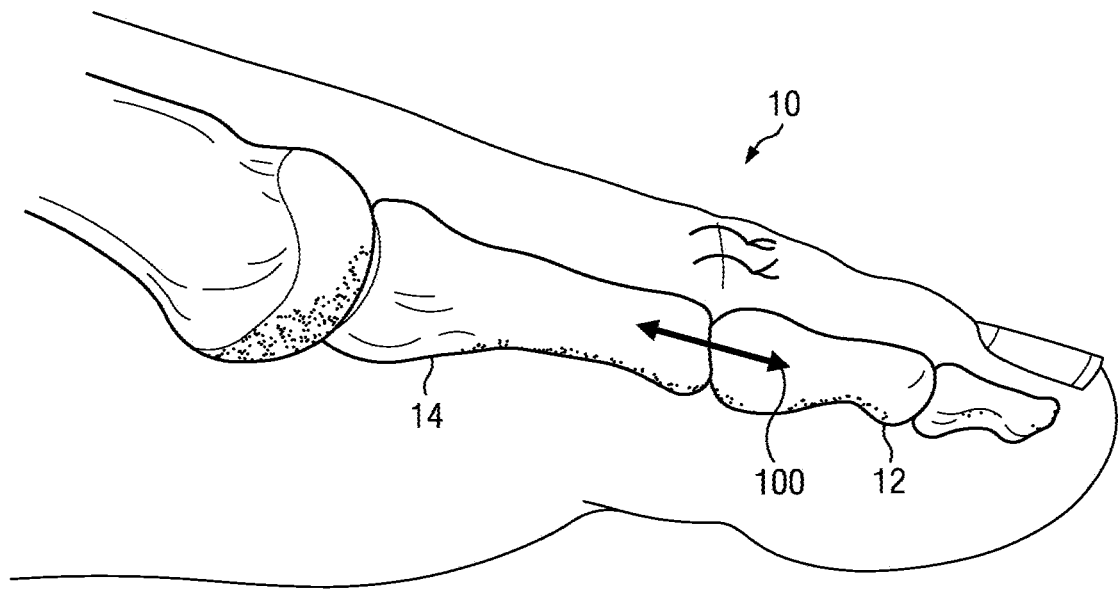
FIG. 1 is an illustration of an exemplary intramedullary fixation device disposed between and within adjacent phalanges of a toe of a patient in accordance with one aspect of the present disclosure.

The following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present invention relates to an intramedullary fixation device used for bone fixation and stabilization of toes and fingers across fusion or fracture sites, and treat deformities, including for example, hammertoe deformities. The intramedullary fixation device includes a unique arrow design on both its proximal and distal ends. It is arranged to be completely intramedullary when implanted with no parts of the device exposed outside the skin. Further, it is arranged to resist the rotational and pull-out forces affecting the lesser toes. Its particular design shape may help it maintain the initial compression applied at insertion.

In addition, because of its convenient dual locking design, the intramedullary fixation device enables health care providers to perform implantation procedures faster and with less effort than prior techniques, such as those using external wires, such as K-wires. For example, it may require little or no bone removal when preparing for device insertion, potentially decreasing trauma and reducing recovery times. Further, the intramedullary fixation devices disclosed herein may remain permanently implanted. Accordingly, there is no need to schedule an additional procedure to remove this device as is necessary with temporary fixation devices, such as is required with K-wire fixation. As such, the intramedullary fixation devices disclosed herein may provide a more comfortable recovery, a lower incidence of infections, and the avoidance of that additional and often very uncomfortable procedure to remove the K-wire implant. Further, unlike the K-wire implants, the arrow designs at each end of the implant lock into bone reducing osseous movement or rotation.

FIG. 1 shows an exemplary toe 10 having an intermediate phalanx 12 and a proximal phalanx 14. In this example, the toe 10 has been surgically treated to correct a deformity such as hammertoe as discussed above. Accordingly, the toe includes an implanted intramedullary fixation device 100 disposed therein in accordance with an exemplary aspect of the present disclosure. In this example, the device 100 extends between and is implanted within the intermediate and proximal phalanges 12, 14. It is described in detail below.

Figure 2:
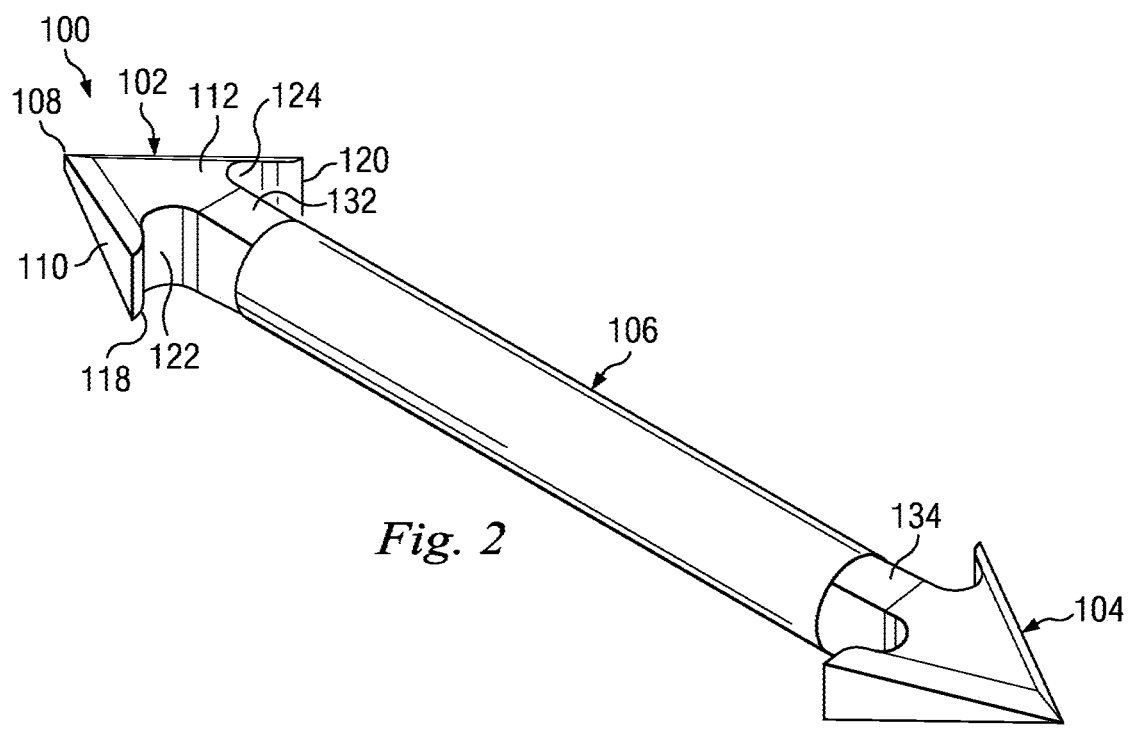
FIG. 2 is an illustration of the exemplary intramedullary fixation device of FIG. 1 in accordance with one aspect of the present disclosure.
Figure 3:
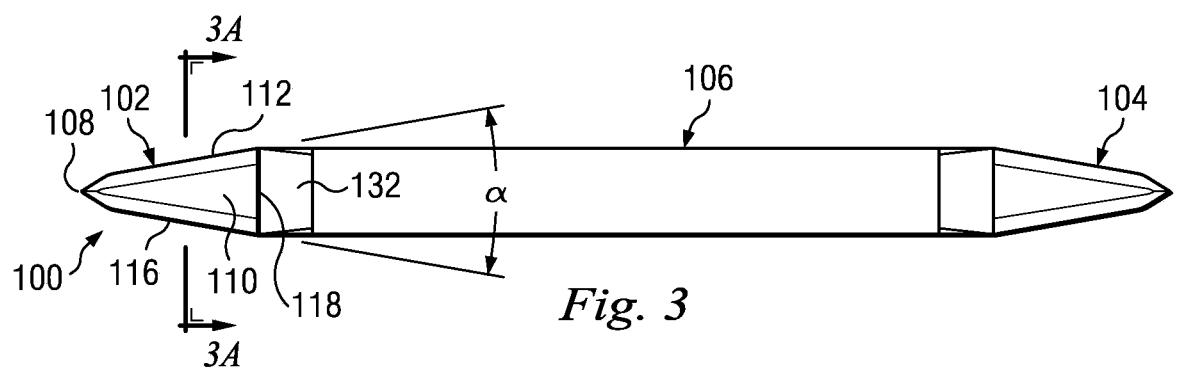
FIG. 3 is an illustration of a side view of the exemplary intramedullary fixation device of FIG. 2 in accordance with one aspect of the present disclosure.
Figure 4:
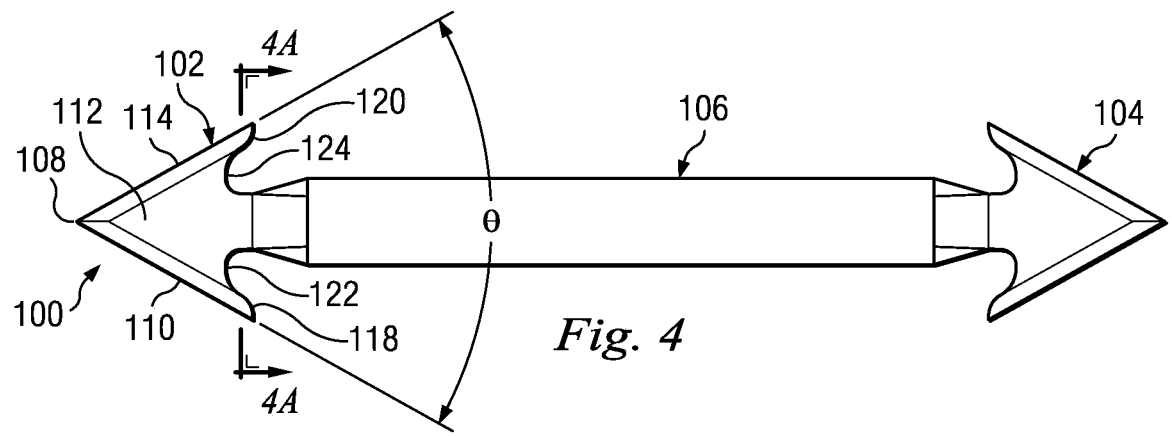
FIG. 4 is an illustration of another side view of the exemplary intramedullary fixation device of FIG. 2 rotated 90 degrees from the side view of FIG. 3.

FIGS. 2-4 show one exemplary embodiment of the device 100 of the present application. The device 100 is designed with a three-dimensionally configured arrow at each end and includes a first head 102, a second head 104, and a body 106 extending between the first and second heads 102, 104. As will become apparent from the below description, the individual components of the device 100 work in conjunction with one another to stabilize bone during arthrodesis procedures and across fractures. For reference, this disclosure refers to the first head 102 as a distal head and the second head 104 as the proximal head.

The distal head 102 is formed as a three dimensional arrowhead that is sized for placement in an intramedullary canal of a patient. It is configured so that edges of the arrowhead grasp the bone in the medullary canal as it is inserted, stabilizing the arthrodesis or fusion site during the osseous union. In this exemplary embodiment, the distal head 102 is formed as a distal end having a distal-most point 108. The distal-most point 108 leads the device 100 down the reamed or broached insertion channel to its final implantation site during insertion. In this example, the distal-most point 108 is a sharp point arranged to glide through tissue within the intramedullary canal to ease insertion. The sharp point 108 also may reduce trauma occurring due to a ripping or tearing effect that may occur with blunt or rounded tips. Other configurations of the arrowhead's tip may result in successful insertion based on preparation of the insertion site.

First, second, third, and fourth outer facing surfaces 110, 112, 114, 116 intersect at and extend from the distal most point 108 in the proximal direction, forming a four-sided pyramidal shape. Although shown as having four outer facing surfaces, some embodiments include greater or fewer outer facing side surfaces. In the example shown, opposing surfaces angle away from each other to define a leading angle. For example, the opposing first and third outer facing surfaces 110, 114 define an angle 0 of the arrowhead shaped distal head 102. In some examples, the angle 0 is in the range of about 30 degrees to about 90 degrees. In other examples, the angle 0 is in the range of about 50 to 70 degrees, and in some embodiments, the angle is around 60 degrees. In a similar manner, the opposing second and fourth outer facing surfaces 112, 116 of the arrowhead shaped distal head 102 form an angle a. In the example shown, the angle a is smaller than the angle O. The angle a may be selected to be within the range of about 10-40 degrees, and in some embodiments, is in the range of about 1525 degrees. In some examples, the angle a is about 19 degrees. The multiple angles described on the distal head may vary based on the size and strength of bone in which the device is to be implanted.

Figure 3A:
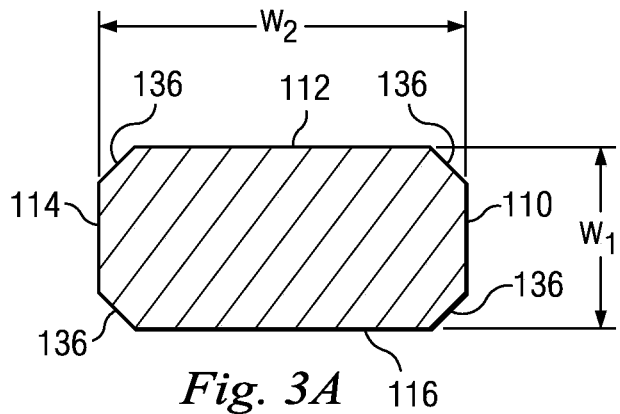
FIG. 3A is an illustration of a cross-sectional view along lines 3A in FIG. 3 through a head of the intramedullary fixation device of FIG. 3.

Because of the different angles between the opposing first and third surfaces 110, 114 and the opposing second and fourth surfaces 112, 116, the width of the distal head 102 differs from side to side. This is best seen in FIG. 3A, showing a cross-sectional view of the distal head 102 taken through the section 3A in FIG. 3. For example, FIG. 3A shows a width w1 of the first and third outer facing surfaces 110, 114 being less than a width w2 of the outer facing surfaces 112, 116. This differing width increases resistance to rotation that may occur if the device 100 were cylindrical or to a lesser extent substantially square, although such embodiments are contemplated. Further, the differing width may permit an implanted device to be removed, rotated 90 degrees and implanted again while still providing satisfactory anchoring.

Returning to FIG. 3, the distal head 102 may be sized to have a transverse width w3 greater than a longitudinal length L. The transverse width w3 may be sized in the range 2-6 mm and the longitudinal length L may be sized in the range of about 1.5-5.5 mm. In one example, the transverse width w3 is around 3.5 mm and the longitudinal length L is about 3 mm. Other sizes however, both larger and smaller, are contemplated, and in one example, the width and the length are substantially equal.

In the example shown, the distal head 102 includes two proximally projecting barbs 118, 120. These barbs are configured to engage tissue within the intramedullary canal and resist movement and migration and/or axial displacement within the canal once they have been inserted into the canal. As can be seen, these barbs 118, 120 are formed by edges of respective outer facing surfaces 110, 114 and because of the pyramidal shape of the distal head, the edges lie in substantially parallel lines.

Figure 4A:
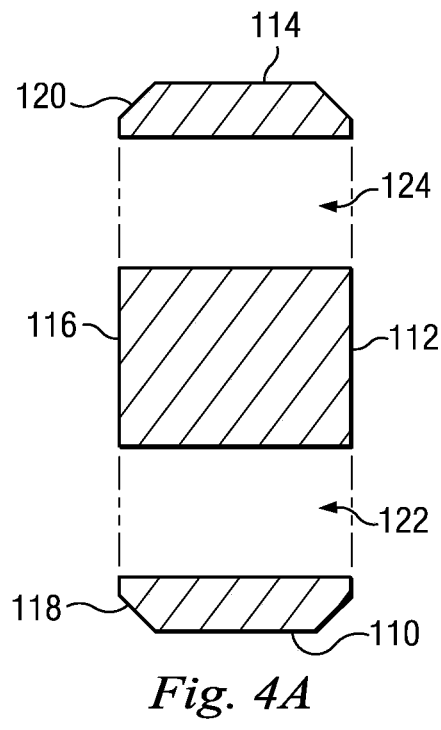
FIG. 4A is an illustration of a cross-sectional view along lines 4A in FIG. 4 through a head of the intramedullary fixation device of FIG. 4.

Inner surfaces of the barbs 118, 120 are formed by first and second undercuts 122, 124 disposed respectively between tips of the barbs 118, 120 and the body 106. In this example, the undercuts are formed so that they cut into the body in a direction and at a location distal of proximal tips of the barbs 118, 120. This is shown also in the cross-sectional view of FIG. 4A, taken along lines 4A in FIG. 4. In this example, the undercuts 122, 124 are formed by arcing surfaces. Because of the curvature, the arcing surfaces have a distal peak that is distal of the tips of the barbs 118, 120 themselves. The undercut surfaces 122, 124 merge with the body 106 to provide greater pull-out resistance. The shape shown, with its arcing surfaces, may expose a larger surface area to cancellous bone, thereby increasing the resistance to the pull out forces as compared to a straight surface. The undercuts themselves provides space that accommodates bony ingrowth to provide additional pull-out resistance and further stabilize the implant during healing and fusion. While in the example shown, the barbs are substantially rigid or inflexible, in other embodiments, the undercut may also serve to allow the barbs to flex when the implant becomes lodged in hard cortical bone. In some embodiments, the undercuts are formed with surface profiles or shapes other than proximal arcs. For example, some embodiments have undercuts that are formed with substantially flat surfaces disposed distal of tips of the barbs 118, 120. These may be transverse to the longitudinal direction of the device 100. Other embodiments have undercuts that project deeply into the distal head 102, substantially parallel to the angled outer facing surfaces 110, 114. These may be suitable when less pull-out strength is needed. Because there is only one barb 118, 120 along each side of the device 100, insertion may result in less tissue disruption than an arrow having multiple barbs or having a several points of equal maximum width. As a result of lower trauma, the tissue itself may be more intact for securing the barbs and resisting removal or axial displacement from the intramedullary canal.

The body 106 extends between and connects the distal head 102 and the proximal head 104. It is a one-piece rigid element structurally configured to withstand loading applied across the joint or fracture being supported. It includes a main body portion 130 and necks 132, 134 at either end leading to the distal and proximal heads 102, 104. As can be seen, the main body portion 130 has a diameter larger than that of the necks 132, 134. For the reasons explained below, the larger body portion 130 may be easier to grasp and secure because it has a larger perimeter surface area, while the necks 132, 134 may be sized to permit additional tissue placement and tissue growth immediately adjacent the undercut surfaces 122, 124 of the distal and proximal heads 102, 104. This may result in more secure and lasting anchoring. Thus, this structural arrangement may provide space for extra tissue to grow behind the arrowhead to aid in fixation, while still providing a large gripping surface on the body 106. In the embodiment shown, the diameter of the main body 130 is in the range of about 1-3 mm, and preferably has a diameter around 1.5 mm. Both larger and smaller diameters are contemplated. In the example shown, the main body 130 is cylindrically shaped, which provides consistent strength characteristics through the length of the implant. Further, the diameter is substantially consistent along its length in order to permit the implant to be gripped with insertion tools at any point along the main body in order to best fit the anatomic variations of the phalanges. Because the main body has a round profile, the body may be gripped with an insertion tool at any desired rotational orientation relative to the tool, permitting the health care provider to orient and penetrate the desired bone location. The length of the body 106 is selected so that the opposing distal and proximal heads lie at the desired location within the phalanx when inserted in the bone. Accordingly, without limitation, in some embodiments, the length of the device 100 is within a range of about 10-50 mm, and the body 106 has a length of 7-44 mm. In one example, the length of the body 106 is in the range of about 7-15 mm, and in one example, has a length of about 13 mm. Both larger and smaller bodies are contemplated.

Still referring to these figures, the second and fourth outer facing surfaces 112, 116 are angled and intersect with the body 106 at the neck 132. In some examples, the second and fourth outer facing surfaces 112, 114 may smoothly transition to the neck and in other examples, the second and fourth outer facing surfaces 112, 114 meet the neck 132 at an intersecting angle. In some examples, the neck 132 is formed with a rounded perimeter having a diameter substantially similar to the distance between the proximal ends of the second and fourth outer facing surfaces 112, 114.

In the exemplary embodiment shown, each of the edges joining adjacent outer facing surfaces 110, 112, 114, 116 is chamfered or rounded, resulting in less sharp edges. This may be best seen in the cross-sectional view shown in FIG.

3A. In the example shown, the distal head 102 includes chamfers 136 formed at 45 degree angles relative to the outer facing surfaces 110, 112, 114, and 116. Other embodiments however, include chamfers at other angles or rounds with a radius that provides smooth transition from one outer facing surface to another. As such, in some examples, tissue may be more likely to be deflected and pushed aside during advancement of the distal head into the tissue than to be cut by what might otherwise be sharp 90 degree edges between adjacent outer facing surfaces 110, 112, 114, 116. This may result in better purchase because tissue may be better left intact during insertion of the device 100.

The second or proximal head 104 is, in the example shown, substantially similar to the distal head 102, but extends from the body 106 in the opposing direction. For clarity and to reduce duplication, the description above of the proximal head is not repeated here with the understanding that the description above applies equally to the proximal head 104. The distal and proximal heads, due to their shape and opposing configuration, resist migration, pullout, and rotation.

The proximal and distal heads 102, 104 and the body 106 are, in the example shown, equivalent to one another having substantially the same size and configuration. In some examples however, the size or configuration of the distal and proximal heads are different. For example, the angle a between the second and fourth outer facing surfaces on the proximal head may be larger or smaller than the angle between the second and fourth outer facing surfaces on the distal head. Likewise, the angle 0 between the first and third outer facing surfaces on the proximal head may be larger or smaller than the angle between the second and fourth outer facing surfaces on the distal head. In some examples, the distal and proximal heads are merely scaled in size relative to each other. In one example, the transverse widths w3 of the distal head and the proximal head are substantially equally sized at about 3.5 mm and the longitudinal lengths L are equally sized at about 3.0 mm. In another example, the transverse width w3 of the proximal head is about 3.5 mm, and the transverse width of the distal head is selected as one of about 2.0 mm, about 2.5 mm, and about 3.0 mm. In another example, the transverse width of the proximal head is selected to be about 4.0 mm, and the transverse width of the distal head is selected to be about one of about 2.0 mm, about 3.0 mm, and about 3.5 mm. The size of the distal and proximal heads may be selected based on their intended utility, including whether the device is intended for implantation in a toe phalanx or a finger phalanx or across a fracture, for example. Because not all medullary canals have the same diameter, a health care provider may select an implant to achieve a desired fit. For example, a health care provider may accommodate situations where the proximal phalanx has a larger medullary canal than the medullary canal of the intermediate phalanx. Although described as though the proximal head is larger than the distal head, in some examples the distal head may be sized larger than the proximal head by any of the dimensions discussed above. Although particular maximum widths are provided as examples here, the sizes may be dimensioned larger or smaller than those indicated, and sizes may be offered in any desired size increment. Further, the angles may differ based on the size or diameter of bones to be treated. Accordingly, the device 100 may be sized to fit a wide range of anatomies, as well as different joints of the phalanges.

The device 100 may be sterilized and may be formed of biocompatible materials, including stainless steels and titanium as well as non-metallic materials, such as composites, polymers, and bioresorbables. In one example the device is formed of 316L (F138) stainless steel. In some examples, the device 100 is manufactured from a solid bar by a mechanical metal removal process, such as machining. After machining, the product may be passivated per ASTM A967-96 to remove any surface contaminants. It may then be electropolished to improve the surface finish and edge finish and may be laser marked for identification. Some designs may lend themselves to a metal injection molding process.

Figure 5:
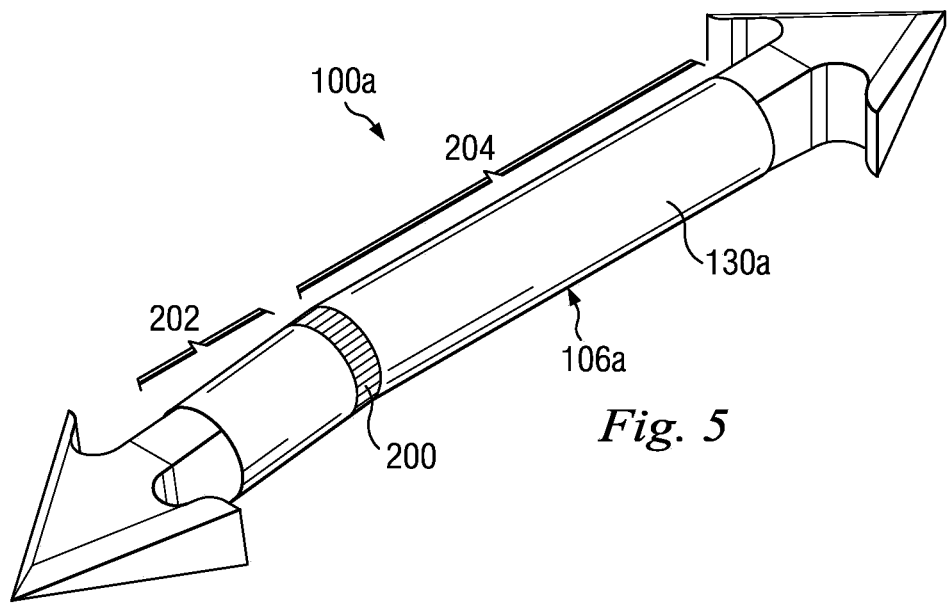
FIG. 5 is an illustration of another exemplary intramedullary fixation device in accordance with one aspect of the present disclosure.

FIG. 5 shows another embodiment of the device 100. For reference the device in FIG. 5 will be referenced by the numeral 100*a*. Since many of the features are the same as the device 100 in FIGS. 2-4, only the differences will be described in detail. The device 100*a* includes a body 106*a* formed of a main body portion 130*a* having a plantar grade bend 200. In this example, the bend 200 is a 10 degree plantar grade bend. Different embodiments include a bend that may be selected in the range of about 5-25 degrees. In some examples, the bend is selected to be about a 15 degree bend, while yet other embodiments the bend is selected to be about a 5 degree bend. The bend divides the body portion 130*a* into a first portion 202 and a second portion 204. The first and second portions 202, 204 respectively define first and second longitudinal axes that intersect at the bend 200. In some examples, the bend 200 is disposed at a location within a range of about 40-80% of the length of the body portion 130*a*. In some examples, the bend is within a range of about 50-70% of the length of the body portion 130*a*. In some examples, the bend is at about 60% of the length of the body portion 130*a*. In other examples however, the bend 200 is disposed at other locations. Although shown with a 10 degree bend, other embodiments include a bend angled within a range of about 5-30 degrees, and in some examples, angled within a range of about 7-15 degrees. In some examples, the longer segment is particularly suited for accommodating the proximal phalanx and the shorter segment is particularly suited for accommodating the intermediate segment. Like the embodiments described above, the device 100*a* is formed of a single solid, monolith material. Accordingly, there are no seams, welds, joints, or other stress introducers. Whether to use a straight or bent configuration will depend on the deformity. The bent device 100*a* provides a similar bend to the bone structure at the fusion/fracture site.

Figure 6:
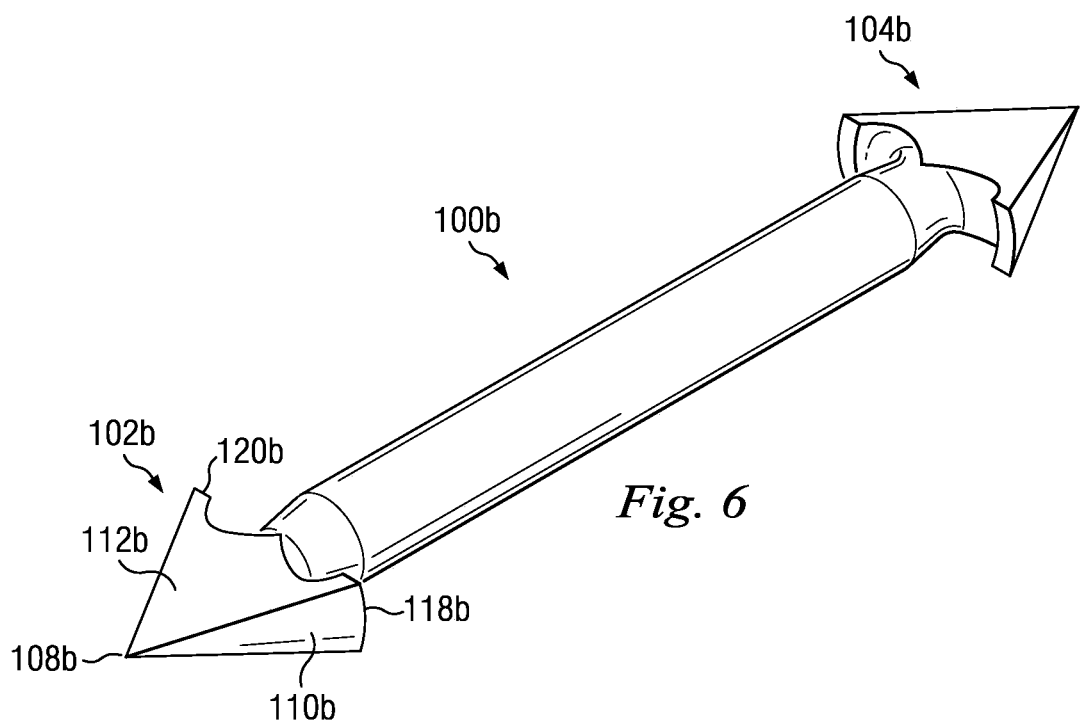
FIG. 6 is an illustration of another exemplary intramedullary fixation device in accordance with one aspect of the present disclosure.

FIG. 6 shows another embodiment of the device 100. For reference the device in FIG. 6 will be referenced by the numeral 100*b*. Since many of the features are the same as the device 100 in FIGS. 2-4, only differences will be described in detail with the understanding that other details and much of the description above applies equally to the device 100*b*. The device 100*b* includes first and second heads 102*b,* 104*b*. Like the heads described with reference to FIGS. 2-4, the first and second heads 102, 104 are three dimensional arrowheads.

For convenience, only the first head 102*b,* referred to as the distal head, will be described in detail. The distal head 102*b* includes a sharp distal-most point 108*b*. First, second, third, and fourth outer facing surfaces extend from the distal most point 108*b* in the proximal direction, forming a pyramidal shape. In FIG. 6, only two outer facing surfaces 110*b,* 112*b* of the four outer facing surfaces are shown. It is understood that the opposing, non-visible surfaces are substantially identical to the surfaces 110*b,* 112*b* shown. In this embodiment however, the outer facing surface 110*b* and its opposing surface are not entirely planar, but are shaped slightly convex with a large radius such that the outer facing surface 110*b* arcs between the adjacent substantially planar side surface 112*b* and the outer facing surface opposing surface 112*b*. Because of this, the barbs 118*b*, 120*c* also include a slightly arched or rounded shape. Here, the radius of the arc is sized larger than a width of or diameter of the implant itself.

Intersections of adjacent outer facing surfaces form edges that, in this example, are not chamfered or rounded. However, because of the slightly convex surface shape of at least two of the outer facing surfaces, the edges in this example still do not form true right angles, but form angles less than 90 degrees. It should be noted that 90 degree angles are also contemplated.

Figure 9:
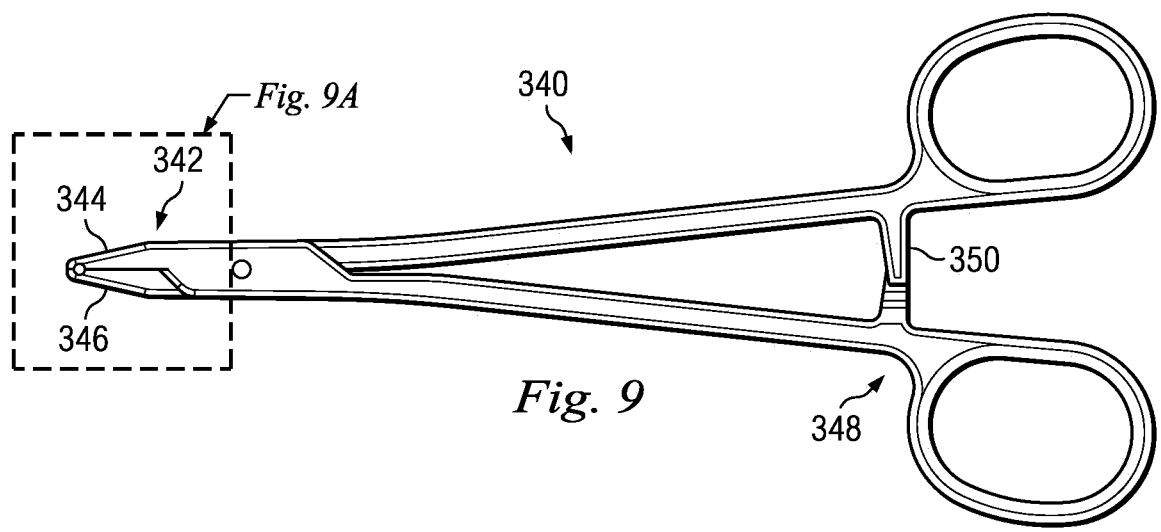
FIGS. 9 and 9A are illustrations of an exemplary insertion tool surgical instrument usable for implantation of an intramedullary fixation device in accordance with one aspect of the present disclosure.
Figure 9A:
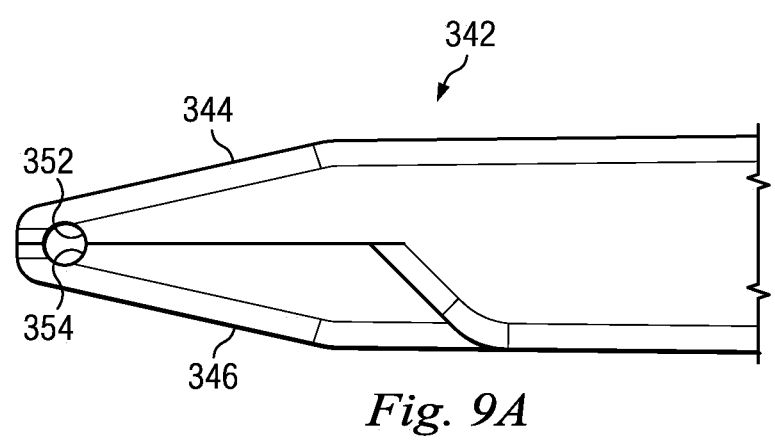

FIGS. 7-9 show surgical instruments that may be used to implant the devices described above. FIGS. 7 and 7A show a reamer 300, FIGS. 8 and 8A show a broach 320, and FIGS. 9 and 9A show insertion forceps 340.

Turning first to FIG. 7, the reamer 300 may be formed of a length of stainless steel wire having a diameter selected to penetrate and fit within and create pilot holes in intramedullary canals of toe or finger phalanges without removing bone. In one embodiment, the reamer 300 may have a diameter of about 1.6 mm. The reamer 300 may include a smooth trocar tip 302 configured to create a pilot hole without removing bone. In some examples, the reamer 300 includes markings 304 that serve as a depth gauge when reaming intramedullary canals. FIG. 7A shows the tip 302 in greater detail with laser markings 304 spaced, for example, at increments of 5 mm. Other embodiments include markings at different intervals, while yet other embodiments include a single marking indicating a pre-established depth. Some embodiments do not include any markings at all and the surgeon estimates the depth of the reamer 300.

FIG. 8 shows the broach 320 in greater detail. The broach is sized and configured for insertion into the pilot holes created by the reamer 300 to prepare the pilot hole for insertion of the device 100. Here, the broach 320 includes a handle 322 and a broach tool 324. In some examples, the diameter of the broach tool 324 is double the diameter of the reamer 300. The broach tool diameter may be, for example, selected to be within a range of about 1.5-5.0 mm. In other examples, the diameter is selected to be within a range of about 2.5-3.5 mm. In some examples, the broach tool 324 is sized with a diameter of about 3.2 mm. Diameters larger and smaller are contemplated. In the example shown, the broach tool 324 includes a pointed conical tip 326 having an angle that matches the greatest angle of the distal and proximal heads 102, 104 of the device 100. For example, if the device 100 includes first and third outwardly facing surfaces 110, 114 forming an angle 0 of, for example, 60 degrees, then the angle formed by sides of the conical tip 326 of the broach tool 324 may also be angled at 60 degrees. In other examples, the tip angle may be vary from the greatest angle of the distal and proximal heads, and may, for example, be selected to match the angle a formed by the second and fourth outer facing surfaces 112, 116. In other embodiments, the tip angle is larger or smaller than the angles of the outer facings surfaces.

FIG. 8A shows a part of the broach tool 324 in greater detail. In some examples, the broach tool 324 includes markings 328 that serve as a depth gauge when enlarging the pilot hole in the intramedullary canals. In this example, the laser markings 328 are spaced, for example, at increments of 5 mm. Other embodiments include markings at different intervals, while yet other embodiments include a single marking indicating a pre-established depth. Some embodiments do not include any markings at all and the surgeon estimates the depth of the broach tool 324. In the example shown, the broach tool 324 includes a sharp point and blade edges in order to penetrate the hard subcondral bone lying just beneath the cartilagenous surfaces. In a similar way, the sharp point and blades facilitate penetration of hard sclerotic bone. The broach shaft profile then rapidly increases in diameter to a profile more closely approximating that of the three dimensional arrow in order to facilitate the insertion of the definitive implant. The broach width is sized in relation to the implant to provide the proper balance between ease of insertion and resistance to rotational and pull-out forces. In some examples, this value ranges between 70% and 85% of the implant width and in one embodiment is about 77% of the implant width.

FIG. 9 shows the insertion forceps 340 in greater detail. The insertion forceps 340 have a grasping end 342 formed of first and second nose pieces 344, 346 pivotably connected in a manner to close upon and grip the device 100 and have a gripping end 348 with a locking mechanism 350 that secures the forceps 310 in a clamping position. As shown in FIG. 9A, each nose piece 344, 346 includes a transverse semicircular recess 352, 354 formed therein, aligned with each other when the nose pieces 344, 346 are adjacent each other. The recesses 352, 354 are formed in a manner permitting frictional engagement about the body 106 of the device 100 to secure it against both rotational and axial displacement relative to the insertion forceps 340. In the example shown, the recesses are round to match the cylindrical shape of the body 106 of the device 100. Because of the cylindrical shape of the body 106, the insertion forceps 340 can be oriented a full 360° in relation to the arrowhead tip to accommodate surgeon preference or anatomical variations. The radius dimension is determined based on the diameter of the body 106 in order to properly mate with the body 106. In some examples, the diameter formed by the two opposing recesses is within a range of about 5-15% smaller than the diameter of the body 106, thereby ensuring a secure grip on the device 100. In one example, the diameter of the body 106 is about 1.50 mm, then the recesses 352, 354 may each have a radius of 0.70 mm, together forming a diameter of 1.4 mm. In other examples, the radius is sized to substantially match that of the body 106. Both larger and smaller recesses are contemplated. It is to be noted that the larger the diameter of the body 106, the greater the surface area that is in contact with the insertion forceps, increasing frictional resistance. Therefore, a relatively large diameter of the body 106 may be desirable, resulting in a matching relatively large diameter of the recesses 352, 354. During use, the insertion forceps 340 can be used to create a positive stop that prevents the implant from inadvertently being inserted to a greater depth than desired. In addition, it can create a visual representation of the depth to which the surgeon desires to place the implant. Further, it is configured in a manner providing a safe surface upon which to strike should the implant need additional force to progress down the reamed intramedullary canal.

In some examples, the device 100 is provided as a kit with one or more of the instruments described above. One exemplary kit includes a device 100 as described above, with the reamer 300, the broach 320, and the insertion forceps 340. Another exemplary kit includes both the device 100 and the device 100*a*, along with the reamer 300, the broach 320, and the insertion forceps 340. Other exemplary kits include only one of the instruments with one or more of the devices 100, 100*a*. In one example, the kit includes a sterilized device 100, 100*a* and sterilized, single use instruments including one or more of the reamer 300, the broach 320, and the insertion forceps 340. In another example, the kit includes a sterilized device 100, 100a, and multiple use instruments including one or more of the reamer 300, the broach 320, and the insertion forceps 340. Some kit embodiments include a plurality of devices 100, 100a, with the instruments. In one example, a kit includes six devices and one set of instruments. In one example, the instruments are provided in an autoclavable tray (not shown) for sterilization. Other kits and arrangements are also contemplated.

Figure 10:
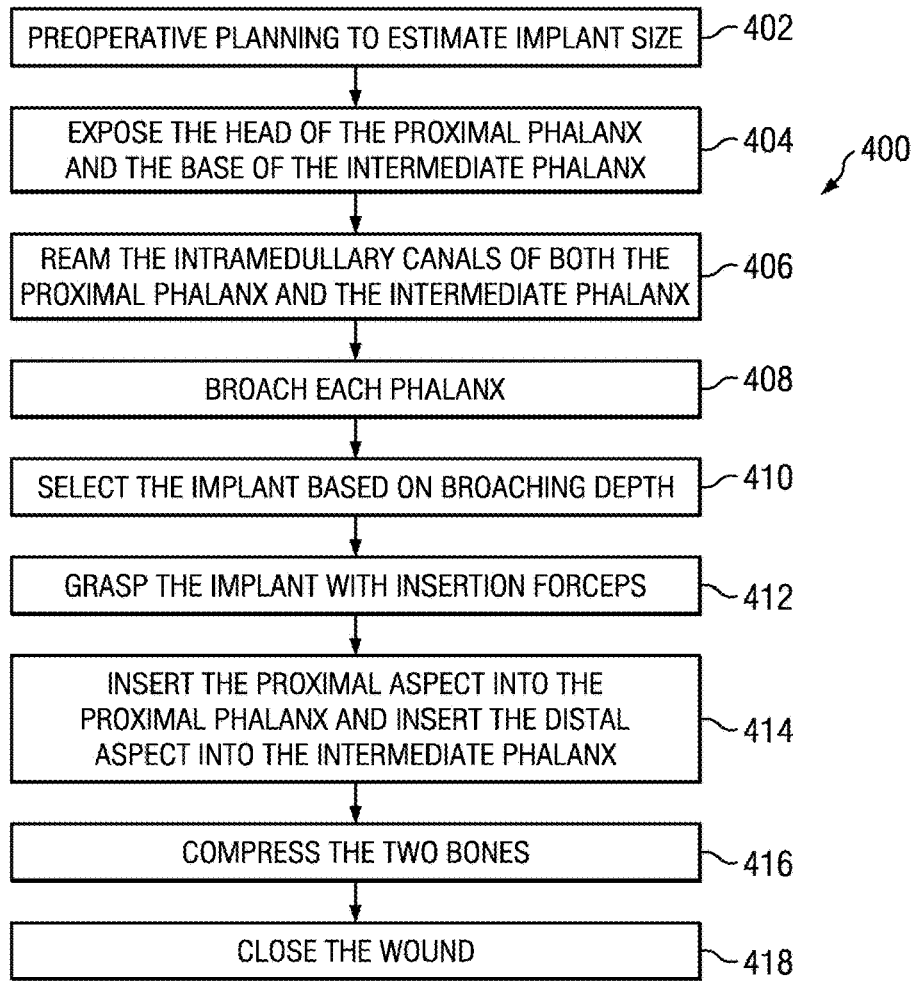
FIG. 10 is a flow chart of an exemplary surgical method of implanting an intramedullary fixation device in accordance with one aspect of the present disclosure.

FIG. 10 is a flow chart describing an exemplary surgical method 400 for implanting the device 100 using the instruments disclosed herein. As becomes apparent from the description below, the arrowhead configuration of both the distal and proximal heads 102, 104 captures bone on both sides of the fusion or fracture site, and may provide internal stability. This is accomplished by pressing and locking the distal and proximal heads 102, 104 into the surrounding bone. The body 106 of the device 100 extends from each head (proximal and distal) and is the portion of the implant that crosses or spans the fusion or fracture site.

The method begins at a step 402 where a health care provider estimates the diameter and length of the implant based upon pre-operative planning. In some examples, this is accomplished by taking and examining pre-op radiographs to estimate the inner diameter of the intramedullary canals of the affected phalanges at the location where the distal and proximal heads of the device 100 are expected to engage. In one example, this includes measuring with a ruler the inner diameter at the point of engagement in the bone. In some examples, the health care provider calculates the diameter by overlaying an image of the implant upon the patient's radiograph taking into account radiograph magnification. The device may be selected so that the inner diameter of the intramedullary canal is at least the same width as the distal or proximal head. Accordingly, in some examples, to achieve an effective fit, the health care provider selects a device with different sized heads. This may increase the likelihood of achieving proper purchase, may ease insertion, and may mitigate impingement of the arrow barbs upon the cortices. The step of selecting the implant based on size may also include estimating the proper length of the device 100 that will engage each phalanx at the desired point of contact. This projected length will also enable the health care provider to approximate the broaching depth for each phalanx.

At a step 404, the health care provider exposes the head of the proximal phalanx and the proximal end of the intermediate phalanx. This may be accomplished by creating an incision over the point of implantation and dissecting through the skin and subcutaneous tissues to expose the head of the proximal phalanx. Tissue may then be removed from the proximal end of the intermediate phalanx. This may include freeing the base of the phalanx from the plantar plate if the health care provider cannot distract the toe enough to place it on the distal head of the implant. Once properly exposed, the health care provider resects the head of the proximal phalanx and the base of the intermediate phalanx.

At a step 406, the health care provider creates pilot holes down intramedullary canals of both the proximal and intermediate phalanx using the reamer 300. This may include observing laser marks to estimate depth of the pilot hole so that the depth corresponds to the depth determined when selecting the implant based on size in step 402. Alternatively, a pre-drill with K-wire or a hand drill may be performed to form the pilot holes.

At a step 408, the health care provider broaches the pilot hole in each phalanx with the broach 320. This increases the diameter of the pilot hole to prepare it for receiving the device 100. Similar to step 408, this may include observing laser marks to estimate depth of the broached hole so that the depth corresponds to the depth determined when selecting the implant based on size in step 402. Broaching the hole may conserve bone by compacting the cancellous bone of the phalanx to engage the distal and proximal heads of the device 100 upon insertion. In some examples, as indicated at step 410, the health care provider notes the broach depth, and reevaluates, or evaluates for the first time, the length of the device needed to achieve a desired fit in the broached pilot hole.

Since the device 100 shown herein is a one-piece device formed of substantially rigid material, it does not require special pre-operative handling. For example, because it does not require deflection for anchoring as do some devices made of shape memory alloys, the device 100 may be maintained at room temperature.

At a step 412, the health care provider grasps the device 100 using the insertion forceps 340. This may include fitting the body 106 in the recesses 352, 354 of the insertion forceps 340 and securing the grip with the locking mechanism 350. Further, it may include grasping the device 100 at a distance from an end that corresponds to the broaching depth of the proximal phalanx. At a step 414, the health care provider axially inserts the device 100 into the proximal phalanx, securing it into the intramedullary canal. The insertion forceps may be used as a positive stop that prevents the implant from inadvertently being inserted to a greater depth than desired. In addition, the surfaces on the heads of the device 100 help the implant stay within the broached canal, while the taper helps reduce the likelihood of it catching on cancellous bone. Keeping the insertion forceps 340 attached to the device 100, the surgeon then grasps the digit of the toe with the distal portion of bone and places the digit over the distal aspect of the device 100 into the broached hole prepared in the intermediate phalanx, locking the device 100 into the intramedullary canal. This is then compressed against the insertion tool 340. With both ends of the device 100 in the respective, adjacent phalanges, the insertion forceps 340 may be removed from the device 100.

At a step 416, the health care provider then grasps and compresses the two phalanges together to advance the proximal and distal ends of the device 100 deeper into both intramedullary canals to a final, locked position. Thus, the device 100 is completely intramedullary. At a step 418, the wound is closed using the surgeon's preferred technique. In some examples, either before or after closing the wound, the final position of the device 100 may be evaluated radiographically to ensure that the phalanges are in close contact without gapping. Since the device 100 may be a single-use bone fixation device designed to be permanently implanted in the medullary canal of the bone, follow-up procedures and surgeries may be unnecessary. Although described with reference to the device 100, it would be apparent that the same method would be employed with any of the devices disclosed herein.

Figure 11:
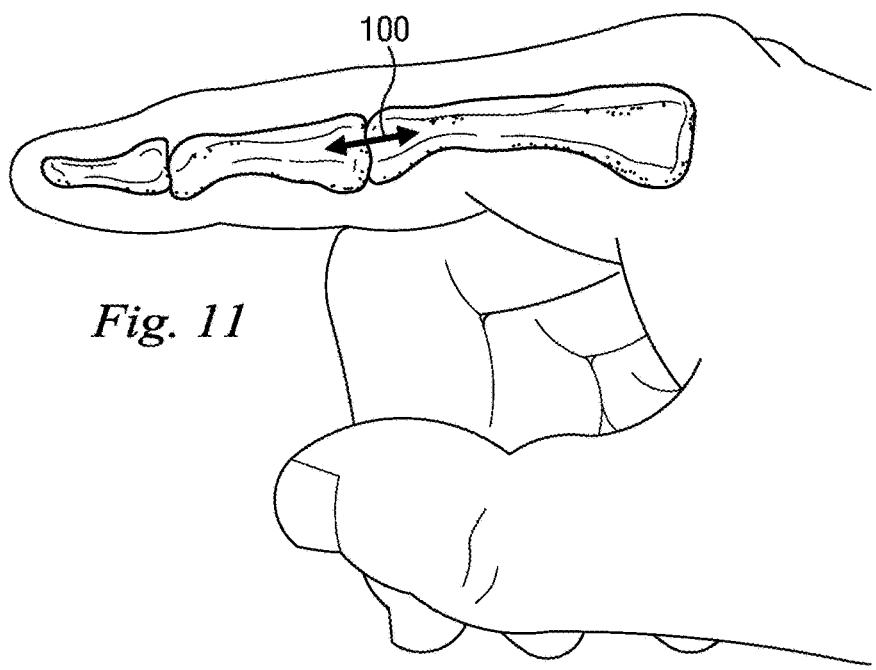
FIG. 11 is an illustration of an exemplary intramedullary fixation device disposed between and within adjacent phalanges of a finger of a patient in accordance with one aspect of the present disclosure.

As indicated above, the exemplary device 100 may be used for treatments other than hammertoe, and in some examples, may be used to treat conditions in the fingers of a hand, or alternatively may be used to treat bone fractures. FIG. 11 is one example showing the device 100 implanted within phalanges of the hand. The device 100 may be implanted in a manner substantially similar to that described above. In addition, removal of the device may be relatively easier than prior, conventional devices. For example, to remove the device, the cylindrical main body may be first cut, and then a cannulated drill may be fit over the cylindrical main body and drilled over to remove bony on-growth from the cylindrical body so that the arrowhead tip can be removed without tearing the bone. This may prevent the health care provider from having to cut the cortical bone in order to remove the implant. Accordingly, the cylindrical shape of the main body may help reduce a chance of compromising cortical bone during revision surgeries. Uses of the device 100 may include but are not limited to hand surgery, orthopedic surgery, plastic surgery, and podiatric surgery. In addition, the implant may be inserted in a variety of angles that differ from its intended position in medullary bone. In some examples, the implant may also be placed through cortical bone and tendon of the hand or foot.

In some examples, the device 100 is machined from a single piece of 316L stainless steel, making it a weld-less, single monolith structure. Various lengths may be provided to meet patient sizing restrictions. The overall lengths of the device 100 may be in the range of 10 mm to 40 mm, while some lengths are within the range of 15 mm to 25 mm. When the device 10 is formed of a single piece of metal, potential stress-risers occurring from welds or adhesives are eliminated and there is no need to assemble intra-operatively. Further, the material and size are selected so that the device has bending and fatigue characteristics able to endure the forces exerted on the lesser toes.

The present disclosure also relates to intramedullary systems, methods, and device used for bone fixation and stabilization of toes and fingers across fusion or fracture sites, and treat deformities, including for example, hammertoe deformities. The intramedullary fixation device includes unique arrow designs on both its proximal and distal ends, and in some embodiments, with the arrow designs varying in size and shape. It is arranged to be completely intramedullary when implanted with no parts of the device exposed outside the skin. Further, it is arranged to resist the rotational and pull-out forces affecting all digits or toes and fingers. Its particular design shape may help it maintain the initial compression applied at insertion.

Figure 12:
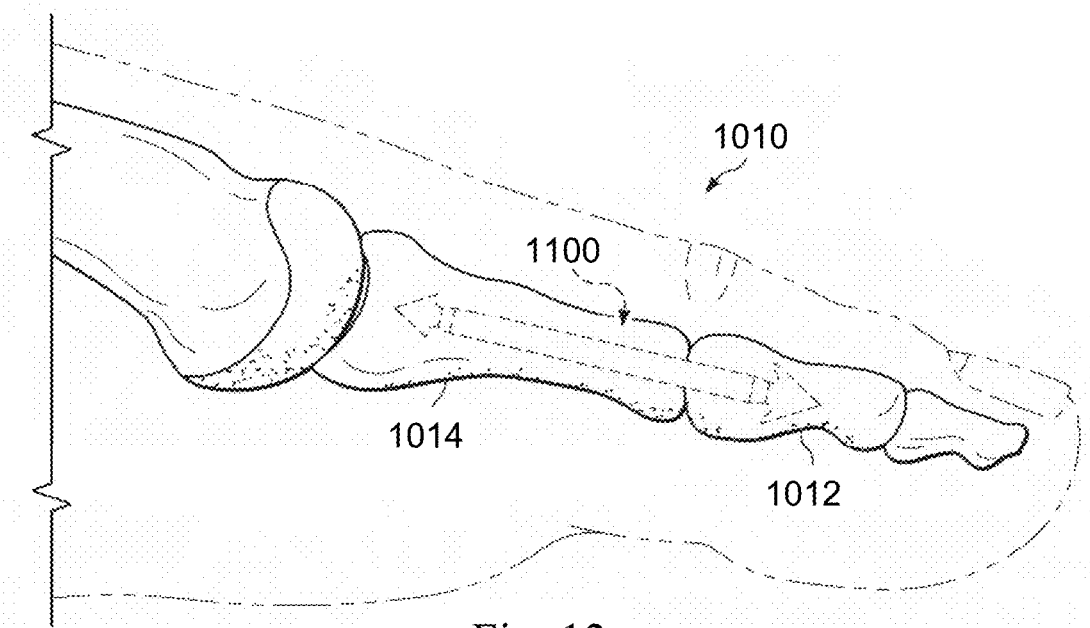
FIG. 12 is an illustration of an exemplary intramedullary fixation device disposed between and within adjacent phalanges of a toe of a patient in accordance with one aspect of the present disclosure.

FIG. 12 shows an exemplary toe 1010 having an intermediate phalanx 1012 and a proximal phalanx 1014. In this example, the toe 1010 has been surgically treated to correct a deformity such as hammertoe as discussed above. Accordingly, the toe includes an implanted intramedullary fixation device 1100 disposed therein in accordance with an exemplary aspect of the present disclosure. In this example, the device 1100 extends between and is implanted within the intermediate and proximal phalanges 1012, 1014. It is described in detail below.

Figure 13A:
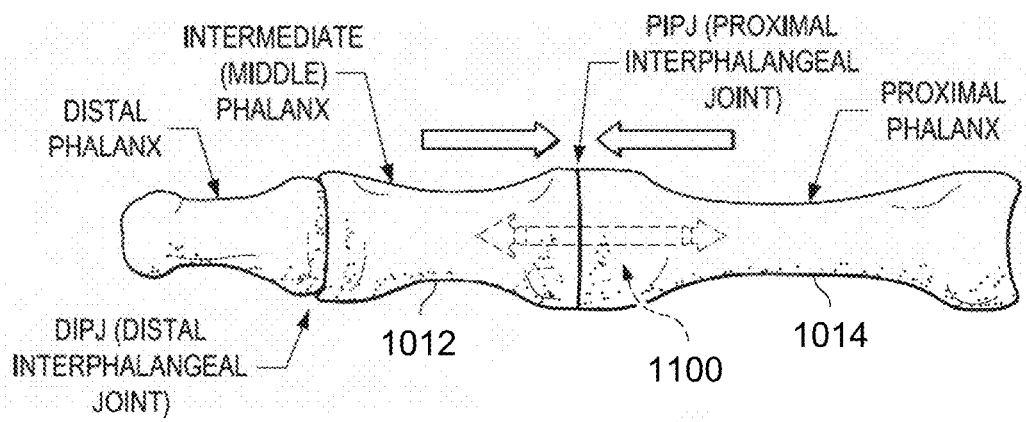
FIGS. 13A-13D are illustrations of exemplary intramedullary fixation devices disposed between and within adjacent phalanges of a toe of a patient in accordance with different aspects of the present disclosure.
Figure 13B:
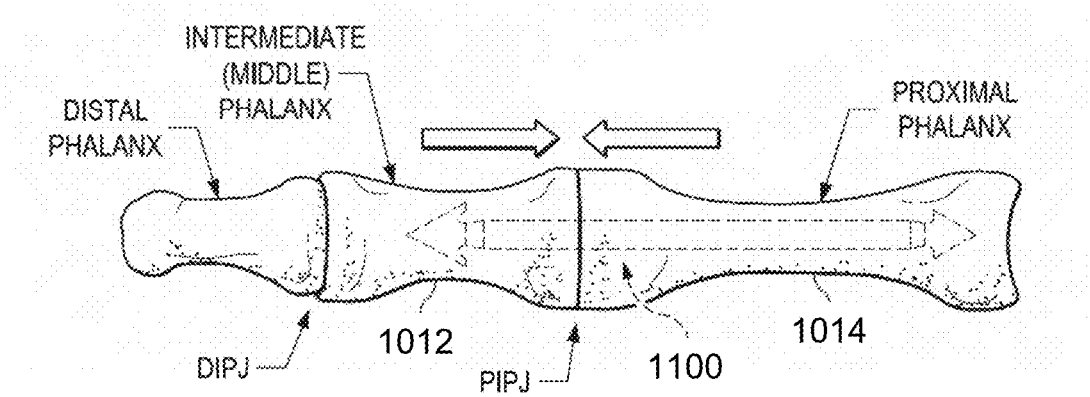

FIG. 13A shows the exemplary device 1100 in greater detail configured and disposed to anchor in the cortex or cancellous bone of the proximal phalanx and the intermediate phalanx. FIG. 13B shows an exemplary device 1100 configured and disposed to anchor in the subchondral bone of the proximal phalanx and cancellous bone or cortex in the intermediate phalanx.

Figure 13C:
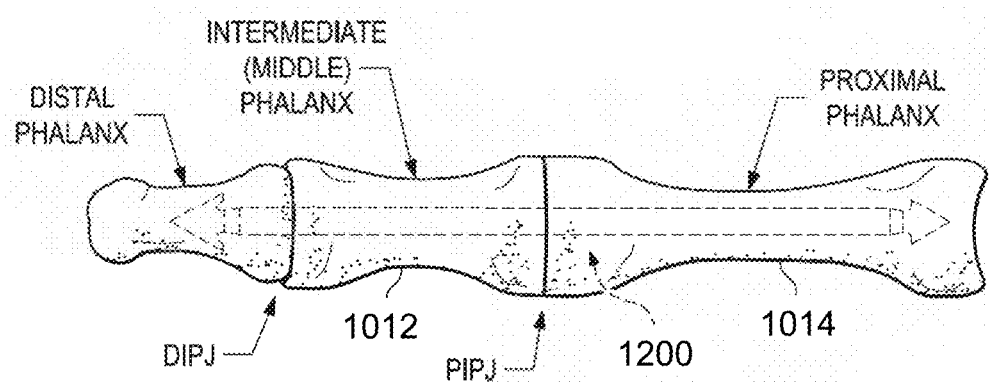

FIG. 13C shows an exemplary device 1200 configured and disposed to anchor in the subchondral bone of the proximal phalanx, to entirely pass through the intermediate phalanx, and to anchor in the distal phalanx.

Figure 13D:
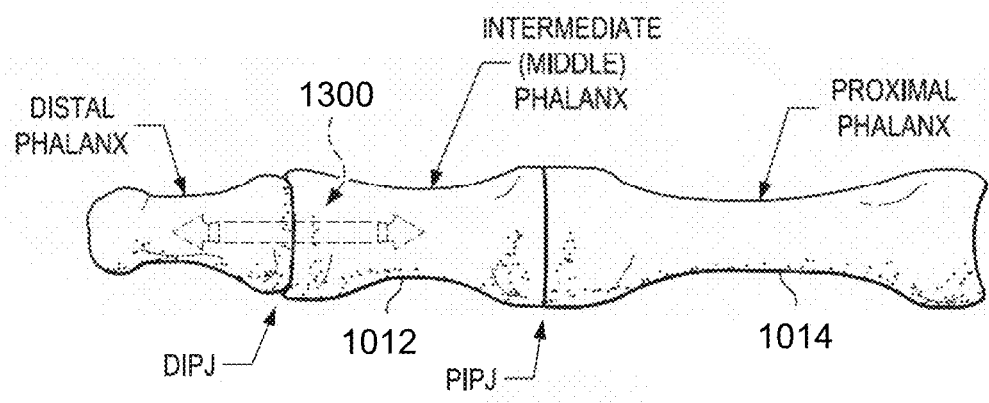
Figure 16:
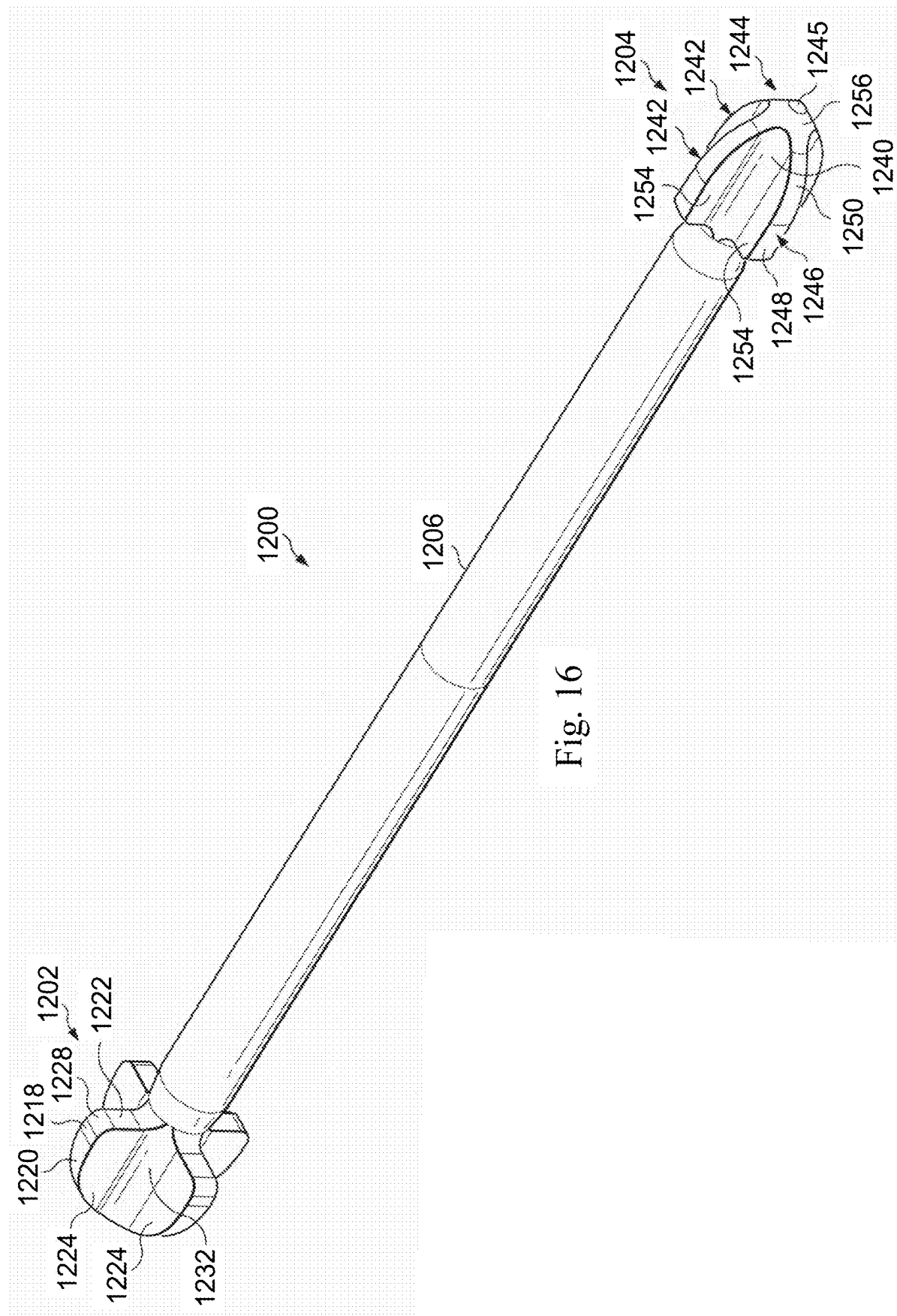

FIG. 13D shows an exemplary device 130 configured and disposed to anchor in the middle phalanx and the distal phalanx. The devices described in greater detail may form or be used to form any of the devices 1100, 1200, and 1300 shown in FIGS. 12 and 13A-13D, with dimensional changes being a difference between devices.

FIGS. 14-18 show another exemplary embodiment of a device, referenced herein as a device 1200 that may be implanted in the manner shown in FIGS. 12 and 13A to 13D. The device 1200 is designed with a three-dimensionally configured arrow at each end and includes a distal head 1202, a proximal head 1204, and a body 1206 extending between the distal and proximal heads 1202, 1204 and having a longitudinal axis 1207. Features consistent with those described above will not be repeated here for the sake of simplicity, but it is understood that the relevant description of features relative to other embodiments described herein also apply to the device 1200.

The distal head 1202 includes a central core portion 1208 and a plurality of radially extending wings 1210. The core portion 1208 extends along the longitudinal axis 1207 of the body 1206 and includes the distal end 1212. In this example, the distal end 1212 is rounded or blunt end to provide smooth insertion into the medullary canal. In addition, because of its rounded shape, when implanted in techniques using bored or reamed holes, the surgeon can feel tactilely when the implant is inserted to the depth of the bored or reamed hole because the rounded end resists further insertion at low insertion forces. However, the surgeon may still insert the device into the intramedullary canal beyond the end of the bored or reamed area by applying additional force. In this embodiment, the distal end 1212 is formed of a convexly shaped leading nub 1214 extending from the surfaces leading to the wings 1210.

The plurality of wings 1210 extend radially from the core portion 1208 and define the outer shape of the distal head 1202. In the embodiment shown, the head 1202, as measured from wing to wing, has a diameter sized to fit within an intramedullary canal of a phalanx and more particularly, within a medullary canal of a middle phalanx.

The wings themselves include an outer surface portion 1216, a trailing surface portion 1222, and lateral sides 1224. In the exemplary embodiment shown, the outer surface portion 1216 of the wings 1210 includes a cylindrical surface portion 1218 and a curved leading surface portion 1220. The outer perimeter surface portion 1218 extends in the longitudinal direction and then intersects with the curved leading surface portion 1220. In this example, the outer perimeter surface portion 1218 of the plurality of wings 1210 together also defines an outer diameter or outer width W1 (FIG. 15) of the distal head 1202. In some embodiments, the head has a width sized within the range of about 2.0 mm to 15 mm. In some embodiments, the width is in a range of about 2.0 mm to 4.5 mm. In one embodiment, the width W1 is sized within the range of about 3.0 mm to 4.0 mm. In one embodiment, the width W1 is sized within the range of about 3.5 mm. In some embodiments, the height of individual wings as measured radially from the axis may vary between different orientations. For example, wings extending in a lateral direction may have a height different than adjacent wings extending in a cross-lateral direction. In some embodiments, the outer perimeter surface portion 1218 of the wings 1210 has a curved outer surface that lies along the boundary of a cylindrical shape at the maximum diameter or width W1, as represented by the dashed lines in FIG. 15. Some embodiments are sized to accommodate a particular bone quality and intramedullary canal diameter. For example, for softer bone quality or for larger canals, the diameter of the distal head may be selected to be within a range of 2.5 mm to 5.0 mm.

Extending from the outer perimeter surface portion 1218, the wings 1210 include the curved leading surface portion 1220. The curved leading surface portion 1220 faces at least partially in the direction of the distal end 1212, and curves from the outer surface portion 1216 toward and smoothly intersects with the core portion 1208. In some embodiments, the curved leading surface portion 1220 has a radius within a range of about 1 mm to 10 mm, in some embodiments, it has a radius within a range of about 1 mm to 4 mm, and in some embodiments has a radius within a range of about 1.5 mm to 2.5 mm. In one embodiment, the radius is 2 mm.

The trailing surface portion 1222 is a surface extending radially inward from the outer surface portion 1216 toward the longitudinal axis of the device 1200 and intersects with the core portion 1208. In the embodiment shown, the trailing surface portion 1222 has a surface that lies substantially normal to the longitudinal axis 1207, although in other embodiments, it may be angled obliquely relative to the longitudinal axis. A rounded, distally projecting edge 1228 connects the trailing surface portion 1222 to the outer perimeter surface portion 1218 of the outer surface portion 1216.

In the embodiment shown, each wing 1210 includes two lateral sides 1224. In the example shown, the lateral sides extend from the outer surface portion 1216 to the core portion 1208. Depending on the embodiment, these lateral sides 1224 may be formed in parallel planes or may be wedge-shaped. The thickness of the wing 1210 is defined by the distance between the lateral sides 1224 and the pull-out resistance is determined by the thickness of the wing 1210 at the trailing surface portion. A wing 1210 having lateral sides 1224 in parallel planes will have uniform thickness and may be easier to implant while still providing rotational stability.

In other embodiments however, these lateral sides 1224 may be formed of nonparallel planes and may form a wedge-shape. For example, one embodiment includes a wing 1210 having a leading portion having a thickness about 0.38 mm at the leading end and a thickness of about 0.52 mm at the trailing end. Other angles are dimensions are also contemplated. Accordingly, the wings are thinner toward the leading end than the trailing end. Embodiments with wedge-shaped wings may require more force to implant. However, they may also provide closer contact between the bone and the wing 1210 because the wing may become gradually thicker from the leading edge to the trailing edge. In addition, increasing thickness of the wing toward the trailing edge maximizes the resistance to pull-out because the wing at the trailing surface portion is at its thickest location.

In some embodiments, the lateral sides 1224 are nonplanar and have a curved surface that promotes interference with bone tissue to resist migration and rotation. Some embodiments include wings that vary by wing thickness. For example, some embodiments include two wings having a first thickness and two additional wings having a second thickness greater than the first thickness. The core portion 1208 smoothly connects and spans between adjacent wings with a cylindrical surface 1232 that extends the length of the wings 1210.

Because the distal end 1212 has a smooth bullet-nose shape, the likelihood of the distal end catching on the cortex and preventing the implant from being advanced smoothly may be diminished. During insertion, the wings 1210 act as sled runners to help the device 1200 slide easily down a reamed pilot hole. In addition, the smooth and curved leading surface portion 1220 on the wings 1210 may enable the implant to be self-centering during the insertion process.

While the distal head 1202 is shown having four wings 1210 forming a plus or cruciate configuration, other embodiments include a different number of wings. One embodiment includes three wings, while another embodiment includes two wings. Yet other embodiments include more than four wings. The number of wings may affect the pull-out resistance of the device 1200. For example, a balance between the number of wings and their relative size may permit the device to be designed to achieve a desired pull-out resistance. Reducing the diameter of the wings may permit the device 1200 to be implanted within smaller diameter intramedullary canals while still providing suitable resistance to pull-out. Some embodiments have the wings of the proximal head rotatably offset from the wings of the distal head. For example, while the wings on the distal head may be disposed at 3, 6, 9, and 12 o'clock, the wings on the proximal head may be disposed at 2, 5, 8, and 11 o'clock. In some embodiments, the wings are offset by 45 degrees.

Because of the central core portion 1208 design, the pilot hole preparation may be done with a rotary motion, such as a power or manual reamer or drill, thereby possibly reducing the need for the step of broaching the pilot hole to form a rectangular cavity.

Some embodiments include a head length that is minimized in order to permit as much bone growth behind the trailing surface portion possible to contribute to resistance to pull-out. In one embodiment, the length of the distal head is within the range of about 2.0 mm to 3.0 mm. Other sizes are also contemplated.

The blade orientation for the distal head 1202 provides not only resistance to rotation and pull-out but also may ease pulling the middle phalanx over the distal head 1202 as the device protrudes from the proximal phalanx The proximal head 1204 includes a central core portion 1240 and a plurality of radially extending wings 1242. Many features of the proximal head 1204 are similar to that of the distal head 1202 and not all the features are re-described here, recognizing that one of ordinary skill would understand that features and alternatives described relative to the distal head 1202 have equal applicability to the proximal head 1204. Like the core portion 1208 of the distal head 1202, the central core portion 1240 extends along the longitudinal axis 1207 of the body 1206. The core portion 1240 includes a proximal end 1244. In this example, the core portion 1240 and the proximal end 1244 differs in shape as described below, while still maintaining a rounded or blunt end to provide smooth insertion into the medullary canal. In this embodiment, the core portion proximal end 1244 includes a conical surface portion 1256 that connects the leading surface portion 1250 and includes a convexly shaped leading nub 1245 extending from the surfaces leading to the wings 1242.

The plurality of wings 1242 extend radially from the core portion 1240 and define the outer shape of the proximal head 1204. In the embodiment shown, the head 1202, as measured from wing to wing, has a diameter sized to fit within an intramedullary canal of a phalanx and more particularly, within a canal of a proximal phalanx.

The wings 1242 themselves include an outer surface portion 1246, a trailing surface portion 1252, and lateral sides 1254. In the exemplary embodiment shown, the outer surface portion 1246 of the wings 1242 includes an outer perimeter surface portion 1248 and a curved leading surface portion 1250. The outer perimeter surface portion 1248 extends in the longitudinal direction and then intersects with the curved leading surface portion 1250. In this example, the outer perimeter surface portion 1248 of the plurality of wings 1242 together also defines an outer diameter or outer width W2 (FIG. 18) of the distal head 1202. In some embodiments, the proximal head 204 has a width sized within the range of about 1.0 mm to 3.5 mm. In one embodiment, the width W2 is sized within the range of about 2.0 mm to 3.0 mm. In one embodiment, the width W2 is sized within the range of about 2.5 mm. In some embodiments, the outer perimeter surface portion 1248 of the wings 1242 has a curved outer surface that lies along the boundary of a cylindrical shape at the maximum diameter or width W2, as represented by the dashed lines in FIG. 18.

Extending from the outer perimeter surface portion 1248, the wings 1242 include the curved leading surface portion 1250. The curved leading surface portion 1250 curves from the outer surface portion 1216 toward and smoothly intersecting with the conical surface portion 1256 of the core portion 1208. In some embodiments, the curved leading surface portion 1250 has a radius sized in the ranges as described with reference to the curved leading surface portion 1220. In one embodiment, the covered leading surface portions 1220, 1250 have the same radius.

The trailing surface portion 1252 extends radially inward from the outer surface portion 1246 toward the longitudinal axis of the device 1200 and intersects with the core portion 1240. A rounded edge 1258 connects the trailing surface portion 1252 to the outer perimeter surface portion 1248 of the outer surface portion 1246.

Each wing 1242 includes two lateral sides 1254. In one embodiment, the thickness of the wings 1242 is measured between the lateral sides 1254 and is in the range of 0.020 mm and 0.060 mm. In one embodiment, the wings are wedge shaped and taper from a thickness of 0.37 mm at its leading end to 0.053 at its trailing end.

As indicated above, the overall length of the proximal head 1204 is greater than that of the distal head 1202. However, the length can be shortened to enhance pull-out resistance. For example, the resistance to pull-out may increase as the distance from the trailing surface portion of the distal or proximal head to the resection increases. For the distal head 1202 that is implanted in the middle phalanx, a shorter head may offer resistance to rotation and still increase the distance from the trailing surface portion of the implant wings to the resection site when implanted to the same depth. Because the trailing surface portion of the wing on the shorter head is farther from the fracture site, a radiograph would give the appearance of the device being more deeply implanted in the middle phalanx. As such the distal head 1202 with its larger diameter is intended for implantation in the medial phalanx and the proximal head 1204 with its smaller diameter is intended for implantation in the proximal phalanx.

The body 1206 is a rigid shaft extending between and connecting the distal head 1202 and the proximal head 1204. In the embodiment shown, the body 1206 is cylindrically shaped and has a substantially smooth exterior surface. In one embodiment, the body 1206 has a diameter or a cross-sectional thickness within a range of about 1.2 mm to 2.0 mm. In one embodiment, the body 1206 has a diameter or a cross-sectional thickness of about 1.6 mm. Other sizes, larger and smaller are contemplated. The body 1206 includes a necked-down region adjacent the proximal and distal head as the body merges with the central core portion.

In some embodiments, the proximal and distal heads form about a 30% or less of the overall length of the device. In one example, the distal head has a length of about 2.5 mm, the proximal head has a length of about 3.0 mm, and the body has a length about 13.5 mm or greater.

Some embodiments of the body 1206 include a plantar grade bend. Different embodiments include a bend that may be selected in the range of about 5-25 degrees. In some examples, the bend is selected to be about a 15 degree bend, while yet other embodiments the bend is selected to be about a 10 degree bend, an in another, about a 5 degree bend.

In the embodiment shown, the body 1206 has a substantially constant diameter. However, some embodiments have body diameters that vary along the length of the body 1206 to correspond to forces and to increase the area of the arrowhead tip resisting pull-out and rotational forces. Two such embodiments are described below relative to FIGS. 19 and 20.

Figure 19:
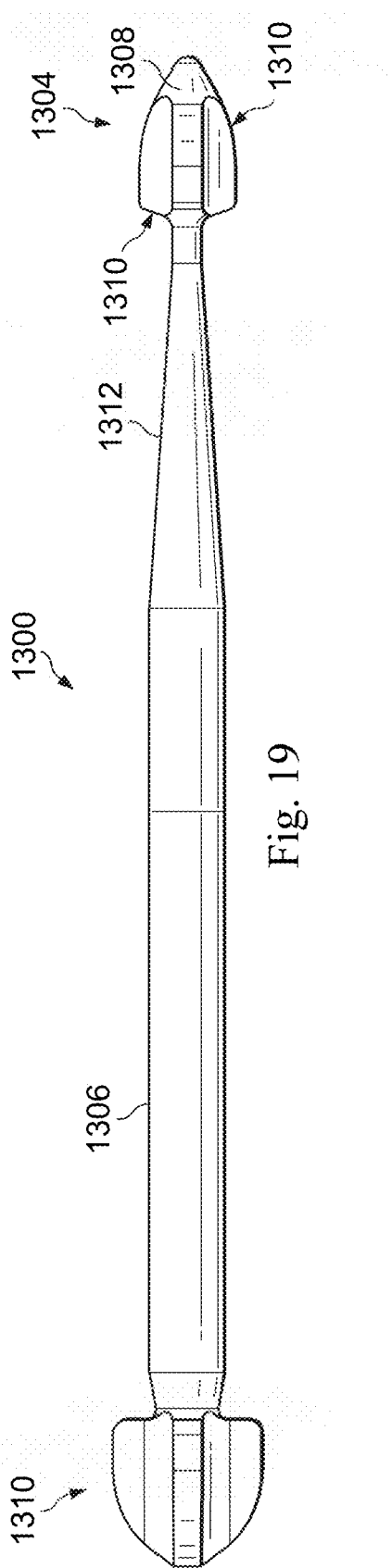
FIG. 19 is an illustration of another exemplary intramedullary fixation device in accordance with one aspect of the present disclosure.

FIG. 19 shows another embodiment of a device referenced herein by the numeral 1300. The device 1300 includes a distal head 1302, a proximal head 1304, and a body 1306. The distal and proximal heads 1302, 1304 include features similar to those described above, and the descriptions apply to this embodiment, recognizing that the size ratio of the different heads may differ on the device 1300. Here, the proximal head 1304 includes a core portion 1308 and wings 1310. The body 1306 in this embodiment includes a tapered shaft region 1312 that extends along a substantial portion of the body 1306.

In this embodiment, the size ratio of tapered shaft region 1312 to the adjacent core portion 1308 of the head may be selected to be minimized. This may permit the body 1306 to be deeply embedded within the phalanx with a minimal amount of tissue disruption. Some embodiments have less than a 1:1.5 tapered shaft region to core portion size ratio, while other embodiments have a 1:1 size ratio. Other sizes and ratios are contemplated. The reduced diameter of the tapered shaft region 1308 may extend less than half the distance of the body 1306 so that the thicker region of the body 1306 may be disposed at the fusion region when the device 1300 is implanted. In the exemplary embodiment shown, the tapered shaft region 1312 extends for a length of more than about 15% of the length of the entire body. In one embodiment, the tapered shaft region 1312 extends from the proximal head a distance between about 15% and 45% of the length of the body 306. In some examples, the tapered shaft region 1312 extends a distance within a range of about 20% and 30% of the length of the body 1306. This may provide a suitable region for bone ingrowth behind the proximal head 304, while still having the thicker portion of the body at the resection site. While referred to as a tapered shaft region 1312, the narrow region of the shaft may also be cylindrical, and may be referred to as a narrow region.

This also may permit the proximal head 1304 to be embedded in the subchondral bone of the proximal phalanx. Reducing the ratio of the core portion 1308 to the body 1306 may increase the resistance to rotation and pull-out. In one embodiment, the body diameter or width is set at a diameter of 1.0 mm so that an additional 0.25 mm per wing (0.5 mm total) is available to resist rotational forces. The increased area resisting pull-out is also 0.25 mm per wing multiplied by the width of the wing 1310 at the trailing surface portion, multiplied by the number of wings 1310. In this embodiment, a reamer width would be reduced to the width of the body 1306 at the narrowest point.

In the example shown, the thickness or cross-sectional width of the body 1306 that aligns with the resection site and into the distal tip of the implant would remain at the thickest portion of the body 1306, which in one embodiment, is 1.6 mm.

Figure 20:
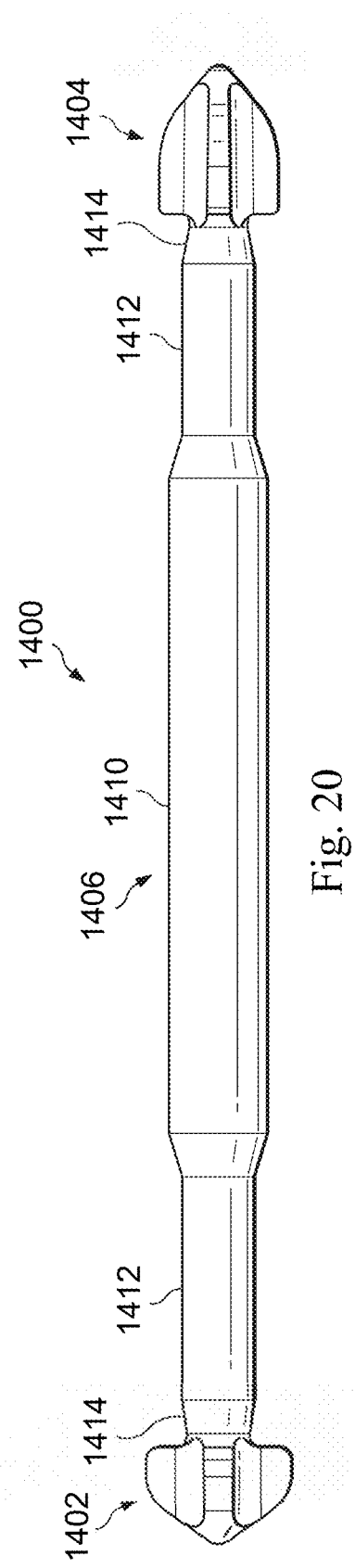
FIG. 20 is illustrations of another exemplary intramedullary fixation device in accordance with one aspect of the present disclosure.
Figure 21:
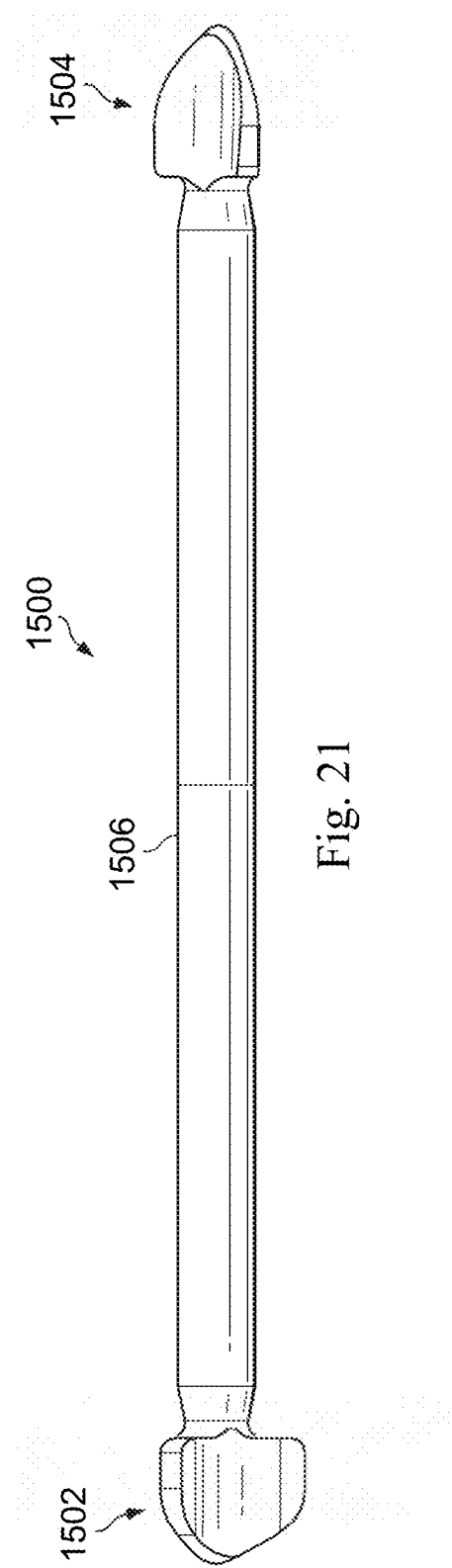
FIGS. 21-25 are illustrations of another exemplary intramedullary fixation device in accordance with one aspect of the present disclosure.
Figure 23:
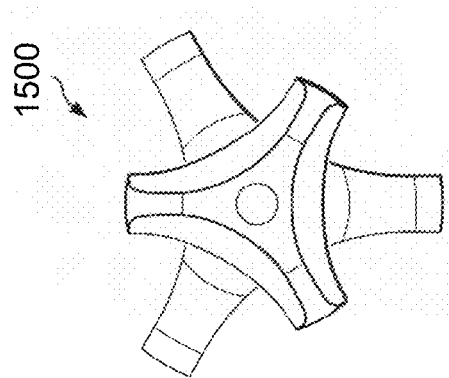
Figure 22:
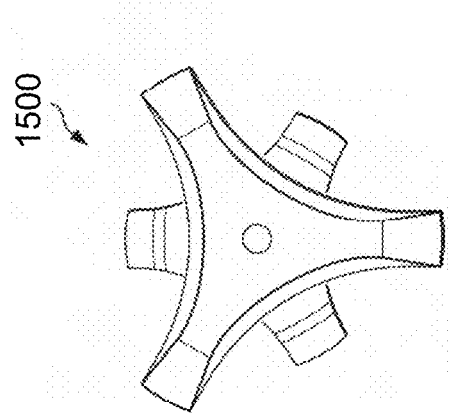
Figure 24:
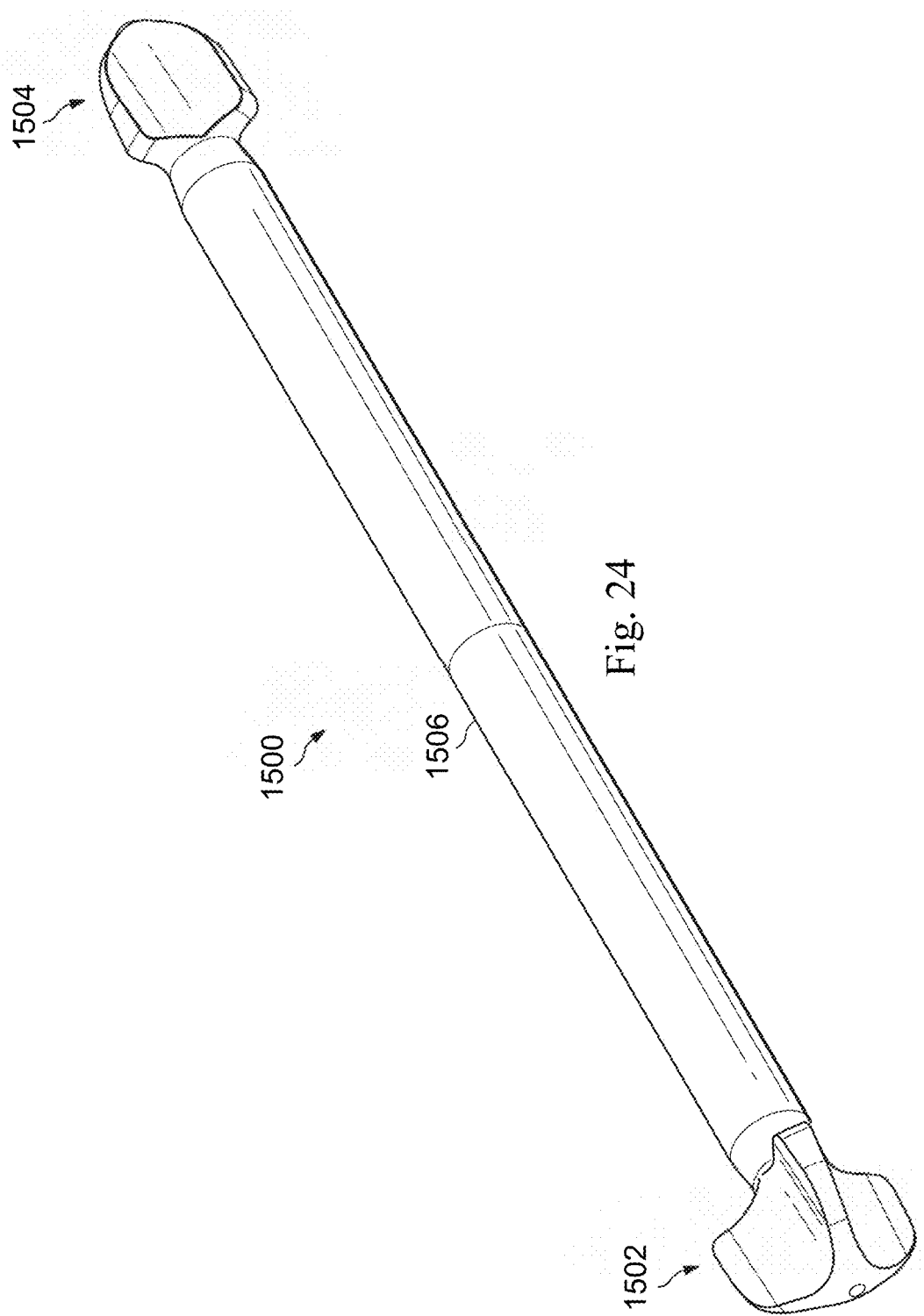
Figure 25:
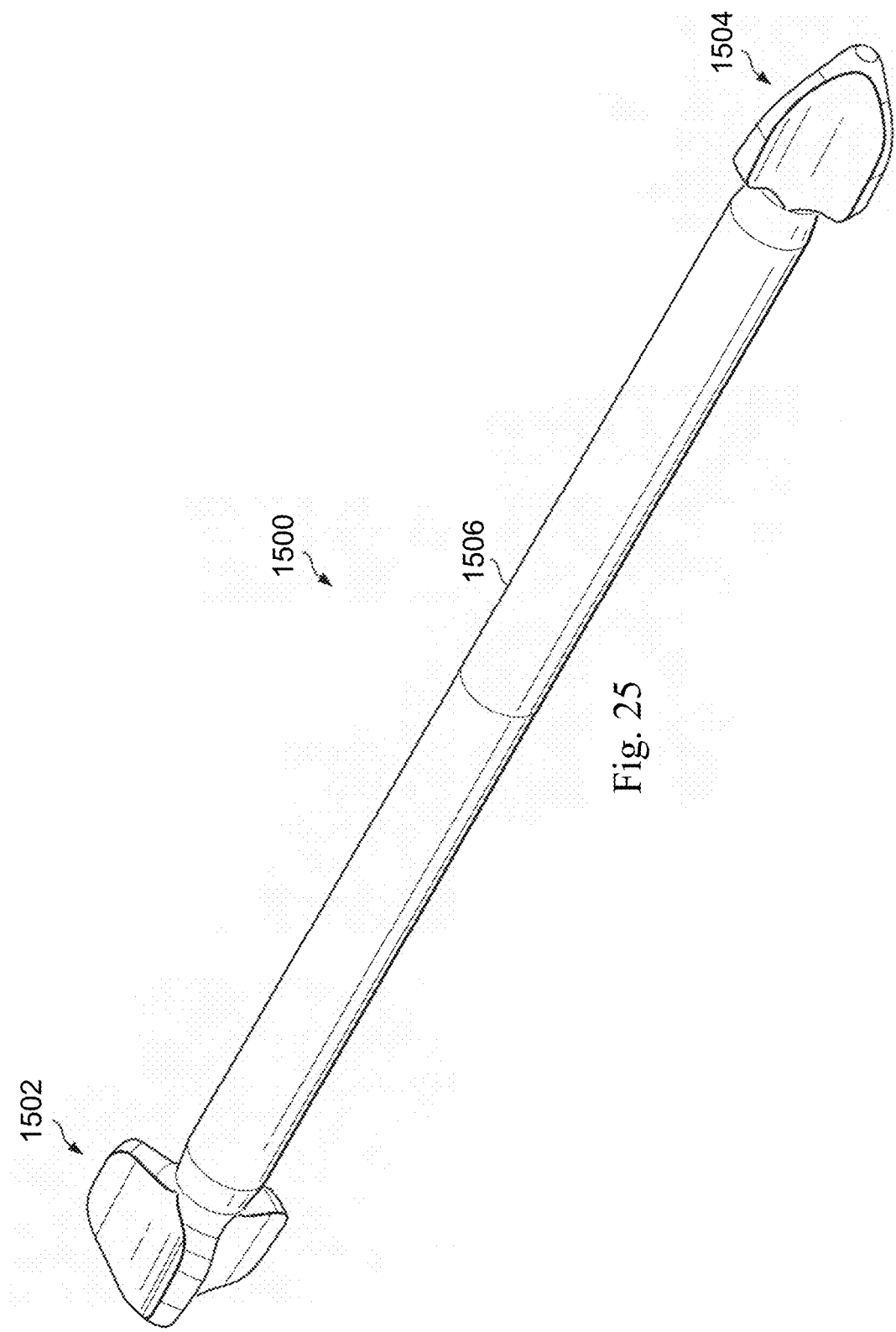
Figure 29:
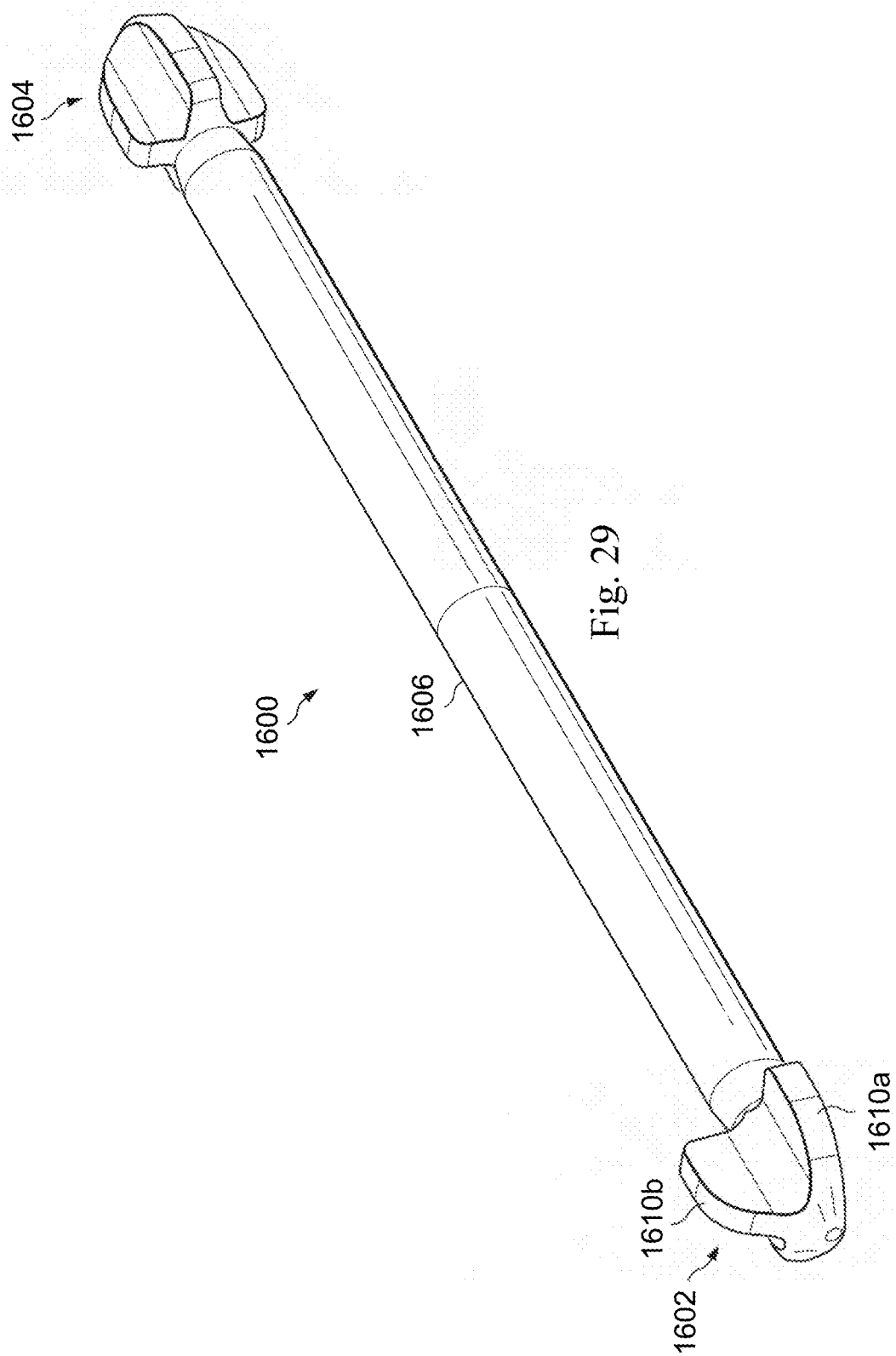
Figure 30:
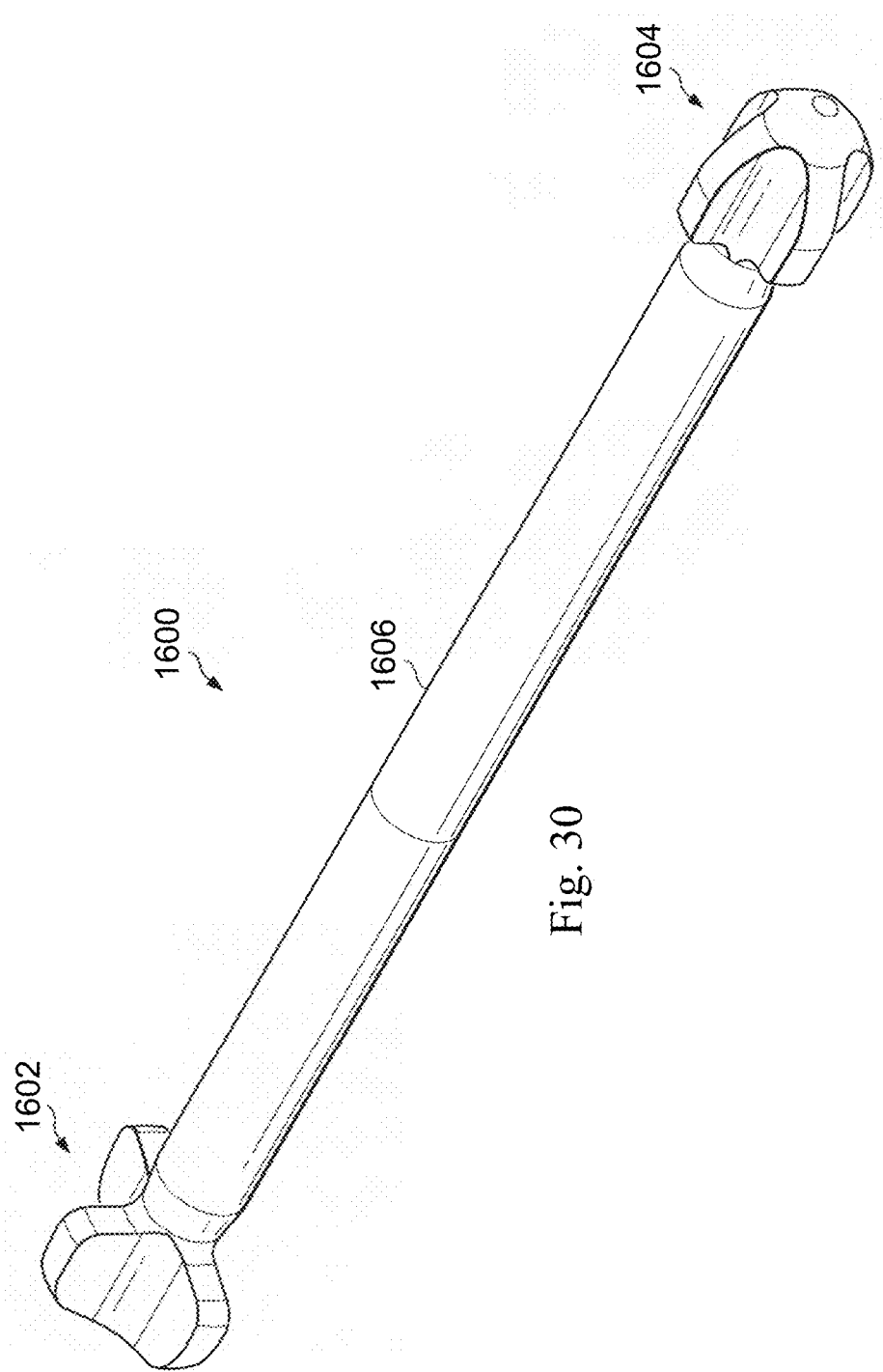

FIG. 20 shows another embodiment of a device, reference herein by the numeral 1400. The device 1400 includes a distal head 1402, a proximal head 1404, and a body 1406. The distal and proximal heads 1402, 1404 include features similar to those described above, and the descriptions apply to this embodiment, recognizing that the size ratio of the different heads may differ on the device 1400. In this embodiment, the body 1406 includes a central region 1410 of increased thickness. Accordingly, the body 1406 includes narrower regions 1412 at the distal and proximal ends, and these narrow further at necks 1414 to form the respective distal and proximal heads 1402, 1404.

Here, the central region 1410 may provide greater strength and a tighter fit at the site of the resection. In one embodiment, the width or diameter of the body 4106 in the central region 1410 is within a range of about 1.8 mm-2.2 mm to enhance the fixation at the resection site and to stabilize the device by helping to reduce play of the device 1400. This may also increase the strength of an already strong implant at the point of greatest potential stresses. In such an embodiment, the reamer diameter may remain at a size to accommodate the narrower regions 1412. For example, the narrow regions 412 may have a diameter of about 1.6 mm, and therefore, in some examples, the reamer diameter would also be 1.6 mm. In one embodiment, the central region 1410 may extend about 40-70% of the length of the body. In other embodiments, the central region extends about 40-60% of the length of the body.

Figure 17:
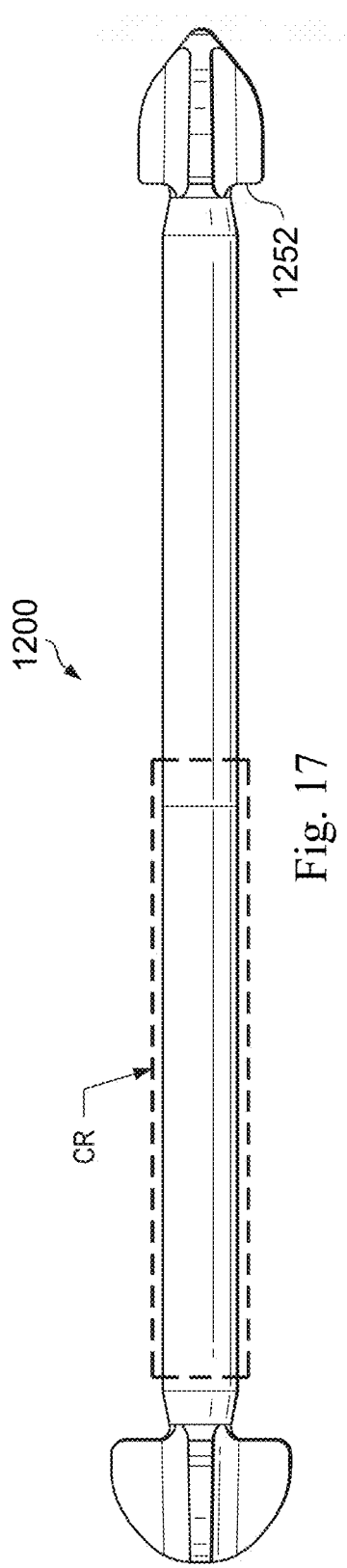
Figure 18:
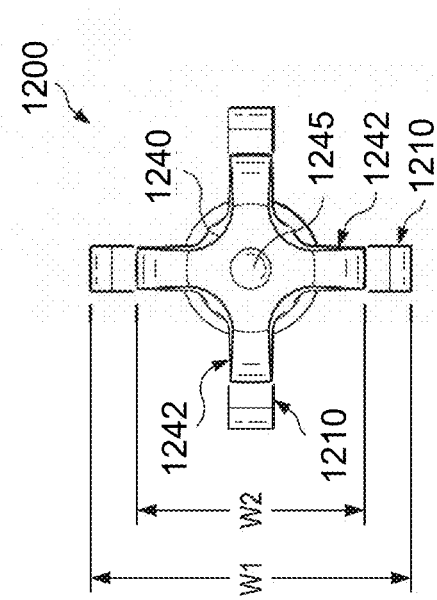

Some embodiments of the bodies disclosed herein include a coating or tissue growth material. For example, some embodiments include an aggressive porous material or coating that is "sticky" to tissue. Some examples include a bone-growth promoting substance, such as, for example, a hydroxyapatite coating formed of calcium phosphate, tricalcium phosphate (TCP), and/or calcium carbonate. Alternatively, osteoinductive coatings, such as proteins from transforming growth factor (TGF) beta superfamily, or bone-morphogenic proteins, such as BMP2 or BMP7, may be used. These coatings may increase adhesion to cancellous bone, increasing resistance to pull-out and rotational forces. They also may accelerate bony ingrowth and accelerate consolidation of the bone. The coating may be applied along the entire body of the device, or may be applied only along a specific region, such as a region, that is half of the body adjacent the distal head, for example. FIG. 17 shows one example of a coating region, identified by the box labeled CR. The coating may be arranged in other ways also.

Although shown as cylindrical, any of the bodies disclosed herein may have a cross-section of any suitable shape, and may include, for example, a shaft shape that is triangular shaped, square shaped or one with edges rather than cylindrical. These types of body cross-sections can provide additional resistance to rotational forces. In another example, edges emerging from the body can serve to provide additional fixation.

In some embodiments, the proximal head of the devices is sized and configured to be embedded in the subchondral bone at the base of the proximal phalanx. The rounded blunt tip may require greater force than the sharper, pointier arrow of the other embodiments to progress farther into the subchondral bone than the prepared hole provides. Accordingly, the blunt bullet nose may prevent the implant from advancing past the end of the reamed pilot hole.

In one embodiment, the length of the proximal head is about 2.0 mm in the longitudinal direction. This length permits the addition of one or two additional wings that may increase both the level of the resistance to rotation and pull-out without increasing the length of the arrowhead. Increasing the length could adversely affect the pull-out resistance in vivo, for example, if the longer arrowhead were to not be completely embedded in subchondral bone. In this example, the wings are formed so that the head is substantially symmetrical.

FIGS. 21-25 show an additional embodiment of a device, referenced herein by the numeral 1500, including a distal head 1502, a proximal head 1504, and a body 1506. The distal and proximal heads 1502, 1504 include features similar to those described above, and the descriptions apply to this embodiment, recognizing that the size ratio of the different heads may differ on the device 1500. In this embodiment, the distal and proximal head each include three wings radially extending from a central core. As can be seen, and consistent with the description above, the distal head has a greater width and a smaller length than the proximal head. Here, as can be seen in the end views shown in FIGS. 22 and 23, the wings of the distal head and the proximal head are rotationally offset. Since there are three wings, they are rotationally offset by 60 degrees.

FIGS. 26-30 show an additional embodiment of a device, referenced herein by the numeral 1600, including a distal head 1602, a proximal head 1604, and a body 1606. The distal and proximal heads 1602, 1604 include features similar to those described above, and the descriptions apply to this embodiment, recognizing that the size ratio of the different heads may differ on the device 1600.

In this embodiment however, the proximal head 1604 includes four wings and may be similar to those discussed above, the distal head 1602 includes a non-symmetric head providing specific advantages.

In this embodiment, the distal head 1602 includes three wings 1610 spaced about an axis of the device 1600. For reference, the wings are identified as 1610a, 1610b, and 1610c. The wings 1610a and 1610c are spaced 90 degrees apart from adjacent wing 1610b, but, the wings 1610a and 1610c are adjacent and spaced 180 degrees apart, forming an asymmetric distal head 1602. Accordingly, a plantar wing is not present. Therefore, these wings 1610a and 1610c form a planar surface and the wing 1610b, also referred to as the dorsal wing, extend perpendicular away from the planar surface.

As such, the distal head 1602 is configured to provide rotational stability with the three present wings, but also may be easier to insert into a phalanx during surgery. For example, by orienting the device and inserting the device in the proper arrangement, the distance the middle phalanx would need to be extended to place the distal tip of the implant near the prepared pilot hole may be less than with a plantar wing in place.

In this embodiment, the distal head 1602 forms a T-shaped configuration with the planar surface extending from one side to the other. The planar surface is parallel to but offset from the central longitudinal axis. Further, as can be seen in FIG. 28, a plane along the planar surface intersects the body 1606 of the device 1600. Another embodiment may orient the 3 wings at different angles (10 o'clock, 12 o'clock and 2 o'clock).

One embodiment employs a sideways X-wing cross-section (having acute and oblique angles between adjacent wings) to provide the balance between ease of use and stability.

The devices may be implanted using any of a number of surgical instruments or tools, including for example, a reamer, a broach, and an insertion forceps. These instruments are described in detail in prior U.S. patent application Ser. No. 13/084,048 to Roman, filed Apr. 11, 2011, and incorporated herein by reference.

Furthermore, the devices disclosed herein may be provided as a kit in combination with a plurality of devices of different sizes or the instruments themselves. One exemplary kit includes a device as described above, with the reamer, the broach, and the insertion forceps. Other kits are described in prior U.S. patent application Ser. No. 13/084, 048 to Roman, filed Apr. 11, 2011, and incorporated herein by reference.

The devices herein may be used in exemplary surgical methods for implanting the device for the treatment or correction of bone deformities. When implanted, the arrowhead configuration of both the distal and proximal heads captures bone on both sides of the fusion or fracture site, and may provide internal stability. This is accomplished by pressing and locking the distal and proximal heads into the surrounding bone. The body of the device extends from each head (proximal and distal) and is the portion of the implant that crosses or spans the fusion or fracture site.

Figure 31:
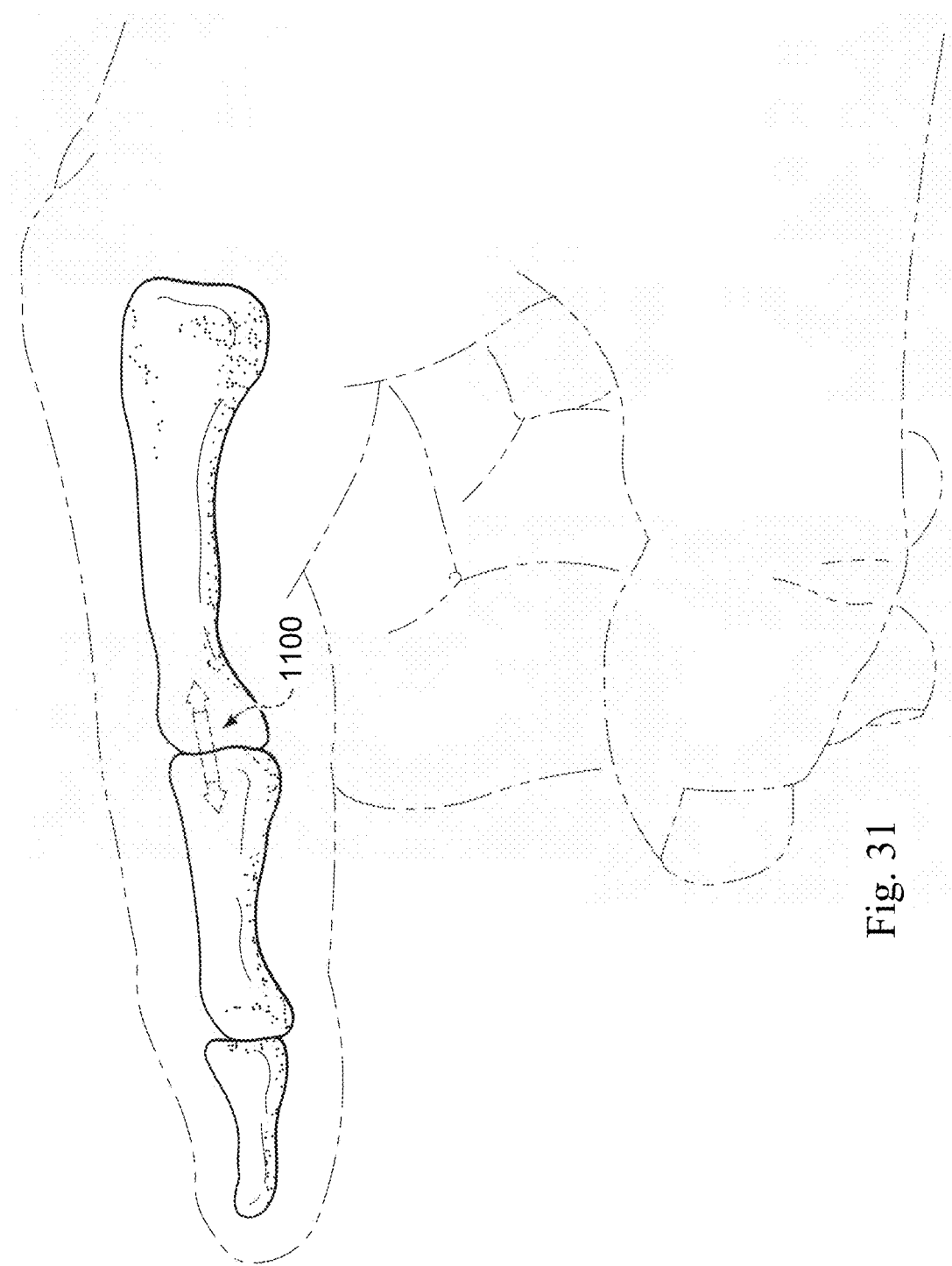
FIG. 31 is an illustration of an exemplary intramedullary fixation device disposed between and within adjacent phalanges of a hand of a patient in accordance with one aspect of the present disclosure.

It should be noted that the exemplary devices described herein may be used for treatments such as hammertoe, and in some examples, may be used to treat conditions in the fingers of a hand, or alternatively may be used to treat bone fractures. FIG. 31 is one example, which could be any of the devices disclosed herein implanted within phalanges of the hand. In addition, removal of the device may be relatively easier than prior, conventional devices. For example, to remove the device, the cylindrical main body may be first cut, and then a cannulated drill may be fit over the cylindrical main body and drilled over to remove bony on-growth from the cylindrical body so that the arrowhead tip can be removed without tearing the bone. This may prevent the health care provider from having to cut the cortical bone in order to remove the implant. Accordingly, the cylindrical shape of the main body may help reduce a chance of compromising cortical bone during revision surgeries. Uses of the device may include but are not limited to hand surgery, orthopedic surgery, plastic surgery, and podiatric surgery. In addition, the implant may be inserted in a variety of angles that differ from its intended position in medullary bone. In some examples, the implant may also be placed through cortical bone and tendon of the hand or foot.

In some examples, the device is machined from a single piece of 316L stainless steel, making it a weld-less, single monolith structure. In other embodiment, it may be formed of two structures welded or brazed together. Various lengths may be provided to meet patient sizing restrictions. The overall lengths of the device may be in the range of 10 mm to 70 mm, while some lengths may be within the range of 10 mm to 40 mm, while yet additional lengths are within the range of 15 mm to 25 mm. When the device is formed of a single piece of metal, potential stress-risers occurring from welds or adhesives are eliminated and there is no need to assemble intra-operatively. Further, the material and size are selected so that the device has bending and fatigue characteristics able to endure the forces exerted on the lesser toes.

The present disclosure also relates to intramedullary systems, methods, and devices used for bone fixation and stabilization of toes and fingers across fusion or fracture sites, and treat deformities, including for example, hammertoe deformities. The intramedullary fixation device includes unique arrow designs on both its proximal and distal ends, and in some embodiments, with the arrow designs varying in size and shape. It is arranged to be completely intramedullary when implanted with no parts of the device exposed outside the skin. Further, it is arranged to resist the rotational and pull-out forces affecting the lesser toes. Its particular design shape may help it maintain the initial compression applied at insertion.

Figure 32:
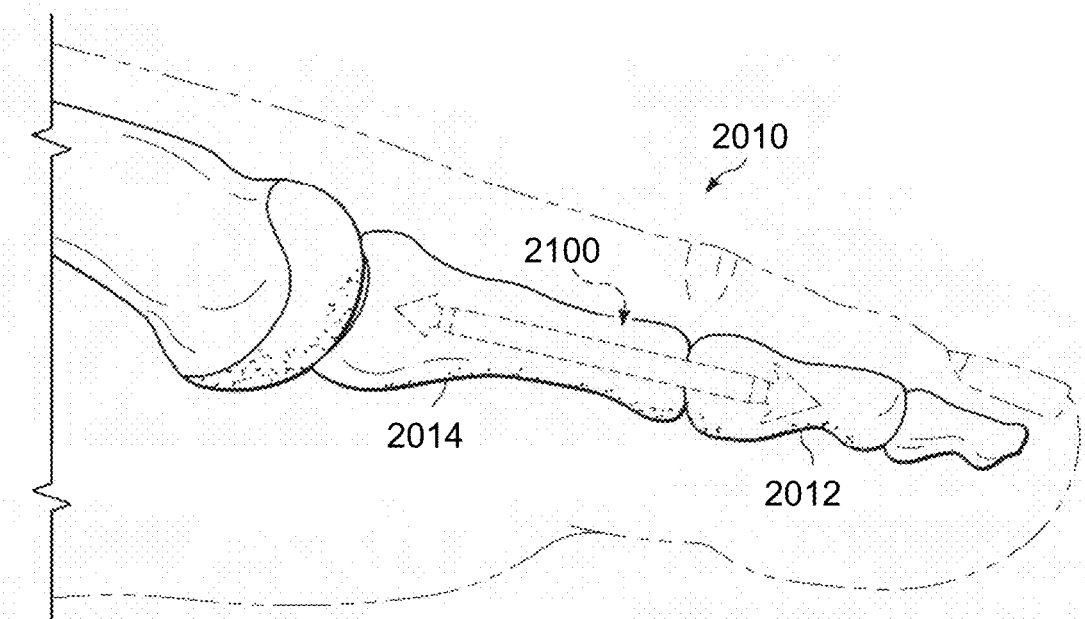
FIG. 32 is an illustration of an exemplary intramedullary fixation device disposed between and within adjacent phalanges of a toe of a patient in accordance with one aspect of the present disclosure.

FIG. 32 shows an exemplary toe 2010 having an intermediate phalanx 2012 and a proximal phalanx 2014. In this example, the toe 2010 has been surgically treated to correct a deformity such as hammertoe as discussed above. Accordingly, the toe includes an implanted intramedullary fixation device 2100 disposed therein in accordance with an exemplary aspect of the present disclosure. In this example, the device 2100 extends between and is implanted within the intermediate and proximal phalanges 2012, 2014.

Figure 33A:
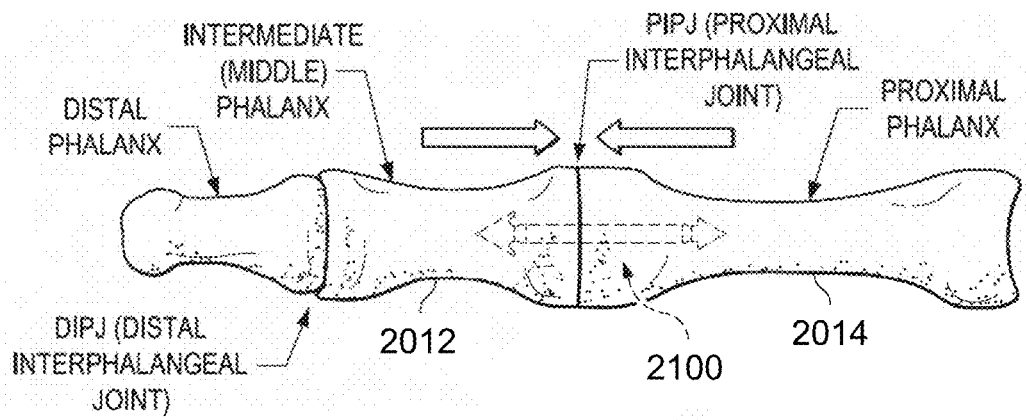
FIGS. 33A-33D are illustrations of exemplary intramedullary fixation devices disposed between and within adjacent phalanges of a toe of a patient in accordance with different aspects of the present disclosure.
Figure 33B:
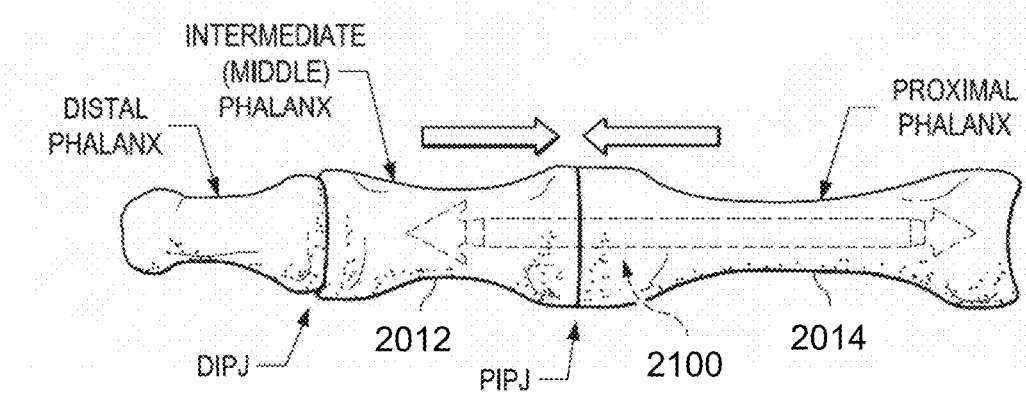

FIG. 33A shows the exemplary device 2100 in greater detail configured and disposed to anchor in the cortex of the proximal phalanx and the intermediate phalanx. FIG. 33B shows an exemplary device 2020 configured and disposed to anchor in the subchondral bone of the proximal phalanx and in the intermediate phalanx.

Figure 33C:
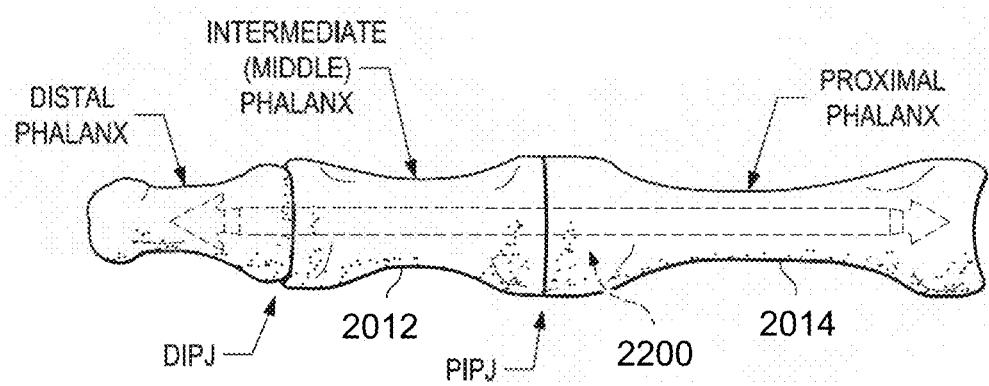

FIG. 33C shows an exemplary device 2030 configured and disposed to anchor in the subchondral bone of the proximal phalanx, to entirely pass through the intermediate phalanx, and to anchor in the distal phalanx.

Figure 33D:
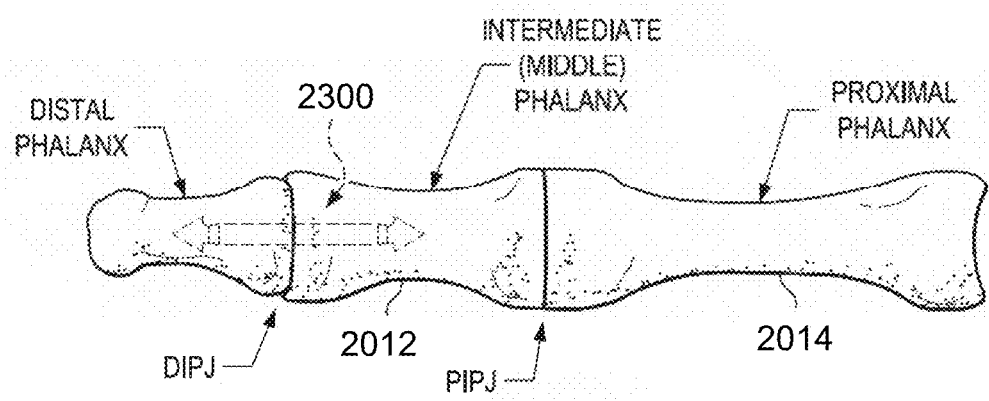

FIG. 33D shows an exemplary device 2040 configured and disposed to anchor in the intermediate phalanx and the distal phalanx. The devices described in greater detail herein may form or be used to form any of the devices 2100, 2200 and 2300 shown in FIGS. 32 and 33A-33D, with dimensional changes being a difference between devices. The device 2100, as a representative device, is described in detail below.

Figure 36:
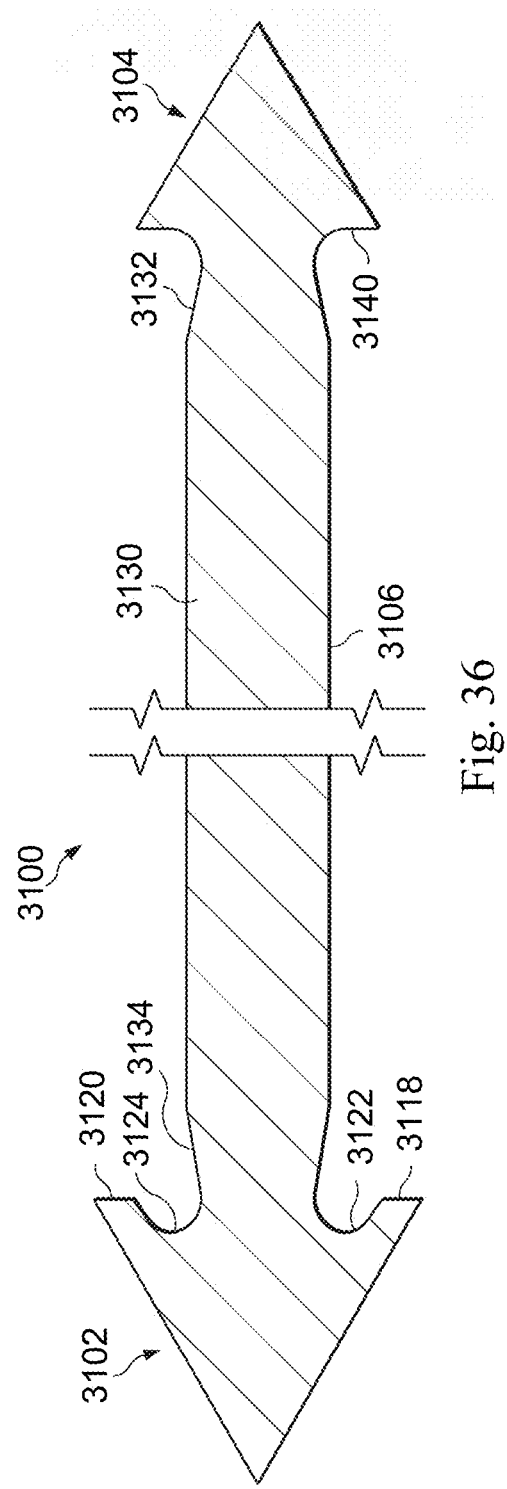
FIG. 36 is an illustration of a cross-sectional view of the exemplary intramedullary fixation device of FIG. 3 along the lines 4-4 in FIG. 3 in accordance with one aspect of the present disclosure.
Figure 39:
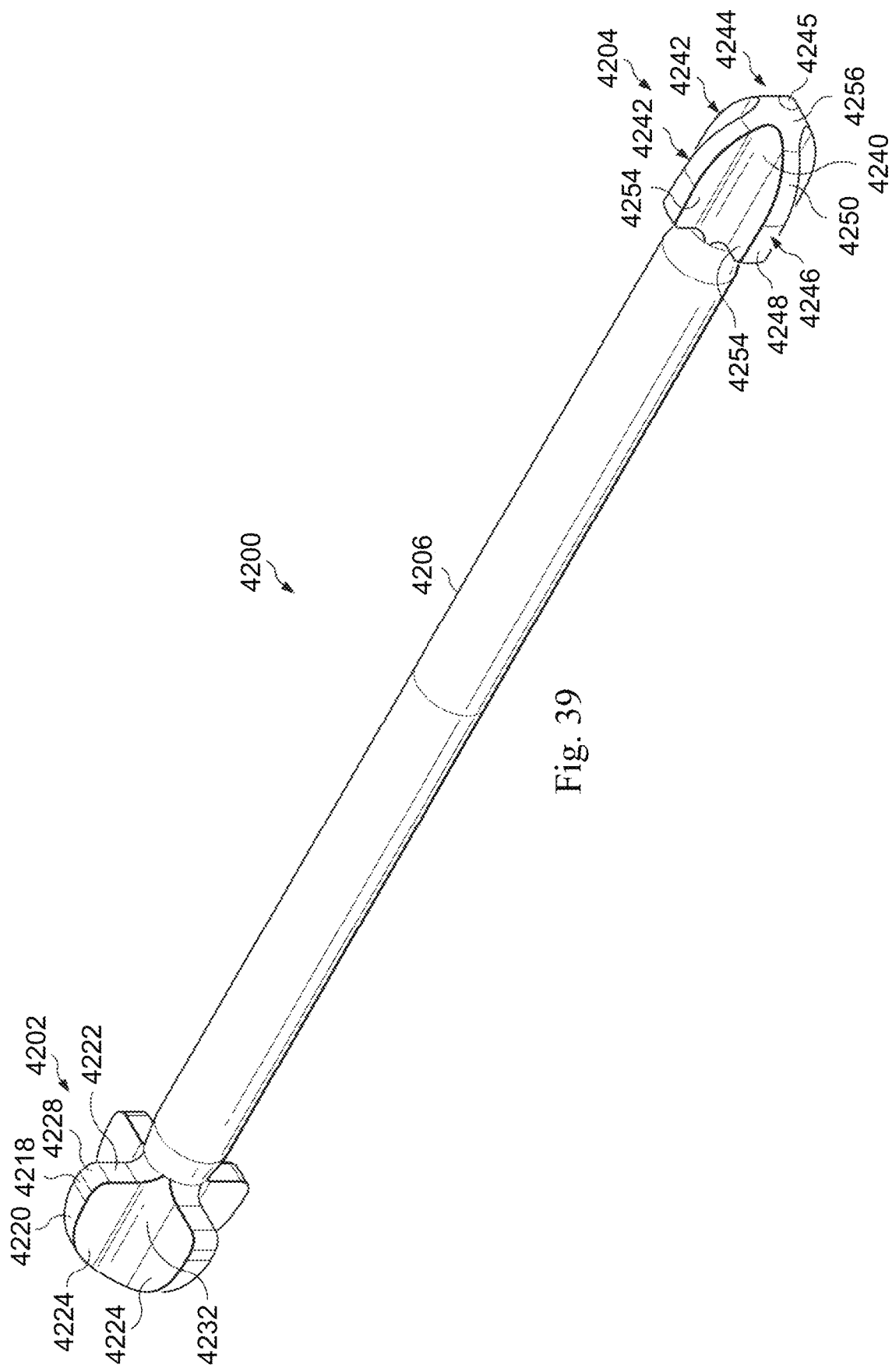

FIGS. 34-36 show one exemplary embodiment of the device 3100 of the present application. The device 3100 is designed with a three-dimensionally configured arrow at each end and includes a distal head 3102, a proximal head 3104, and a body 3106 extending between the distal and proximal heads 3102, 3104. As will become apparent from the below description, the individual components of the device 3100 work in conjunction with one another to stabilize bone during arthrodesis procedures and across fractures. While the heads are described as proximal and distal heads, it should be understood that the proximal head may be implanted in a distal position and the distal head may be implanted in a proximal position.

The distal head 3102 is formed as a three dimensional arrowhead that is sized for placement in an intramedullary canal of a patient. It is configured so that edges of the arrowhead grasp the cancellous bone in the medullary canal as it is inserted, stabilizing the arthrodesis or fusion site during the osseous union. In this exemplary embodiment, the distal head 3102 is formed as a distal end having a distal-most point 3108. The distal-most point 3108 leads the device 3100 down the reamed or broached insertion channel to its final implantation site during insertion. In this example, the distal-most point 3108 is a sharp point arranged to glide through tissue within the intramedullary canal to ease insertion. Other configurations of the arrowhead's tip may result in successful insertion based on preparation of the insertion site.

First, second, third, and fourth outer facing surfaces 3110, 3112, 3114, 3116 intersect at and extend from the distal most point 3108 in the proximal direction, forming a four-sided pyramidal shape. Although shown as having four outer facing surfaces, some embodiments include greater or fewer outer facing side surfaces. In the example shown, opposing surfaces angle away from each other to define a leading angle. For example, the opposing first and third outer facing surfaces 3110, 3114 define an angle θ relative to a longitudinal axis 3117 of the arrowhead shaped distal head 3102. In some examples, the angle θ is in the range of about 5 degrees to about 45 degrees. In other examples, the angle θ is in the range of about 7-20 degrees, and in some embodiments, the angle is around 11 degrees. In a similar manner, the opposing second and fourth outer facing surfaces 3112, 3116 of the arrowhead shaped distal head 3102 form an angle α. In the example shown, the angle α is larger than the angle θ. The angle α may be selected to be within the range of about 15-60 degrees, and in some embodiments, is in the range of about 20-45 degrees. In some examples, the angle α is about 30 degrees. The multiple angles described on the distal head may vary based on the size and strength of bone in which the device is to be implanted.

In the embodiment shown, the second and fourth outer facing surfaces 3112, 3116 have rounded outer surfaces. At the proximal end of these surfaces, the second and fourth outer facing surfaces 3112, 3116 have a diameter D within a range of about, for example, 2.5-4.5 mm. In some embodiments, the diameter D is in a range of about 3.0-4.0 mm, and in one embodiment, the diameter D is about 3.5 mm. In other embodiments, the second and fourth outer facing surfaces 3112, 3116 are each planar surfaces.

Because of the different angles between the opposing first and third surfaces 3110, 3114 and the opposing second and fourth surfaces 3112, 3116, the width of the distal head 3102 differs from side to side. This is easily seen by comparing FIGS. 34 and 35, different views of the distal head 3102. This differing width increases resistance to rotation that may occur if the device 3100 were cylindrical or to a lesser extent substantially square, although such embodiments are contemplated. Further, the differing width may permit an implanted device to be removed, rotated 90 degrees and implanted again while still providing satisfactory anchoring.

Because of its different widths, the distal head 3102 may be sized so that the diameter D of the head 3102 is greater than a longitudinal length L of the distal head 3102. In embodiments where the second and fourth outer facing surfaces 3112, 3116 are planar, the distance between the surface measured at the proximal ends of these surfaces correspond to the diameter D measurements mentioned above. The longitudinal length L may be sized in the range of about 1.5-5.5 mm. In one example, the diameter D is around 3.5 mm and the longitudinal length L is about 3 mm. Other sizes however, both larger and smaller, are contemplated, and in one example, the width and the length are substantially equal.

In the example shown, the distal head 3102 includes two proximally projecting barbs 3118, 3120. These barbs are configured to engage tissue within the intramedullary canal and resist movement and migration and/or axial displacement within the canal once they have been inserted into the canal. As can be seen, these barbs 3118, 3120 are formed by edges of respective outer facing surfaces 3112, 3116 and because of the pyramidal shape of the distal head, the edges lie in substantially parallel lines.

Inner surfaces of the barbs 3118, 3120 are formed by first and second undercuts 3122, 3124 disposed respectively between tips of the barbs 3118, 3120. These are described in prior U.S. patent application Ser. No. 13/084,048 to Roman, filed Apr. 11, 2011, incorporated herein by reference.

In some embodiments, the barbs are flexible enough to bend if a hard cortical wall is engaged during insertion, providing a reduction in diameter, and enabling additional advancement into an intramedullary canal. In one embodiment, the flexing barbs invoke a change in diameter in the range of about 0.1-0.3 mm. In some examples, the barbs are designed in such a manner that one or both barbs can be trimmed intra-operatively with a straight pin cutter to reduce the diameter of the arrow to fit particularly narrow IM canals. If necessary, the arrowhead tip may be completely removed.

The body 3106 extends between and connects the distal head 3102 and the proximal head 3104. It is a one-piece rigid element structurally configured to withstand loading applied across the joint or fracture being supported. It includes a main body portion 3130 and necks 3132, 3134 at either end leading to the distal and proximal heads 3102, 3104. As can be seen, the main body portion 3130 has a diameter larger than that of the necks 3132, 3134. The larger body portion 3130 may be easier to grasp and secure with a surgical instrument because it has a larger perimeter surface area, while the necks 3132, 3134 may be sized to permit additional tissue placement and tissue growth immediately adjacent the undercut surfaces 3122, 3124 of the distal and proximal heads 3102, 3104. This may result in more secure and lasting anchoring. Thus, this structural arrangement may provide space for extra tissue to grow behind the arrowhead to aid in fixation, while still providing a large gripping surface on the body 3106.

Still referring to these figures, the second and fourth outer facing surfaces 3112, 3116 are angled and intersect with the body 3106 at the neck 3132. In some examples, the second and fourth outer facing surfaces 3112, 3114 may smoothly transition to the neck and in other examples; the second and fourth outer facing surfaces 3112, 3114 meet the neck 3132 at an intersecting angle. In some examples, the neck 3132 is formed with a rounded perimeter having a diameter substantially similar to the distance between the proximal ends of the second and fourth outer facing surfaces 3112, 3114.

The second or proximal head 3104 is, in the example shown, smaller than the distal head 3102, and extends from the body 3106 in the opposing direction. For clarity and to reduce duplication, much of the description above applies to the proximal head 3104 and is not repeated here with the understanding that the description above applies to the proximal head 3104. As such, the proximal head includes four main surfaces forming an arrowhead, labeled as fifth, sixth, seventh, and eighth surfaces. As can be seen, some of these surfaces form an angle β and others form an angle φ relative to the longitudinal axis. In one embodiment, the angle β is smaller than the angle θ. In some embodiments, the angle β ranges from about 7-25 degrees, and in one embodiment is 11 degrees. The angle φ may be within a range discussed above relative to the angle α, and in one embodiment, is equal to the angle α.

In this embodiment, the proximal head 3104 is formed with trailing edge surfaces 3140 instead of projecting barbs. The trailing edge surfaces 3140 enable bone ingrowth immediately adjacent the trailing edge surfaces, resulting in a relatively quick purchase of the proximal head 3104 during healing. The trailing edge surfaces 3140 extend substantially perpendicular to the longitudinal axis 3117 of the device 3100.

The proximal head 3104 is sized and configured to be implanted in the subchondral bone at the base of the proximal phalanx. While this proximal head 3104 has a smaller diameter and length than the larger distal head 3102, because it is implanted in the more dense subchondral bone at the base of the proximal phalanx, the proximal head may achieve a stability and resistance to migratory forces that is similar to that of the larger distal head 3102, which is shaped and configured to be inserted in the less dense cancellous bone of the middle phalanx.

In the example shown the distal head 3102 has a length that is about 1.5 times the length of the proximal head 3104. Likewise, it has an overall width about 1.3-1.5 times the width of the proximal head 3104.

Some embodiments of the device include a body having a plantar grade bend. Different embodiments include a bend that may be selected in the range of about 5-25 degrees. In some examples, the bend is selected to be about a 15 degree bend, while yet other embodiments the bend is selected to be about a 10 degree bend, an in another, about a 5 degree bend.

FIGS. 37-41 show another exemplary embodiment of a device, referenced herein as a device 4200. The device 4200 is designed with a three-dimensionally configured arrow at each end and includes a distal head 4202, a proximal head 4204, and a body 4206 extending between the distal and proximal heads 4202, 4204 and having a longitudinal axis 4207. Features consistent with those described above will not be repeated here for the sake of simplicity, but it is understood that the relevant description of features relative to other embodiments described herein also apply to the device 4200.

The distal head 4202 includes a central core portion 4208 and a plurality of radially extending distal wings 4210. The core portion 4208 extends along the longitudinal axis 4207 of the body 4206 and includes the distal end 4212. In this example, the distal end 4212 is rounded or blunt end to provide smooth insertion into the medullary canal. In addition, because of its rounded shape, when implanted in techniques using bored or reamed holes, the surgeon can feel tactilely when the implant is inserted to the depth of the bored or reamed hole because the rounded end resists further insertion at low insertion forces. However, the surgeon may still insert the device into the intramedullary canal beyond the end of the bored or reamed area by applying additional force. In this embodiment, the distal end 4212 is formed of a convexly shaped leading nub 4214 extending from the surfaces leading to the wings 4210.

The plurality of wings 4210 extend radially from the core portion 4208 and define the outer shape of the distal head 4202. In the embodiment shown, the head 4202, as measured from wing to wing, has a diameter sized to fit within an intramedullary canal of a phalanx and more particularly, within a medullary canal of a middle phalanx.

The wings themselves include an outer surface portion 4216, a trailing surface portion 4222, and lateral sides 4224. In the exemplary embodiment shown, the outer surface portion 4216 of the wings 4210 includes a cylindrical surface portion 4218 and a curved leading surface portion 4220. The outer perimeter surface portion 4218 extends in the longitudinal direction and then intersects with the curved leading surface portion 4220. In this example, the outer perimeter surface portion 4218 of the plurality of wings 4210 together also defines an outer diameter or outer width W1 (FIG. 38) of the distal head 4202. In some embodiments, the head has a width sized within the range of about 2.0 mm to 4.5 mm. In one embodiment, the width W1 is sized within the range of about 3.0 mm to 4.0 mm. In one embodiment, the width W1 is sized within the range of about 3.5 mm. In some embodiments, the outer perimeter surface portion 4218 of the wings 4210 has a curved outer surface that lies along the boundary of a cylindrical shape at the maximum diameter or width W1, as represented by the dashed lines in FIG. 38. Some embodiments are sized to accommodate a particular bone quality and intramedullary canal diameter. For example, for softer bone quality or for larger canals, the diameter of the distal head may be selected to be within a range of 2.5 mm to 5.0 mm.

Extending from the outer perimeter surface portion 4218, the wings 4210 include the curved leading surface portion 4220. The curved leading surface portion 4220 faces at least partially in the direction of the distal end 4212, and curves from the outer surface portion 4216 toward and smoothly intersects with the core portion 4208. In some embodiments, the curved leading surface portion 4220 has a radius within a range of about 1 mm to 4 mm, and in some embodiments has a radius within a range of about 1.5 mm to 2.5 mm. In one embodiment, the radius is 2 mm.

The trailing surface portion 4222 is a surface extending radially inward from the outer surface portion 4216 toward the longitudinal axis of the device 4200 and intersects with the core portion 4208. In the embodiment shown, the trailing surface portion 4222 has a surface that lies substantially normal to the longitudinal axis 4207, although in other embodiments, it may be angled obliquely relative to the longitudinal axis. A rounded, distally projecting edge 4228 connects the trailing surface portion 4222 to the outer perimeter surface portion 4218 of the outer surface portion 4216.

In the embodiment shown, each wing 4210 includes two lateral sides 4224. In the example shown, the lateral sides extend from the outer surface portion 4216 to the core portion 4208. Depending on the embodiment, these lateral sides 4224 may be formed in parallel planes or may be wedge-shaped. The thickness of the wing 4210 is defined by the distance between the lateral sides 4224 and the pull-out resistance is determined by the thickness of the wing 4210 at the trailing surface portion. A wing 4210 having lateral sides 4224 in parallel planes will have uniform thickness and may be easier to implant while still providing rotational stability.

In other embodiments however, these lateral sides 4224 may be formed of nonparallel planes and may form a wedge-shape. For example, one embodiment includes a wing 4210 having a leading portion having a thickness about 0.38 mm at the leading end and a thickness of about 0.52 mm at the trailing end. Other angles and dimensions are also contemplated. Accordingly, the wings are thinner toward the leading end than the trailing end. Embodiments with wedge-shaped wings may require more force to implant. However, they may also provide closer contact between the bone and the wing 4210 because the wing may become gradually thicker from the leading edge to the trailing edge. In addition, increasing thickness of the wing toward the trailing edge maximizes the resistance to pull-out because the wing at the trailing surface portion is at its thickest location.

In some embodiments, the lateral sides 4224 are nonplanar and have a curved surface that promotes interference with bone tissue to resist migration and rotation. Some embodiments include wings that vary by wing thickness. For example, some embodiments include two wings having a first thickness and two additional wings having a second thickness greater than the first thickness. The core portion 4208 smoothly connects and spans between adjacent wings with a cylindrical surface 4232 that extends the length of the wings 4210.

Because the distal end 4212 has a smooth bullet-nose shape, the likelihood of the distal end catching on the cortex and preventing the implant from being advanced smoothly may be diminished. During insertion, the wings 4210 act as sled runners to help the device 4200 slide easily down a reamed pilot hole. In addition, the smooth and curved leading surface portion 4220 on the wings 4210 may enable the implant to be self-centering during the insertion process.

While the distal head 4202 is shown having four wings 4210 forming a plus or cruciate configuration, other embodiments include a different number of wings. One embodiment includes three wings, while another embodiment includes two wings. Yet other embodiments include more than four wings. Depending on the embodiment, the distal head 4202 may comprise between three and eight distal wings 4210 arranged in a symmetric or asymmetric manner. Some examples have distal wings forming a cruciate or plus shape, an X shape, a five-sided star shape, or a six-sided star shape, or a four-wind dorsally (like an underlined V), among other possible combinations. The number of wings may affect the pull-out resistance of the device 4200. For example, a balance between the number of wings and their relative size may permit the device to be designed to achieve a desired pull-out resistance. Reducing the diameter of the wings may permit the device 4200 to be implanted within smaller diameter intramedullary canals while still providing suitable resistance to pull-out. Some embodiments have the wings of the proximal head rotatably offset from the wings of the distal head. For example, while the wings on the distal head may be disposed at 3, 6, 9, and 12 o'clock, the wings on the proximal head may be disposed at 2, 5, 8, and 11 o'clock. In some embodiments, the wings are offset by 45 degrees.

Because of the central core portion 4208 design, the pilot hole preparation may be done with a rotary motion, such as a power or manual reamer or drill, thereby possibly reducing the need for the step of broaching the pilot hole to form a rectangular cavity.

Some embodiments include a head length that is minimized in order to permit as much bone growth behind the trailing surface portion possible to contribute to resistance to pull-out. In one embodiment, the length of the distal head is within the range of about 2.0 mm to 3.0 mm. Other sizes are also contemplated.

The blade orientation for the distal head 4202 provides not only resistance to rotation and pull-out but also may ease pulling the middle phalanx over the distal head 4202 as it the portion of the device that protrudes from the proximal phalange during insertion.

The proximal head 4204 includes a central core portion 4240 and a plurality of radially extending wings 4242. Many features of the proximal head 4204 are similar to that of the distal head 4202 and not all the features are re-described here, recognizing that one of ordinary skill would understand that features and alternatives described relative to the distal head 4202 have equal applicability to the proximal head 4204. Like the core portion 4208 of the distal head 4202, the central core portion 4240 extends along the longitudinal axis 4207 of the body 4206. The core portion 4240 includes a proximal end 4244. In this example, the core portion 4240 and the proximal end 244 differs in shape as described below, while still maintaining a rounded or blunt end to provide smooth insertion into the medullary canal. In this embodiment, the core portion proximal end 4244 includes a conical surface portion 4256 that connects the leading surface portion 4250 and includes a convexly shaped leading nub 4245 extending from the surfaces leading to the wings 4242.

The plurality of wings 4242 extend radially from the core portion 4240 and define the outer shape of the proximal head 4204. In the embodiment shown, the head 4202, as measured from wing to wing, has a diameter sized to fit within an intramedullary canal of a phalanx and more particularly, within a canal of a proximal phalanx.

The wings 4242 themselves include an outer surface portion 4246, a trailing surface portion 4252, and lateral sides 4254. In the exemplary embodiment shown, the outer surface portion 4246 of the wings 4242 includes an outer perimeter surface portion 4248 and a curved leading surface portion 4250. The outer perimeter surface portion 4248 extends in the longitudinal direction and then intersects with the curved leading surface portion 4250. In this example, the outer perimeter surface portion 4248 of the plurality of wings 4242 together also defines an outer diameter or outer width W2 (FIG. 41) of the distal head 4202. In some embodiments, the proximal head 4204 has a width sized within the range of about 1.0 mm to 3.5 mm. In one embodiment, the width W2 is sized within the range of about 2.0 mm to 3.0 mm. In one embodiment, the width W2 is sized within the range of about 2.5 mm. In some embodiments, the outer perimeter surface portion 4248 of the wings 4242 has a curved outer surface that lies along the boundary of a cylindrical shape at the maximum diameter or width W2, as represented by the dashed lines in FIG. 41.

Extending from the outer perimeter surface portion 4248, the wings 4242 include the curved leading surface portion 4250. The curved leading surface portion 4250 curves from the outer surface portion 4216 toward and smoothly intersecting with the conical surface portion 4256 of the core portion 4208. In some embodiments, the curved leading surface portion 4250 has a radius sized in the ranges as described with reference to the curved leading surface portion 4220. In one embodiment, the covered leading surface portions 4220, 4250 have the same radius.

The trailing surface portion 4252 extends radially inward from the outer surface portion 4246 toward the longitudinal axis of the device 4200 and intersects with the core portion 4240. A rounded edge 4258 connects the trailing surface portion 4252 to the outer perimeter surface portion 4248 of the outer surface portion 4246.

Each wing 4242 includes two lateral sides 4254. In one embodiment, the thickness of the wings 4242 is measured between the lateral sides 4254 and is in the range of 0.020 mm and 0.060 mm. In one embodiment, the wings are wedge shaped and taper from a thickness of 0.37 mm at its leading end to 0.053 at its trailing end.

As indicated above, the overall length of the proximal head 4204 is greater than that of the distal head 4202. However, the length can be shortened to enhance pull-out resistance. For example, the resistance to pull-out may increase as the distance from the trailing surface portion of the distal or proximal head to the osteotomy increases. For the distal head 4202 that is implanted in the middle phalanx, a shorter head may offer resistance to rotation and still increase the distance from the trailing surface portion of the implant wings to the osteotomy site when implanted to the same depth. Because the trailing surface portion of the wing on the shorter head is farther from the fracture site, a radiograph would give the appearance of the device being more deeply implanted in the middle phalanx. As such the distal head 4202 with its larger diameter is intended for implantation in the medial phalanx and the proximal head 4204 with its smaller diameter is intended for implantation in the proximal phalanx.

The body 4206 is a rigid shaft extending between and connecting the distal head 4202 and the proximal head 4204. In the embodiment shown, the body 4206 is cylindrically shaped and has a substantially smooth exterior surface. In one embodiment, the body 4206 has a diameter or a cross-sectional thickness within a range of about 1.2 mm to 2.0 mm. In one embodiment, the body 4206 has a diameter or a cross-sectional thickness of about 1.6 mm. Other sizes, larger and smaller are contemplated. The body 4206 includes a necked-down region adjacent the proximal and distal head as the body merges with the central core portion.

In some embodiments, the proximal and distal heads form about a 30% or less of the overall length of the device. In one example, the distal head has a length of about 2.5 mm, the proximal head has a length of about 3.0 mm, and the body has a length about 13.5 mm or greater.

In the embodiment shown, the body 4206 has a substantially constant diameter. However, some embodiments have body diameters that vary along the length of the body 4206 to correspond to forces and to increase the area of the arrowhead tip resisting pull-out and rotational forces. Two such embodiments are described below relative to FIGS. 42 and 43.

Figure 42:
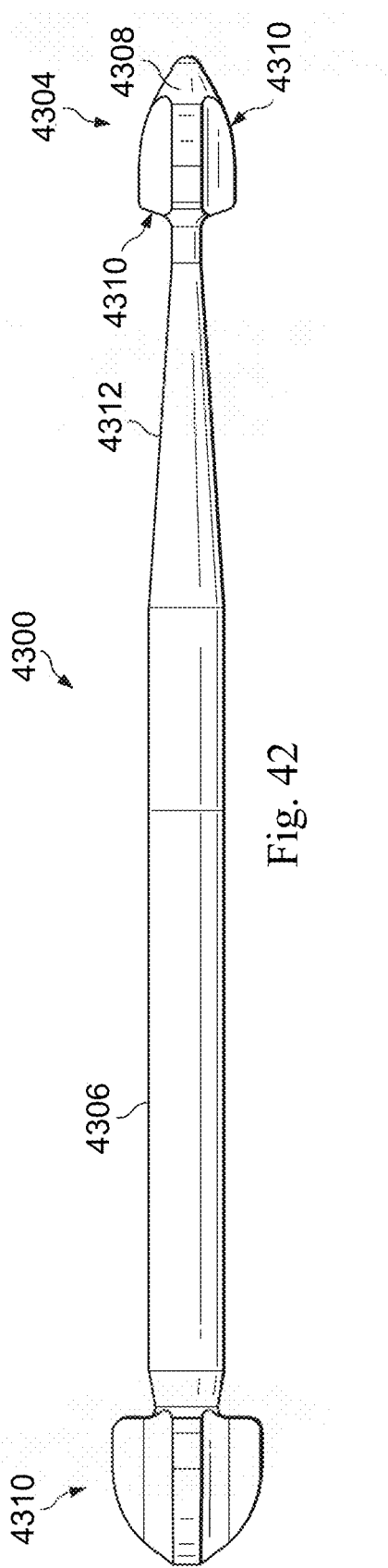
FIG. 42 is an illustration of another exemplary intramedullary fixation device in accordance with one aspect of the present disclosure.

FIG. 42 shows another embodiment of a device referenced herein by the numeral 4300. The device 4300 includes a distal head 4302, a proximal head 4304, and a body 4306. The distal and proximal heads 4302, 4304 include features similar to those described above, and the descriptions apply to this embodiment, recognizing that the size ratio of the different heads may differ on the device 4300. Here, the proximal head 4304 include a core portion 4308 and wings 4310. The body 4306 in this embodiment includes a tapered shaft region 4312 that extends along a substantial portion of the body 4306.

In this embodiment, the size ratio of tapered shaft region 4312 to the adjacent core portion 4308 of the head may be selected to be minimized. This may permit the body 4306 to be deeply embedded within the phalanx with a minimal amount of tissue disruption. Some embodiments have less than a 1:1.5 tapered shaft region to core portion size ratio, while other embodiments have a 1:1 size ratio. Other sizes and ratios are contemplated. The reduced diameter of the tapered shaft region 4308 may extend less than half the distance of the body 4306 so that the thicker region of the body 4306 may be disposed at the fusion region when the device 4200 is implanted. In the exemplary embodiment shown, the tapered shaft region 4312 extends for a length of more than about 15% of the length of the entire body. In one embodiment, the tapered shaft region 4312 extends from the proximal head a distance between about 15% and 45% of the length of the body 4306. In some examples, the tapered shaft region 4312 extends a distance within a range of about 20% and 30% of the length of the body 4306. This may provide a suitable region for bone ingrowth behind the proximal head 4304, while still having the thicker portion of the body at the osteotomy site. While referred to as a tapered shaft region 4312, the narrow region of the shaft may also be cylindrical, and may be referred to as a narrow region.

This also may permit the proximal head 4304 to be embedded in the subchondral bone of the proximal phalanx. Reducing the ratio of the core portion 4308 to the body 4306 may increase the resistance to rotation and pull-out. In one embodiment, the body diameter or width is set at a diameter of 1.0 mm so that an additional 0.25 mm per wing (0.5 mm total) is available to resist rotational forces. The increased area resisting pull-out is also 0.25 mm per wing multiplied by the width of the wing 4310 at the trailing surface portion, multiplied by the number of wings 4310. In this embodiment, a reamer width would be reduced to the width of the body 4306 at the narrowest point.

In the example shown, the thickness or cross-sectional width of the body 4306 that aligns with the osteotomy site and into the distal tip of the implant would remain at the thickest portion of the body 4306, which in one embodiment, is 1.6 mm.

Figure 43:
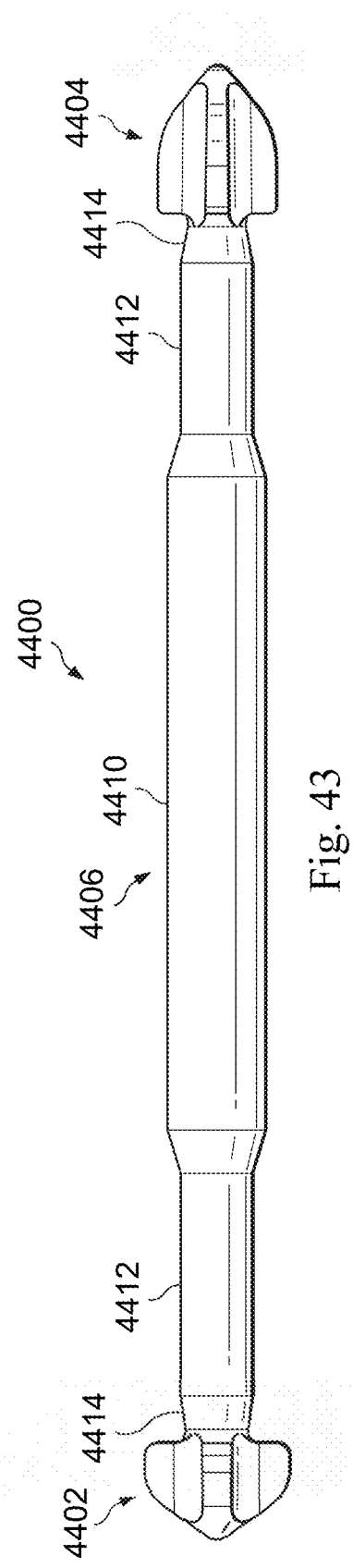
FIG. 43 is illustrations of another exemplary intramedullary fixation device in accordance with one aspect of the present disclosure.
Figure 44:
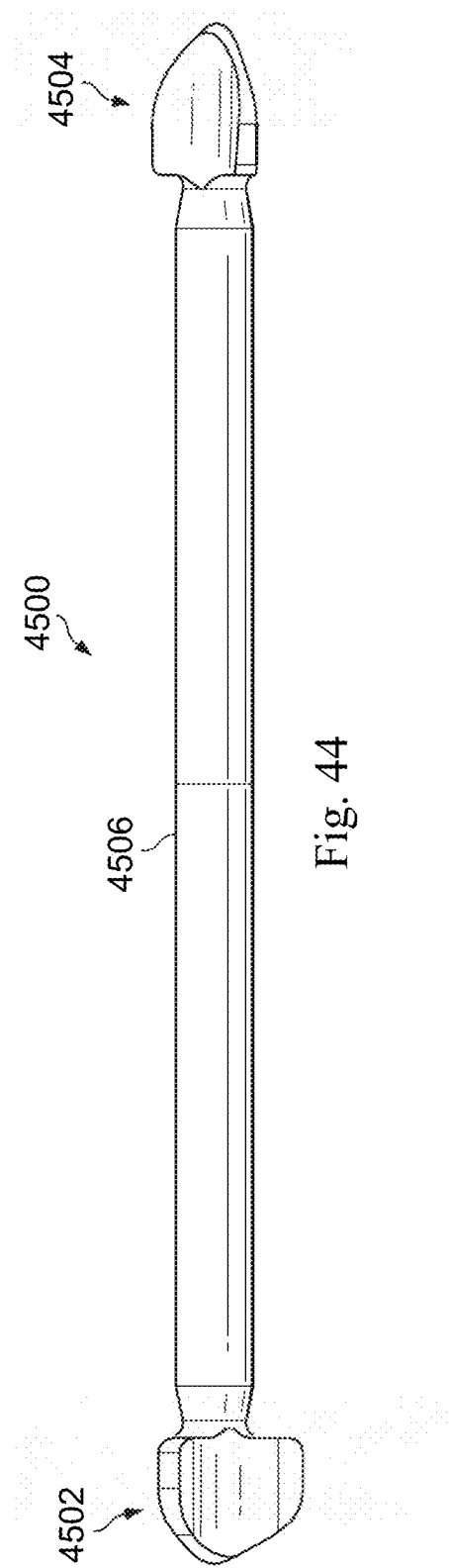
Figure 46:
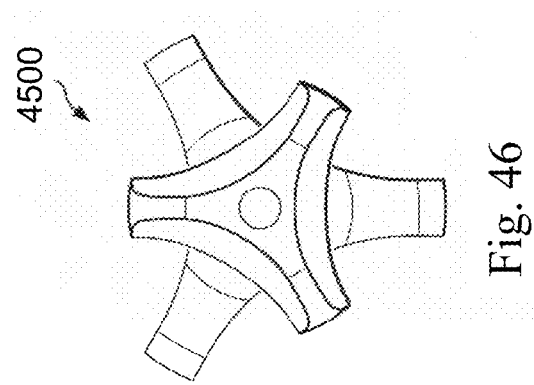
Figure 45:
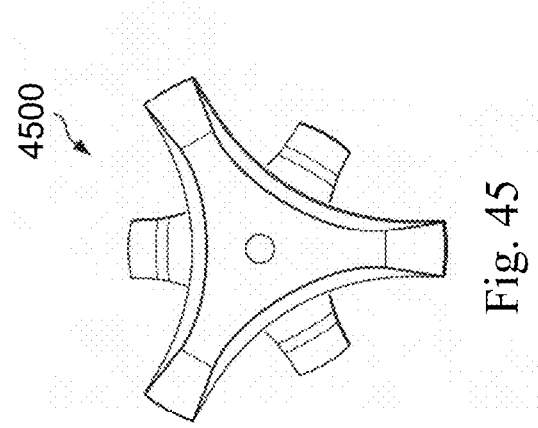

FIG. 43 shows another embodiment of a device, reference herein by the numeral 4400. The device 4400 includes a distal head 4402, a proximal head 4404, and a body 4406. The distal and proximal heads 4402, 4404 include features similar to those described above, and the descriptions apply to this embodiment, recognizing that the size ratio of the different heads may differ on the device 4400. In this embodiment, the body 4406 includes a central region 4410 of increased thickness. Accordingly, the body 4406 includes narrower regions 4412 at the distal and proximal ends, and these narrow further at necks 4414 to form the respective distal and proximal heads 4402, 4404.

Here, the central region 4410 may provide greater strength and a tighter fit at the site of the osteotomy. In one embodiment, the width or diameter of the body 4106 in the central region 4410 is within a range of about 1.8 mm-2.2 mm to enhance the fixation at the osteotomy site and to stabilize the device by helping to reduce play of the device 4200. This may also increase the strength of an already strong implant at the point of greatest potential stresses. In such an embodiment, the reamer diameter may remain at a size to accommodate the narrower regions 4412. For example, the narrow regions 4412 may have a diameter of about 1.6 mm, and therefore, in some examples, the reamer diameter would also be 1.6 mm. In one embodiment, the central region 4410 may extend about 40-70% of the length of the body. In other embodiments, the central region extends about 40-60% of the length of the body.

Figure 40:
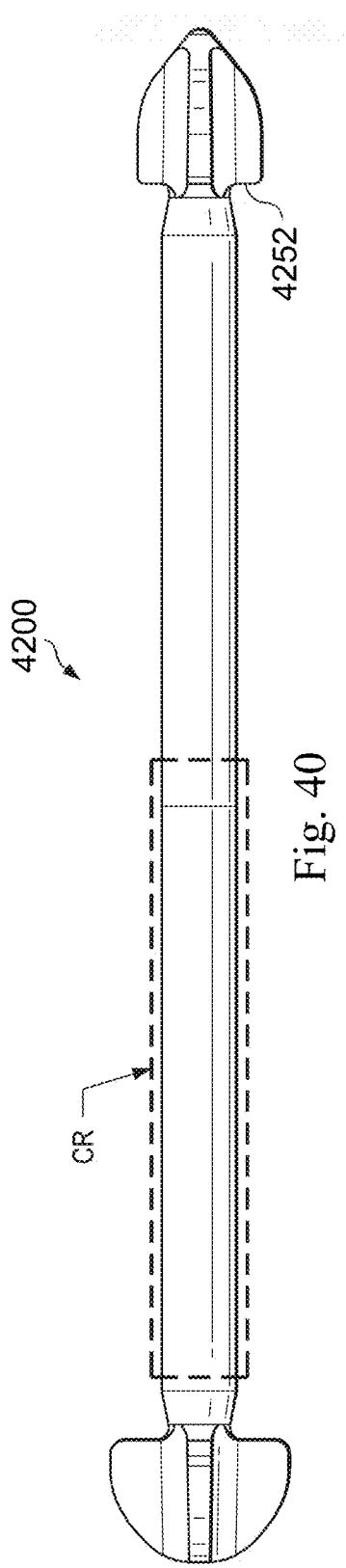
Figure 41:
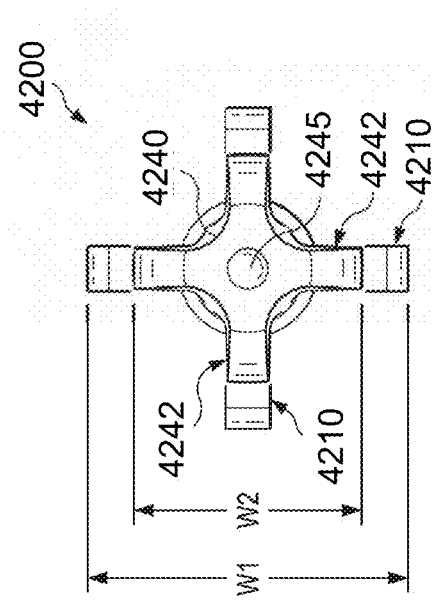

Some embodiments of the bodies disclosed herein include a coating or tissue growth material. For example, some embodiments include an aggressive porous material or coating that is "sticky" to tissue. Some examples include a bone-growth promoting substance, such as, for example, a hydroxyapatite coating formed of calcium phosphate, tricalcium phosphate (TCP), and/or calcium carbonate. Alternatively, osteoinductive coatings, such as proteins from transforming growth factor (TGF) beta superfamily, or bone-morphogenic proteins, such as BMP2 or BMP7, may be used. These coatings may increase adhesion to cancellous bone, increasing resistance to pull-out and rotational forces. They also may accelerate bony ingrowth and accelerate consolidation of the bone. The coating may be applied along the entire body of the device, or may be applied only along a specific region, such as a region, such as the half of the body adjacent the distal head, for example. FIG. 40 shows one example of a coating region, identified by the box labeled CR. The coating may be arranged in other ways also.

Although shown as cylindrical, any of the bodies disclosed herein may have a cross-section of any suitable shape, and may include, for example, a shaft shape that is triangular shaped, square shaped or one with edges rather than cylindrical. These types of body cross-sections can provide additional resistance to rotational forces. In another example, edges emerging from the body can serve to provide additional fixation.

In some embodiments, the proximal head 4204 is sized and configured to be embedded in the subchondral bone at the base of the proximal phalanx. The rounded blunt tip may require greater force than the sharper, pointier arrow of earlier devices to progress farther into the subchondral bone than the prepared hole provides. Accordingly, the blunt bullet nose may prevent the implant from advancing past the end of the reamed pilot hole.

In one embodiment, the length of the proximal head is about 2.0 mm in the longitudinal direction. This length permits the addition of one or two additional wings that may increase both the level of the resistance to rotation and pull-out without increasing the length of the arrowhead. Increasing the length could adversely affect the pull-out resistance in vivo, for example, if the longer arrowhead were to not be completely embedded in subchondral bone. In this example, the wings are formed so that the head is substantially symmetrical. In other examples however, the proximal head comprises between three and eight proximal wings arranged in a symmetric or asymmetric manner. Some examples have proximal wings forming a cruciate or plus shape, an X shape, a five-sided star shape, or a six-sided star shape, or a four-wind dorsally (like an underlined V), among other possible combinations.

FIGS. 44-48 show an additional embodiment of a device, referenced herein by the numeral 500, including a distal head 502, a proximal head 504, and a body 506. The distal and proximal heads 502, 504 include features similar to those described above, and the descriptions apply to this embodiment, recognizing that the size ratio of the different heads may differ on the device 500. In this embodiment, the distal and proximal head each include three wings radially extending from a central core. As can be seen, and consistent with the description above, the distal head has a greater width and a smaller length than the proximal head. Here, as can be seen in the end views shown in FIGS. 45 and 46, the wings of the distal head and the proximal head are rotationally offset. Since there are three wings, they are rotationally offset by 60 degrees.

The devices may be implanted using any of a number of surgical instruments or tools, including for example, a reamer, a broach, and an insertion forceps. These instruments are described in detail in prior U.S. patent application Ser. No. 13/084,048 to Roman, filed Apr. 11, 2011, and incorporated herein by reference.

Furthermore, the devices disclosed herein may be provided as a kit in combination with a plurality of devices of different sizes or the instruments themselves. One exemplary kit includes a device as described above, with the reamer, the broach, and the insertion forceps. Other kits are described in prior U.S. patent application Ser. No. 13/084,048 to Roman, filed Apr. 11, 2011, and incorporated herein by reference.

The devices herein may be used in exemplary surgical methods for implanting the device for the treatment or correction of bone deformities. When implanted, the arrowhead configuration of both the distal and proximal heads captures bone on both sides of the fusion or fracture site, and may provide internal stability. This is accomplished by pressing and locking the distal and proximal heads into the surrounding bone. The body of the device extends from each head (proximal and distal) and is the portion of the implant that crosses or spans the fusion or fracture site.

Figure 49:
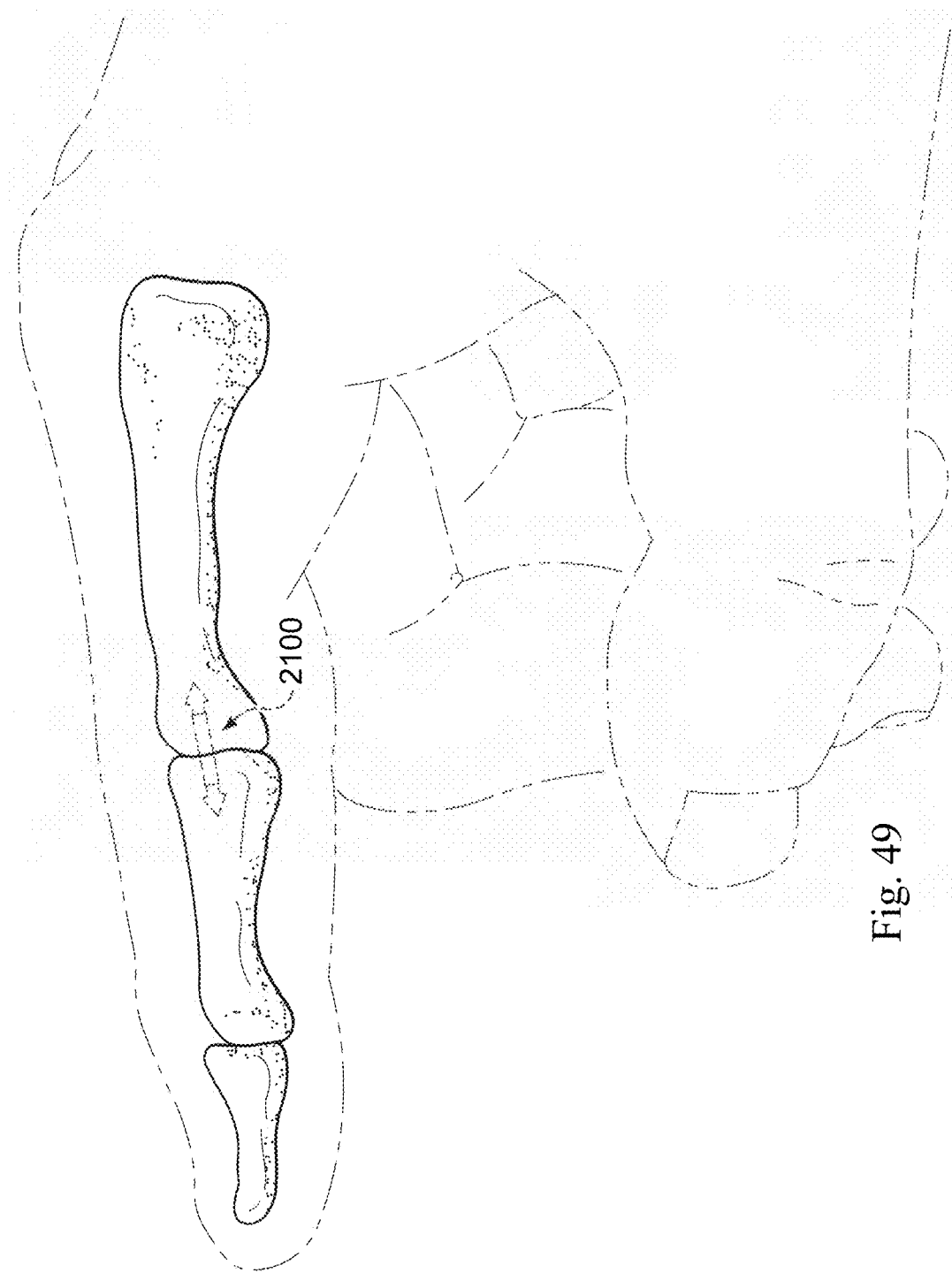
FIG. 49 is an illustration of an exemplary intramedullary fixation device disposed between and within adjacent phalanges of a hand of a patient in accordance with one aspect of the present disclosure.

It should be noted that the exemplary devices described herein may be used for treatments such as hammertoe, and in some examples, may be used to treat conditions in the fingers of a hand, or alternatively may be used to treat bone fractures. FIG. 49 is one example showing an example device, which could be any of the devices disclosed herein implanted within phalanges of the hand. In addition, removal of the device may be relatively easier than prior, conventional devices. For example, to remove the device, the cylindrical main body may be first cut, and then a cannulated drill may be fit over the cylindrical main body and drilled over to remove bony on-growth from the cylindrical body so that the arrowhead tip can be removed without tearing the bone. This may prevent the health care provider from having to cut the cortical bone in order to remove the implant. Accordingly, the cylindrical shape of the main body may help reduce a chance of compromising cortical bone during revision surgeries. Uses of the device may include but are not limited to hand surgery, orthopedic surgery, plastic surgery, and podiatric surgery. In addition, the implant may be inserted in a variety of angles that differ from its intended position in medullary bone. In some examples, the implant may also be placed through cortical bone and tendon of the hand or foot.

In some examples, the device is machined from a single piece of 316L stainless steel, making it a weld-less, single monolith structure. In other embodiment, it may be formed of two structures welded or brazed together, as shown in the cross-sectional view in FIG. 36. Various lengths may be provided to meet patient sizing restrictions. The overall lengths of the device may be in the range of 10 mm to 40 mm, while some lengths are within the range of 15 mm to 25 mm. When the device is formed of a single piece of metal, potential stress-risers occurring from welds or adhesives are eliminated and there is no need to assemble intra-operatively. Further, the material and size are selected so that the device has bending and fatigue characteristics able to endure the forces exerted on the lesser toes.

In some examples, the arrowheads may be reconfigured at different positions to one another and may obtain the same stability to the arthrodesis/fracture site. For example, some embodiments have a proximal arrow vertical to the shaft or a distal arrow horizontal to the shaft. The same can be said for different angle increments to each arrow.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. An intramedullary fixation device, comprising:
an arrow-shaped first head comprising a first end having a first tip and a pair of first wings, the first head being sized to fit within an intramedullary canal of a first bone portion;
an arrow-shaped second head comprising a second end having a second tip and a pair of second wings; and
a rigid body defining a longitudinal axis connecting the first head and the second head, the rigid body comprising an intermediate portion, a first neck portion connecting the rigid body to the first head, and a second neck portion connecting the rigid body to the second head, the first and second neck portions having a cross-sectional area smaller than a cross-sectional area of the intermediate portion,
wherein the first wings comprise first trailing edge surfaces extending inwardly from first outer tips to undercut surfaces at an angle to the longitudinal axis, the undercut surfaces extending from the first trailing edge surfaces further inwardly and toward the first tip and intersect with the first neck region of the rigid body such that at least a portion of the undercut surfaces is positioned between the first tip and the first trailing edge surfaces along a longitudinal direction, and
wherein the second wings comprise second trailing edge surfaces extending inwardly from second outer tips of the second wings at an angle to the longitudinal axis and intersect with the second neck region of the rigid body.

2. The intramedullary fixation device of claim 1, wherein the first head further comprises first, second, third, and fourth outwardly facing side surfaces forming a pyramidal shape, the first and third side surfaces being opposed from each other and forming a first angle, and the second and fourth side surfaces being opposed from each other and forming a second angle, each of the first and third side surfaces having a second edge configured to inhibit rotational movement and inhibit axial movement of the first head in a second direction.

3. The intramedullary fixation device of claim 2, wherein the first trailing edge surfaces extend from the second edges of the first and third side surfaces.

4. The intramedullary fixation device of claim 2, wherein the first and second angles are different angles.

5. The intramedullary fixation device of claim 2, wherein the first, second, third, and fourth outwardly facing side surfaces of the first head are planar surfaces.

6. The intramedullary fixation device of claim 2, wherein the second and fourth surfaces intersect with the first neck portion, and wherein the first and third surfaces do not intersect with the first neck portion.

7. The intramedullary fixation device of claim 2, wherein the second head further comprises fifth, sixth, seventh, and eighth outwardly facing side surfaces, the fifth and seventh side surfaces being opposed from each other and forming a third angle, and the sixth and eighth side surfaces being opposed from each other and forming a fourth angle, the third angle being different than the fourth angle, each of the fifth and seventh side surfaces defining the first outer tips of the second wings configured to inhibit rotational movement and inhibit axial movement of the second head in a first direction.

8. The intramedullary fixation device of claim 7, wherein the second trailing edge surfaces extend from the first edges of the fifth and seventh side surfaces.

9. The intramedullary fixation device of claim 7, wherein the first and third angles are different angles.

10. The intramedullary fixation device of claim 7, wherein the fifth, sixth, seventh, and eighth outwardly facing side surfaces of the second head are planar surfaces.

11. The intramedullary fixation device of claim 7, wherein the sixth and eight surfaces intersect with the second neck portion, and wherein the fifth and seventh surfaces do not intersect with the second neck portion.

12. The intramedullary fixation device of claim 1, wherein the rigid body comprises a first portion and a second portion, the first portion being angled relative to the second portion.

13. The intramedullary fixation device of claim 1, wherein the first head has a first dimensional width measured between the first outer tips of the first wings, and the second head has a second dimensional width measured between the second outer tips of the second wings, the first dimensional width being greater than the second dimensional width.

14. The intramedullary fixation device of claim 13, wherein the first dimensional width is within the range of about 1.3 to about 1.5 times the second dimensional width.

15. The intramedullary fixation device of claim 1, wherein the first head defines a first longitudinal length and the second head defines a second longitudinal length, the first length being greater than the second length.

16. The intramedullary fixation device of claim 15, wherein the first longitudinal length is about 1.5 times the second longitudinal length.

17. The intramedullary fixation device of claim 1, wherein the first head defines a first longitudinal length and a first dimensional width measured between the first outer tips of the first wings, and wherein the first dimensional width is greater than the first longitudinal length.

18. The intramedullary fixation device of claim 1, wherein the first tip of the first head forms a sharp point, and the second tip of the second head forms a sharp point.

19. The intramedullary fixation device of claim 1, wherein the first trailing edge surfaces extending linearly inwardly from first outer tips to the undercut surfaces at an angle to the longitudinal axis, and the undercut surfaces extend arcuately from the first trailing edge surfaces further inwardly and toward the first tip and intersect with the first neck region of the rigid body such that at least a portion of the undercut surfaces is positioned between the first tip and the first trailing edge surfaces along a longitudinal direction.

20. The intramedullary fixation device of claim 1, wherein the first wings of the first head are positioned on opposing sides of the longitudinal axis, and second wings of the second head are positioned on opposing sides of the longitudinal axis.

* * * * *